United States Patent [19]
Huse

[11] Patent Number: 5,871,974
[45] Date of Patent: Feb. 16, 1999

[54] SURFACE EXPRESSION LIBRARIES OF HETEROMERIC RECEPTORS

[75] Inventor: William D. Huse, Del Mar, Calif.

[73] Assignee: Ixsys Inc., San Diego, Calif.

[21] Appl. No.: 349,131

[22] Filed: Dec. 2, 1994

Related U.S. Application Data

[63] Continuation of Ser. No. 120,648, Sep. 13, 1993, abandoned, which is a continuation of Ser. No. 767,136, Sep. 27, 1991, abandoned, which is a continuation-in-part of Ser. No. 590,219, Sep. 28, 1990, abandoned.

[51] Int. Cl.$^6$ .............................. C12N 15/63; C12N 15/13
[52] U.S. Cl. .................... 435/69.7; 435/69.1; 435/172.3; 435/252.3; 435/320.1; 536/23.4
[58] Field of Search .................................. 435/69.1, 69.7, 435/172.3, 252.3, 320.1; 536/23.4

[56] References Cited

U.S. PATENT DOCUMENTS

| | | | |
|---|---|---|---|
| 5,223,409 | 6/1993 | Ladner et al. | 435/69.7 |
| 5,403,484 | 4/1995 | Ladner et al. | 435/235.1 |
| 5,427,908 | 6/1995 | Dower et al. | 435/5 |
| 5,432,018 | 7/1995 | Dower et al. | 435/5 |

FOREIGN PATENT DOCUMENTS

| | | |
|---|---|---|
| 62-8702671 | 5/1987 | WIPO . |
| 63-8806630 | 9/1988 | WIPO . |

OTHER PUBLICATIONS

Barbas, Carlos F. III, et al., "Assembly of Combinatorial Antibody Libraries on Phage Surfaces: The Gene III Site". Proc. Natl. Acad. Sci. USA. 88:7978–7982 (1991).
Clackson, Tim, et al., "Making Antibody Fragments Using Phage Display Libraries". Nature. 352:624–628 (1991).
Hoogenboom, Hennie R. et al., "Multi–Subunit Proteins on the Surface of Filamentous Phage: Methodologies for Displaying Antibody (Fab) Heavy and Light Chains". Nucleic Acids Res. 19:4133–4137 (1991).
Plückthun, A. "Antibodies from *Escherichia coli*". Nature. 347:497–498 (1990).
Caton, Andrew J. and Koprowski, Hilary, "Influenza Virus Hemagglutinin–Specific Antibodies Isolated from a Combinational Expression Library are Closely Related to the Immune Response of the Donor". Proc. Natl. Acad. Sci. USA. 87:6450–6454 (1990).
Hellström, K.E. et al., "Epitope Mapping and Use of Anti–Idiotypic Antibodies to the L6 Monoclonal Anticarcinoma Antibody". Cancer Res. 50:2449–2454 (1990).
Parmley, Stephen F. and Smith, George P. "Filamentous Fusion Phage Cloning Vectors for the Study of Epitopes and Design of Vaccines". Adv. Exp. Med. Biol. 251:215–218 (1989).
Ward, E. Sally, et al., "Binding Activities of a Repertoire of Single Immunoglobulin Variable Domains Secreted from *Escherichia coli*". Nature. 341:544–546 (1989).

Reidhaar–Olson, John F. et al., "Combinatorial Cassette Mutagenesis as a Probe of the Informational Content of Protein Sequences". Science. 241:53–57 (1988).
Skerra, Arne and Plückthun, Andreas, "Assembly of a Functional Immunoglobulin $F_v$ Fragment in *Escherichia coli*". Science. 240:1038–1041 (1988).
Roberts, S., et al., "Generation of an Antibody with Enhanced Affinity and Specificity for its Antigen by Protein Engineering". Nature. 328:731–734 (1987).
Kunkel, Thomas A., et al., "Rapid and Efficient Site–Specific Mutagenesis Without Phenotypic Selection". Methods in Enzymology. 154:367–382 (1987).
Derbyshire, Keith M., et al., "A Simple and Efficient Procedure for Saturation Mutagenesis Using Mixed Oligodeoxynucleotides". Gene. 46:145–152 (1986).
Smith, George, P., "Filamentous Fusion Phage: Novel Expression Vectors That Display Cloned Antigens on the Virion Surface". Science. 228:1315–1317 (1985).
Cabilly, Samuel et al., "Generation of Antibody Activity From immunoglobulin Polypeptide Chains Produced in *Escherichia coli*". Proc. Natl. Acad. Sci. USA. 81:3273–3277 (1984).
Better, Marc et al., "*Escherichia coli* Secretion of an Active Chimeric Antibody Fragment". Science. 240:1041–1043 (1988).
Cwirla, Steven E. et al., "Peptides on Phage: A Vast Library of Peptides for Identifying Ligands". Proc. Natl. Acad. Sci. USA. 87:6378–6382 (1990).
Scott, Jamie K. et al., "Searching for Peptide Ligands with an Epitope Library". Science. 249:386–390 (1990).
Devlin, James J. et al., "Random Peptide Libraries: A Source of Specific Protein Binding Molecules". Science. 249:404–406 (1990).
Parmley, Stephan F. and Smith, George P. "Antibody–selectable Filamentous fd Phage Vectors: Affinity Purification of Target Genes". Gene. 73:305–318 (1988).
Marvin, D.A. et al., "Structure and Assembly of Filamentous Bacterial Viruses". Nature. 253:19–23 (1975).
PNAS, 86:5728–5732, Aug. 1989, Sastry et, al. Cloning of the Immunological Repertoire in *Escherichia coli* For Generation of Monoclonal Catalytic Antibodies . . .
Science 246: 1275–1281, 8 Dec. 1989, Huse et. al. Generation of a Large Combinatorial Library of Immunoglobulin Repertoire in Phage Lamba.
Gene 73: 305–318, 1988, Parmley et al. Antibody–Selectably Filamentous fd Phase Vectors: Affinity Purification of Target Genes.

*Primary Examiner*—John Ulm
*Attorney, Agent, or Firm*—Campbell & Flores LLP

[57] ABSTRACT

A composition of matter comprising a plurality of procaryotic cells containing diverse combinations of first and second DNA sequences encoding first and second polypeptides which form a heteromeric receptor exhibiting binding activity toward a preselected molecule, those heteromeric receptors being expressed on the surface of filamentous bacteriophage.

32 Claims, 16 Drawing Sheets

```
     |   10      |   20      |   30      |   40      |   50      |   60
   1 AATGCTACTA CTATTAGTAG AATTGATGCC ACCTTTTCAG CTCGCGCCCC AAATGAAAAT   60
  61 ATAGCTAAAC AGGTTATTGA CCATTTGCGA AATGTATCTA ATGGTCAAAC TAAATCTACT  120
 121 CGTTCGCAGA ATTGGGAATC AACTGTTACA TGGAATGAAA CTTCCAGACA CCGTACTTTA  180
 181 GTTGCATATT TAAAACATGT TGAGCTACAG CACCAGATTC AGCAATTAAG CTCTAAGCCA  240
 241 TCTGCAAAAA TGACCTCTTA TCAAAAGGAG CAATTAAAGG TACTCTCTAA TCCTGACCTG  300
 301 TTGGAGTTTG CTTCCGGTCT GGTTCGCTTT GAAGCTCGAA TTAAAACGCG ATATTTGAAG  360
 361 TCTTTCGGGC TTCCTCTTAA TCTTTTTGAT GCAATCCGCT TTGCTTCTGA CTATAATAGT  420
 421 CAGGGTAAAG ACCTGATTTT TGATTTATGG TCATTCTCGT TTTCTGAACT GTTTAAAGCA  480
 481 TTTGAGGGGG ATTCAATGAA TATTTATGAC GATTCCGCAG TATTGGACGC TATCCAGTCT  540
 541 AAACATTTTA CTATTACCCC CTCTGGCAAA ACTTCTTTTG CAAAAGCCTC TCGCTATTTT  600
 601 GGTTTTTATC GTCGTCTGGT AAACGAGGGT TATGATAGTG TTGCTCTTAC TATGCCTCGT  660
 661 AATTCCTTTT GGCGTTATGT ATCTGCATTA GTTGAATGTG GTATTCCTAA ATCTCAACTG  720
 721 ATGAATCTTT CTACCTGTAA TAATGTTGTT CCGTTAGTTC GTTTTATTAA CGTAGATTTT  780
 781 TCTTCCCAAC GTCCTGACTG GTATAATGAG CCAGTTCTTA AAATCGCATA AGGTAATTCA  840
 841 CAATGATTAA AGTTGAAATT AAACCATCTC AAGCCCAATT TACTACTCGT TCTGGTGTTT  900
 901 CTCGTCAGGG CAAGCCTTAT TCACTGAATG AGCAGCTTTG TTACGTTGAT TTGGGTAATG  960
 961 AATATCCGGT TCTTGTCAAG ATTACTCTTG ATGAAGGTCA GCCAGCCTAT GCGCCTGGTC 1020
1021 TGTACACCGT TCATCTGTCC TCTTTCAAAG TTGGTCAGTT CGGTTCCCTT ATGATTGACC 1080
1081 GTCTGCGCCT CGTTCCGGCT AAGTAACATG GAGCAGGTCG CGGATTTCGA CACAATTTAT 1140
1141 CAGGCGATGA TACAAATCTC CGTTGTACTT TGTTTCGCGC TTGGTATAAT CGCTGGGGGT 1200
1201 CAAAGATGAG TGTTTTAGTG TATTCTTTCG CCTCTTTCGT TTTAGGTTGG TGCCTTCGTA 1260
1261 GTGGCATTAC GTATTTTACC CGTTTAATGG AAACTTCCTC ATGAAAAAGT CTTTAGTCCT 1320
1321 CAAAGCCTCT GTAGCCGTTG CTACCCTCGT TCCGATGCTG TCTTTCGCTG CTGAGGGTGA 1380
1381 CGATCCCGCA AAAGCGGCCT TTAACTCCCT GCAAGCCTCA GCGACCGAAT ATATCGGTTA 1440
1441 TGCGTGGGCG ATGGTTGTTG TCATTGTCGG CGCAACTATC GGTATCAAGC TGTTTAAGAA 1500
1501 ATTCACCTCG AAAGCAAGCT GATAAACCGA TACAATTAAA GGCTCCTTTT GGAGCCTTTT 1560
1561 TTTTTGGAGA TTTTCAACGT GAAAAATTA TTATTCGCAA TTCCTTTAGT TGTTCCTTTC 1620
1621 TATTCTCACT CCGCTGAAAC TGTTGAAAGT TGTTTAGCAA AACCCCATAC AGAAAATTCA 1680
1681 TTTACTAACG TCTGGAAAGA CGACAAAACT TTAGATCGTT ACGCTAACTA TGAGGGTTGT 1740
1741 CTGTGGAATG CTACAGGCGT TGTAGTTTGT ACTGGTGACG AAACTCAGTG TTACGGTACA 1800
1801 TGGGTTCCTA TTGGGCTTGC TATCCCTGAA AATGAGGGTG GTGGCTCTGA GGGTGGCGGT 1860
1861 TCTGAGGGTG GCGGTTCTGA GGGTGGCGGT ACTAAACCTC CTGAGTACGG TGATACACCT 1920
1921 ATTCCGGGCT ATACTTATAT CAACCCTCTC GACGGCACTT ATCCGCCTGG TACTGAGCAA 1980
1981 AACCCCGCTA ATCCTAATCC TTCTCTTGAG GAGTCTCAGC CTCTTAATAC TTTCATGTTT 2040
2041 CAGAATAATA GGTTCCGAAA TAGGCAGGGG GCATTAACTG TTTATACGGG CACTGTTACT 2100
2101 CAAGGCACTG ACCCCGTTAA AACTTATTAC CAGTACACTC CTGTATCATC AAAAGCCATG 2160
2161 TATGACGCTT ACTGGAACGG TAAATTCAGA GACTGCGCTT TCCATTCTGG CTTTAATGAA 2220
2221 GATCCATTCG TTTGTGAATA TCAAGGCCAA TCGTCTGACC TGCCTCAACC TCCTGTCAAT 2280
2281 GCTGGCGGCG GCTCTGGTGG TGGTTCTGGT GGCGGCTCTG AGGGTGGTGG CTCTGAGGGT 2340
2341 GGCGGTTCTG AGGGTGGCGG CTCTGAGGGA GGCGGTTCCG GTGGTGGCTC TGGTTCCGGT 2400
2401 GATTTTGATT ATGAAAAGAT GGCAAACGCT AATAAGGGGG CTATGACCGA AAATGCCGAT 2460
2461 GAAAACGCGC TACAGTCTGA CGCTAAAGGC AAACTTGATT CTGTCGCTAC TGATTACGGT 2520
2521 GCTGCTATCG ATGGTTTCAT TGGTGACGTT TCCGGCCTTG CTAATGGTAA TGGTGCTACT 2580
2581 GGTGATTTTG CTGGCTCTAA TTCCCAAATG GCTCAAGTCG GTGACGGTGA TAATTCACCT 2640
2641 TTAATGAATA ATTTCCGTCA ATATTTACCT TCCCTCCCTC AATCGGTTGA ATGTCGCCCT 2700
2701 TTTGTCTTTA GCGCTGGTAA ACCATATGAA TTTTCTATTG ATTGTGACAA AATAAACTTA 2760
2761 TTCCGTGGTG TCTTTGCGTT TCTTTTATAT GTTGCCACCT TTATGTATGT ATTTTCTACG 2820
2821 TTTGCTAACA TACTGCGTAA TAAGGAGTCT TAATCATGCC AGTTCTTTTG GGTATTCCGT 2880
2881 TATTATTGCG TTTCCTCGGT TTCCTTCTGG TAACTTTGTT CGGCTATCTG CTTACTTTTC 2940
2941 TTAAAAAGGG CTTCGGTAAG ATAGCTATTG CTATTTCATT GTTTCTTGCT CTTATTATTG 3000
     |   10      |   20      |   30      |   40      |   50      |   60
```

FIG. 2A

```
        |    10     |    20     |    30     |    40     |    50     |    60
3001    GGCTTAACTC  AATTCTTGTG  GGTTATCTCT  CTGATATTAG  CGCTCAATTA  CCCTCTGACT   3060
3061    TTGTTCAGGG  TGTTCAGTTA  ATTCTCCCGT  CTAATGCGCT  TCCCTGTTTT  TATGTTATTC   3120
3121    TCTCTGTAAA  GGCTGCTATT  TTCATTTTTG  ACGTTAAACA  AAAAATCGTT  TCTTATTTGG   3180
3181    ATTGGGATAA  ATAATATGGC  TGTTTATTTT  GTAACTGGCA  AATTAGGCTC  TGGAAAGACG   3240
3241    CTCGTTAGCG  TTGGTAAGAT  TCAGGATAAA  ATTGTAGCTG  GGTGCAAAAT  AGCAACTAAT   3300
3301    CTTGATTTAA  GGCTTCAAAA  CCTCCCGCAA  GTCGGGAGGT  TCGCTAAAAC  GCCTCGCGTT   3360
3361    CTTAGAATAC  CGGATAAGCC  TTCTATATCT  GATTTGCTTG  CTATTGGGCG  CGGTAATGAT   3420
3421    TCCTACGATG  AAAATAAAAA  CGGCTTGCTT  GTTCTCGATG  AGTGCGGTAC  TTGGTTTAAT   3480
3481    ACCCGTTCTT  GGAATGATAA  GGAAAGACAG  CCGATTATTG  ATTGGTTTCT  ACATGCTCGT   3540
3541    AAATTAGGAT  GGGATATTAT  TTTTCTTGTT  CAGGACTTAT  CTATTGTTGA  TAAACAGGCG   3600
3601    CGTTCTGCAT  TAGCTGAACA  TGTTGTTTAT  TGTCGTCGTC  TGGACAGAAT  TACTTTACCT   3660
3661    TTTGTCGGTA  CTTTATATTC  TCTTATTACT  GGCTCGAAAA  TGCCTCTGCC  TAAATTACAT   3720
3721    GTTGGCGTTG  TTAAATATGG  CGATTCTCAA  TTAAGCCCTA  CTGTTGAGCG  TTGGCTTTAT   3780
3781    ACTGGTAAGA  ATTTGTATAA  CGCATATGAT  ACTAAACAGG  CTTTTTCTAG  TAATTATGAT   3840
3841    TCCGGTGTTT  ATTCTTATTT  AACGCCTTAT  TTATCACACG  GTCGGTATTT  CAAACCATTA   3900
3901    AATTTAGGTC  AGAAGATGAA  GCTTACTAAA  ATATATTTGA  AAAAGTTTTC  ACGCGTTCTT   3960
3961    TGTCTTGCGA  TTGGATTTGC  ATCAGCATTT  ACATATAGTT  ATATAACCCA  ACCTAAGCCG   4020
4021    GAGGTTAAAA  AGGTAGTCTC  TCAGACCTAT  GATTTTGATA  AATTCACTAT  TGACTCTTCT   4080
4081    CAGCGTCTTA  ATCTAAGCTA  TCGCTATGTT  TTCAAGGATT  CTAAGGGAAA  ATTAATTAAT   4140
4141    AGCGACGATT  TACAGAAGCA  AGGTTATTCA  CTCACATATA  TTGATTTATG  TACTGTTTCC   4200
4201    ATTAAAAAAG  GTAATTCAAA  TGAAATTGTT  AAATGTAATT  AATTTTGTTT  TCTTGATGTT   4260
4261    TGTTTCATCA  TCTTCTTTTG  CTCAGGTAAT  TGAAATGAAT  AATTCGCCTC  TGCGCGATTT   4320
4321    TGTAACTTGG  TATTCAAAGC  AATCAGGCGA  ATCCGTTATT  GTTTCTCCCG  ATGTAAAAGG   4380
4381    TACTGTTACT  GTATATTCAT  CTGACGTTAA  ACCTGAAAAT  CTACGCAATT  TCTTTATTTC   4440
4441    TGTTTTACGT  GCTAATAATT  TTGATATGGT  TGGTTCAATT  CCTTCCATAA  TTCAGAAGTA   4500
4501    TAATCCAAAC  AATCAGGATT  ATATTGATGA  ATTGCCATCA  TCTGATAATC  AGGAATATGA   4560
4561    TGATAATTCC  GCTCCTTCTG  GTGGTTTCTT  TGTTCCGCAA  AATGATAATG  TTACTCAAAC   4620
4621    TTTTAAAATT  AATAACGTTC  GGGCAAAGGA  TTTAATACGA  GTTGTCGAAT  TGTTTGTAAA   4680
4681    GTCTAATACT  TCTAAATCCT  CAAATGTATT  ATCTATTGAC  GGCTCTAATC  TATTAGTTGT   4740
4741    TAGTGCACCT  AAAGATATTT  TAGATAACCT  TCCTCAATTC  CTTTCTACTG  TTGATTTGCC   4800
4801    AACTGACCAG  ATATTGATTG  AGGGTTTGAT  ATTTGAGGTT  CAGCAAGGTG  ATGCTTTAGA   4860
4861    TTTTTCATTT  GCTGCTGGCT  CTCAGCGTGG  CACTGTTGCA  GGCGGTGTTA  ATACTGACCG   4920
4921    CCTCACCTCT  GTTTTATCTT  CTGCTGGTGG  TTCGTTCGGT  ATTTTTAATG  GCGATGTTTT   4980
4981    AGGGCTATCA  GTTCGCGCAT  TAAAGACTAA  TAGCCATTCA  AAATATTGT   CTGTGCCACG   5040
5041    TATTCTTACG  CTTTCAGGTC  AGAAGGGTTC  TATCTCTGTT  GGCCAGAATG  TCCCTTTTAT   5100
5101    TACTGGTCGT  GTGACTGGTG  AATCTGCCAA  TGTAAATAAT  CCATTTCAGA  CGATTGAGCG   5160
5161    TCAAAATGTA  GGTATTTCCA  TGAGCGTTTT  TCCTGTTGCA  ATGGCTGGCG  GTAATATTGT   5220
5221    TCTGGATATT  ACCAGCAAGG  CCGATAGTTT  GAGTTCTTCT  ACTCAGGCAA  GTGATGTTAT   5280
5281    TACTAATCAA  AGAAGTATTG  CTACAACGGT  TAATTTGCGT  GATGGACAGA  CTCTTTTACT   5340
5341    CGGTGGCCTC  ACTGATTATA  AAAACACTTC  TCAAGATTCT  GGCGTACCGT  TCCTGTCTAA   5400
5401    AATCCCTTTA  ATCGGCCTCC  TGTTTAGCTC  CCGCTCTGAT  TCCAACGAGG  AAAGCACGTT   5460
5461    ATACGTGCTC  GTCAAAGCAA  CCATAGTACG  CGCCCTGTAG  CGGCGCATTA  AGCGCGGCGG   5520
5521    GTGTGGTGGT  TACGCGCAGC  GTGACCGCTA  CACTTGCCAG  CGCCCTAGCG  CCCGCTCCTT   5580
5581    TCGCTTTCTT  CCCTTCCTTT  CTCGCCACGT  TCGCCGGCTT  TCCCCGTCAA  GCTCTAAATC   5640
5641    GGGGGCTCCC  TTTAGGGTTC  CGATTTAGTG  CTTTACGGCA  CCTCGACCCC  AAAAAACTTG   5700
5701    ATTTGGGTGA  TGGTTCACGT  AGTGGGCCAT  CGCCCTGATA  GACGGTTTTT  CGCCCTTTGA   5760
5761    CGTTGGAGTC  CACGTTCTTT  AATAGTGGAC  TCTTGTTCCA  AACTGGAACA  ACACTCAACC   5820
5821    CTATCTCGGG  CTATTCTTTT  GATTTATAAG  GGATTTTGCC  GATTTCGGAA  CCACCATCAA   5880
5881    ACAGGATTTT  CGCCTGCTGG  GGCAAACCAG  CGTGGACCGC  TTGCTGCAAC  TCTCTCAGGG   5940
5941    CCAGGCGGTG  AAGGGCAATC  AGCTGTTGCC  CGTCTCGCTG  GTGAAAAGAA  AAACCACCCT   6000
        |    10     |    20     |    30     |    40     |    50     |    60
```

FIG. 2B

```
        |   10      |   20      |   30      |   40      |   50      |   60
6001    GGCGCCCAAT  ACGCAAACCG  CCTCTCCCCG  CGCGTTGGCC  GATTCATTAA  TGCAGCTGGC    6060
6061    ACGACAGGTT  TCCCGACTGG  AAAGCGGGCA  GTGAGCGCAA  CGCAATTAAT  GTGAGTTAGC    6120
6121    TCACTCATTA  GGCACCCCAG  GCTTTACACT  TTATGCTTCC  GGCTCGTATG  TTGTGTGGAA    6180
6181    TTGTGAGCGG  ATAACAATTT  CACACGCGTC  ACTTGGCACT  GGCCGTCGTT  TTACAACGTC    6240
6241    GTGACTGGGA  AAACCCTGGC  GTTACCCAAG  CTTTGTACAT  GGAGAAAATA  AAGTGAAACA    6300
6301    AAGCACTATT  GCACTGGCAC  TCTTACCGTT  ACCGTTACTG  TTTACCCCTG  TGACAAAAGC    6360
6361    CGCCCAGGTC  CAGCTGCTCG  AGTCAGGCCT  ATTGTGCCCA  GGGGATTGTA  CTACTGGATC    6420
6421    CTAGGCTGAA  GGCGATGACC  CTGCTAAGGC  TGCATTCAAT  AGTTTACAGG  CAAGTGCTAC    6480
6481    TGAGTACATT  GGCTACGCTT  GGGCTATGGT  AGTAGTTATA  GTTGGTGCTA  CCATAGGGAT    6540
6541    TAAATTATTC  AAAAAGTTTA  CGAGCAAGGC  TTCTTAAGCA  ATAGCGAAGA  GGCCCGCACC    6600
6601    GATCGCCCTT  CCCAACAGTT  GCGCAGCCTG  AATGGCGAAT  GGCGCTTTGC  CTGGTTTCCG    6660
6661    GCACCAGAAG  CGGTGCCGGA  AAGCTGGCTG  GAGTGCGATC  TTCCTGAGGC  CGATACGGTC    6720
6721    GTCGTCCCCT  CAAACTGGCA  GATGCACGGT  TACGATGCGC  CCATCTACAC  CAACGTAACC    6780
6781    TATCCCATTA  CGGTCAATCC  GCCGTTTGTT  CCCACGGAGA  ATCCGACGGG  TTGTTACTCG    6840
6841    CTCACATTTA  ATGTTGATGA  AAGCTGGCTA  CAGGAAGGCC  AGACGCGAAT  TATTTTTGAT    6900
6901    GGCGTTCCTA  TTGGTTAAAA  AATGAGCTGA  TTTAACAAAA  ATTTAACGCG  AATTTTAACA    6960
6961    AAATATTAAC  GTTTACAATT  TAAATATTTG  CTTATACAAT  CTTCCTGTTT  TTGGGGCTTT    7020
7021    TCTGATTATC  AACCGGGGTA  CATATGATTG  ACATGCTAGT  TTTACGATTA  CCGTTCATCG    7080
7081    ATTCTCTTGT  TTGCTCCAGA  CTCTCAGGCA  ATGACCTGAT  AGCCTTTGTA  GATCTCTCAA    7140
7141    AAATAGCTAC  CCTCTCCGGC  ATTAATTTAT  CAGCTAGAAC  GGTTGAATAT  CATATTGATG    7200
7201    GTGATTTGAC  TGTCTCCGGC  CTTTCTCACC  CTTTTGAATC  TTTACCTACA  CATTACTCAG    7260
7261    GCATTGCATT  TAAAATATAT  GAGGGTTCTA  AAAATTTTTA  TCCTTGCGTT  GAAATAAAGG    7320
7321    CTTCTCCCGC  AAAAGTATTA  CAGGGTCATA  ATGTTTTTGG  TACAACCGAT  TTAGCTTTAT    7380
7381    GCTCTGAGGC  TTTATTGCTT  AATTTTGCTA  ATTCTTTGCC  TTGCCTGTAT  GATTTATTGG    7440
7441    ACGTT                                                                    7445
        |   10      |   20      |   30      |   40      |   50      |   60
```

FIG. 2C

```
        |   10        |   20        |   30        |   40        |   50        |   60
   1  AATGCTACTA CTATTAGTAG AATTGATGCC ACCTTTTCAG CTCGCGCCCC AAATGAAAAT    60
  61  ATAGCTAAAC AGGTTATTGA CCATTTGCGA AATGTATCTA ATGGTCAAAC TAAATCTACT   120
 121  CGTTCGCAGA ATTGGGAATC AACTGTTACA TGGAATGAAA CTTCCAGACA CCGTACTTTA   180
 181  GTTGCATATT TAAAACATGT TGAGCTACAG CACCAGATTC AGCAATTAAG CTCTAAGCCA   240
 241  TCCGCAAAAA TGACCTCTTA TCAAAAGGAG CAATTAAAGG TACTCTCTAA TCCTGACCTG   300
 301  TTGGAGTTTG CTTCCGGTCT GGTTCGCTTT GAAGCTCGAA TTAAAACGCG ATATTTGAAG   360
 361  TCTTTCGGGC TTCCTCTTAA TCTTTTTGAT GCAATCCGCT TTGCTTCTGA CTATAATAGT   420
 421  CAGGGTAAAG ACCTGATTTT TGATTTATGG TCATTCTCGT TTTCTGAACT GTTTAAAGCA   480
 481  TTTGAGGGGG ATTCAATGAA TATTTATGAC GATTCCGCAG TATTGGACGC TATCCAGTCT   540
 541  AAACATTTTA CTATTACCCC CTCTGGCAAA ACTTCTTTTG CAAAAGCCTC TCGCTATTTT   600
 601  GGTTTTTATC GTCGTCTGGT AAACGAGGGT TATGATAGTG TTGCTCTTAC TATGCCTCGT   660
 661  AATTCCTTTT GGCGTTATGT ATCTGCATTA GTTGAATGTG GTATTCCTAA ATCTCAACTG   720
 721  ATGAATCTTT CTACCTGTAA TAATGTTGTT CCGTTAGTTC GTTTTATTAA CGTAGATTTT   780
 781  TCTTCCCAAC GTCCTGACTG GTATAATGAG CCAGTTCTTA AAATCGCATA AGGTAATTCA   840
 841  CAATGATTAA AGTTGAAATT AAACCATCTC AAGCCCAATT TACTACTCGT TCTGGTGTTT   900
 901  CTCGTCAGGG CAAGCCTTAT TCACTGAATG AGCAGCTTTG TTACGTTGAT TTGGGTAATG   960
 961  AATATCCGGT TCTTGTCAAG ATTACTCTTG ATGAAGGTCA GCCAGCCTAT GCGCCTGGTC  1020
1021  TGTACACCGT TCATCTGTCC TCTTTCAAAG TTGGTCAGTT CGGTTCCCTT ATGATTGACC  1080
1081  GTCTGCGCCT CGTTCCGGCT AAGTAACATG GAGCAGGTCG CGGATTTCGA CACAATTTAT  1140
1141  CAGGCGATGA TACAAATCTC CGTTGTACTT TGTTTCGCGC TTGGTATAAT CGCTGGGGGT  1200
1201  CAAAGATGAG TGTTTTAGTG TATTCTTTCG CCTCTTTCGT TTTAGGTTGG TGCCTTCGTA  1260
1261  GTGGCATTAC GTATTTTACC CGTTTAATGG AAACTTCCTC ATGAAAAAGT CTTTAGTCCT  1320
1321  CAAAGCCTCT GTAGCCGTTG CTACCCTCGT TCCGATGCTG TCTTTCGCTG CTGAGGGTGA  1380
1381  CGATCCCGCA AAAGCGGCCT TTAACTCCCT GCAAGCCTCA GCGACCGAAT ATATCGGTTA  1440
1441  TGCGTGGGCG ATGGTTGTTG TCATTGTCGG CGCAACTATC GGTATCAAGC TGTTTAAGAA  1500
1501  ATTCACCTCG AAAGCAAGCT GATAAACCGA TACAATTAAA GGCTCCTTTT GGAGCCTTTT  1560
1561  TTTTTGGAGA TTTTCAACGT GAAAAAATTA TTATTCGCAA TTCCTTTAGT TGTTCCTTTC  1620
1621  TATTCTCACT CCGCTGAAAC TGTTGAAAGT TGTTTAGCAA AACCCCATAC AGAAAATTCA  1680
1681  TTTACTAACG TCTGGAAAGA CGACAAAACT TTAGATCGTT ACGCTAACTA TGAGGGTTGT  1740
1741  CTGTGGAATG CTACAGGCGT TGTAGTTTGT ACTGGTGACG AAACTCAGTG TTACGGTACA  1800
1801  TGGGTTCCTA TTGGGCTTGC TATCCCTGAA AATGAGGGTG GTGGCTCTGA GGGTGGCGGT  1860
1861  TCTGAGGGTG GCGGTTCTGA GGGTGGCGGT ACTAAACCTC CTGAGTACGG TGATACACCT  1920
1921  ATTCCGGGCT ATACTTATAT CAACCCTCTC GACGGCACTT ATCCGCCTGG TACTGAGCAA  1980
1981  AACCCCGCTA ATCCTAATCC TTCTCTTGAG GAGTCTCAGC CTCTTAATAC TTTCATGTTT  2040
2041  CAGAATAATA GGTTCCGAAA TAGGCAGGGG GCATTAACTG TTTATACGGG CACTGTTACT  2100
2101  CAAGGCACTG ACCCCGTTAA AACTTATTAC CAGTACACTC CTGTATCATC AAAAGCCATG  2160
2161  TATGACGCTT ACTGGAACGG TAAATTCAGA GACTGCGCTT TCCATTCTGG CTTTAATGAA  2220
2221  GATCCATTCG TTTGTGAATA TCAAGGCCAA TCGTCTGACC TGCCTCAACC TCCTGTCAAT  2280
2281  GCTGGCGGCG GCTCTGGTGG TGGTTCTGGT GGCGGCTCTG AGGGTGGTGG CTCTGAGGGT  2340
2341  GGCGGTTCTG AGGGTGGCGG CTCTGAGGGA GGCGGTTCCG GTGGTGGCTC TGGTTCCGGT  2400
2401  GATTTTGATT ATGAAAAGAT GGCAAACGCT AATAAGGGGG CTATGACCGA AAATGCCGAT  2460
2461  GAAAACGCGC TACAGTCTGA CGCTAAAGGC AAACTTGATT CTGTCGCTAC TGATTACGGT  2520
2521  GCTGCTATCG ATGGTTTCAT TGGTGACGTT TCCGGCCTTG CTAATGGTAA TGGTGCTACT  2580
2581  GGTGATTTTG CTGGCTCTAA TTCCCAAATG GCTCAAGTCG GTGACGGTGA TAATTCACCT  2640
2641  TTAATGAATA ATTTCCGTCA ATATTTACCT TCCCTCCCTC AATCGGTTGA ATGTCGCCCT  2700
2701  TTTGTCTTTA GCGCTGGTAA ACCATATGAA TTTTCTATTG ATTGTGACAA AATAAACTTA  2760
2761  TTCCGTGGTG TCTTTGCGTT TCTTTTATAT GTTGCCACCT TTATGTATGT ATTTTCTACG  2820
2821  TTTGCTAACA TACTGCGTAA TAAGGAGTCT TAATCATGCC AGTTCTTTTG GGTATTCCGT  2880
2881  TATTATTGCG TTTCCTCGGT TTCCTTCTGG TAACTTTGTT CGGCTATCTG CTTACTTTTC  2940
2941  TTAAAAAGGG CTTCGGTAAG ATAGCTATTG CTATTTCATT GTTTCTTGCT CTTATTATTG  3000
        |   10        |   20        |   30        |   40        |   50        |   60
```

FIG. 3A

```
       |  10       |  20       |  30       |  40       |  50       |  60
3001   GGCTTAACTC  AATTCTTGTG  GGTTATCTCT  CTGATATTAG  CGCTCAATTA  CCCTCTGACT  3060
3061   TTGTTCAGGG  TGTTCAGTTA  ATTCTCCCGT  CTAATGCGCT  TCCCTGTTTT  TATGTTATTC  3120
3121   TCTCTGTAAA  GGCTGCTATT  TTCATTTTTG  ACGTTAAACA  AAAAATCGTT  TCTTATTTGG  3180
3181   ATTGGGATAA  ATAATATGGC  TGTTTATTTT  GTAACTGGCA  AATTAGGCTC  TGGAAAGACG  3240
3241   CTCGTTAGCG  TTGGTAAGAT  TCAGGATAAA  ATTGTAGCTG  GGTGCAAAAT  AGCAACTAAT  3300
3301   CTTGATTTAA  GGCTTCAAAA  CCTCCCGCAA  GTCGGGAGGT  TCGCTAAAAC  GCCTCGCGTT  3360
3361   CTTAGAATAC  CGGATAAGCC  TTCTATATCT  GATTTGCTTG  CTATTGGGCG  CGGTAATGAT  3420
3421   TCCTACGATG  AAAATAAAAA  CGGCTTGCTT  GTTCTCGATG  AGTGCGGTAC  TTGGTTTAAT  3480
3481   ACCCGTTCTT  GGAATGATAA  GGAAAGACAG  CCGATTATTG  ATTGGTTTCT  ACATGCTCGT  3540
3541   AAATTAGGAT  GGGATATTAT  TTTTCTTGTT  CAGGACTTAT  CTATTGTTGA  TAAACAGGCG  3600
3601   CGTTCTGCAT  TAGCTGAACA  TGTTGTTTAT  TGTCGTCGTC  TGGACAGAAT  TACTTTACCT  3660
3661   TTTGTCGGTA  CTTTATATTC  TCTTATTACT  GGCTCGAAAA  TGCCTCTGCC  TAAATTACAT  3720
3721   GTTGGCGTTG  TTAAATATGG  CGATTCTCAA  TTAAGCCCTA  CTGTTGAGCG  TTGGCTTTAT  3780
3781   ACTGGTAAGA  ATTTGTATAA  CGCATATGAT  ACTAAACAGG  CTTTTTCTAG  TAATTATGAT  3840
3841   TCCGGTGTTT  ATTCTTATTT  AACGCCTTAT  TTATCACACG  GTCGGTATTT  CAAACCATTA  3900
3901   AATTTAGGTC  AGAAGATGAA  GCTTACTAAA  ATATATTTGA  AAAAGTTTTC  ACGCGTTCTT  3960
3961   TGTCTTGCGA  TTGGATTTGC  ATCAGCATTT  ACATATAGTT  ATATAACCCA  ACCTAAGCCG  4020
4021   GAGGTTAAAA  AGGTAGTCTC  TCAGACCTAT  GATTTTGATA  AATTCACTAT  TGACTCTTCT  4080
4081   CAGCGTCTTA  ATCTAAGCTA  TCGCTATGTT  TTCAAGGATT  CTAAGGGAAA  ATTAATTAAT  4140
4141   AGCGACGATT  TACAGAAGCA  AGGTTATTCA  CTCACATATA  TTGATTTATG  TACTGTTTCC  4200
4201   ATTAAAAAAG  GTAATTCAAA  TGAAATTGTT  AAATGTAATT  AATTTTGTTT  TCTTGATGTT  4260
4261   TGTTTCATCA  TCTTCTTTTG  CTCAGGTAAT  TGAAATGAAT  AATTCGCCTC  TGCGCGATTT  4320
4321   TGTAACTTGG  TATTCAAAGC  AATCAGGCGA  ATCCGTTATT  GTTTCTCCCG  ATGTAAAAGG  4380
4381   TACTGTTACT  GTATATTCAT  CTGACGTTAA  ACCTGAAAAT  CTACGCAATT  TCTTTATTTC  4440
4441   TGTTTTACGT  GCTAATAATT  TTGATATGGT  TGGTTCAATT  CCTTCCATAA  TTCAGAAGTA  4500
4501   TAATCCAAAC  AATCAGGATT  ATATTGATGA  ATTGCCATCA  TCTGATAATC  AGGAATATGA  4560
4561   TGATAATTCC  GCTCCTTCTG  GTGGTTTCTT  TGTTCCGCAA  AATGATAATG  TTACTCAAAC  4620
4621   TTTTAAAATT  AATAACGTTC  GGGCAAAGGA  TTTAATACGA  GTTGTCGAAT  TGTTTGTAAA  4680
4681   GTCTAATACT  TCTAAATCCT  CAAATGTATT  ATCTATTGAC  GGCTCTAATC  TATTAGTTGT  4740
4741   TAGTGCACCT  AAAGATATTT  TAGATAACCT  TCCTCAATTC  CTTTCTACTG  TTGATTTGCC  4800
4801   AACTGACCAG  ATATTGATTG  AGGGTTTGAT  ATTTGAGGTT  CAGCAAGGTG  ATGCTTTAGA  4860
4861   TTTTTCATTT  GCTGCTGGCT  CTCAGCGTGG  CACTGTTGCA  GGCGGTGTTA  ATACTGACCG  4920
4921   CCTCACCTCT  GTTTTATCTT  CTGCTGGTGG  TTCGTTCGGT  ATTTTTAATG  GCGATGTTTT  4980
4981   AGGGCTATCA  GTTCGCGCAT  TAAAGACTAA  TAGCCATTCA  AAAATATTGT  CTGTGCCACG  5040
5041   TATTCTTACG  CTTTCAGGTC  AGAAGGGTTC  TATCTCTGTT  GGCCAGAATG  TCCCTTTTAT  5100
5101   TACTGGTCGT  GTGACTGGTG  AATCTGCCAA  TGTAAATAAT  CCATTTCAGA  CGATTGAGCG  5160
5161   TCAAAATGTA  GGTATTTCCA  TGAGCGTTTT  TCCTGTTGCA  ATGGCTGGCG  GTAATATTGT  5220
5221   TCTGGATATT  ACCAGCAAGG  CCGATAGTTT  GAGTTCTTCT  ACTCAGGCAA  GTGATGTTAT  5280
5281   TACTAATCAA  AGAAGTATTG  CTACAACGGT  TAATTTGCGT  GATGGACAGA  CTCTTTTACT  5340
5341   CGGTGGCCTC  ACTGATTATA  AAAACACTTC  TCAAGATTCT  GGCGTACCGT  TCCTGTCTAA  5400
5401   AATCCCTTTA  ATCGGCCTCC  TGTTTAGCTC  CCGCTCTGAT  TCCAACGAGG  AAAGCACGTT  5460
5461   ATACGTGCTC  GTCAAAGCAA  CCATAGTACG  CGCCCTGTAG  CGGCGCATTA  AGCGCGGCGG  5520
5521   GTGTGGTGGT  TACGCGCAGC  GTGACCGCTA  CACTTGCCAG  CGCCCTAGCG  CCCGCTCCTT  5580
5581   TCGCTTTCTT  CCCTTCCTTT  CTCGCCACGT  TCGCCGGCTT  TCCCCGTCAA  GCTCTAAATC  5640
5641   GGGGGCTCCC  TTTAGGGTTC  CGATTTAGTG  CTTTACGGCA  CCTCGACCCC  AAAAAACTTG  5700
       |  10       |  20       |  30       |  40       |  50       |  60
```

FIG. 3B

```
        |   10       |   20       |   30       |   40       |   50       |   60
5701  ATTTGGGTGA TGGTTCACGT AGTGGGCCAT CGCCCTGATA GACGGTTTTT CGCCCTTTGA  5760
5761  CGTTGGAGTC CACGTTCTTT AATAGTGGAC TCTTGTTCCA AACTGGAACA ACACTCAACC  5820
5821  CTATCTCGGG CTATTCTTTT GATTTATAAG GGATTTTGCC GATTTCGGAA CCACCATCAA  5880
5881  ACAGGATTTT CGCCTGCTGG GGCAAACCAG CGTGGACCGC TTGCTGCAAC TCTCTCAGGG  5940
5941  CCAGGCGGTG AAGGGCAATC AGCTGTTGCC CGTCTCGCTG GTGAAAAGAA AAACCACCCT  6000
6001  GGCGCCCAAT ACGCAAACCG CCTCTCCCCG CGCGTTGGCC GATTCATTAA TGCAGCTGGC  6060
6061  ACGACAGGTT TCCCGACTGG AAAGCGGGCA GTGAGCGCAA CGCAATTAAT GTGAGTTAGC  6120
6121  TCACTCATTA GGCACCCCAG GCTTTACACT TTATGCTTCC GGCTCGTATG TTGTGTGGAA  6180
6181  TTGTGAGCGG ATAACAATTT CACACGCCAA GGAGACAGTC ATAATGAAAT ACCTATTGCC  6240
6241  TACGGCAGCC GCTGGATTGT TATTACTCGC TGCCCAACCA GCCATGGCCG AGCTCGTGAT  6300
6301  GACCCAGACT CCAGATATCC AACAGGAATG AGTGTTAATT CTAGAACGCG TCACTTGGCA  6360
6361  CTGGCCGTCG TTTTACAACG TCGTGACTGG GAAAACCCTG GCGTTACCCA AGCTTAATCG  6420
6421  CCTTGCAGAA TTCCCTTTCG CCAGCTGGCG TAATAGCGAA GAGGCCCGCA CCGATCGCCC  6480
6481  TTCCCAACAG TTGCGCAGCC TGAATGGCGA ATGGCGCTTT GCCTGGTTTC CGGCACCAGA  6540
6541  AGCGGTGCCG GAAAGCTGGC TGGAGTGCGA TCTTCCTGAG GCCGATACGG TCGTCGTCCC  6600
6601  CTCAAACTGG CAGATGCACG GTTACGATGC GCCCATCTAC ACCAACGTAA CCTATCCCAT  6660
6661  TACGGTCAAT CCGCCGTTTG TTCCCACGGA GAATCCGACG GGTTGTTACT CGCTCACATT  6720
6721  TAATGTTGAT GAAAGCTGGC TACAGGAAGG CCAGACGCGA ATTATTTTTG ATGGCGTTCC  6780
6781  TATTGGTTAA AAAATGAGCT GATTTAACAA AAATTTAACG CGAATTTTAA CAAAATATTA  6840
6841  ACGTTTACAA TTTAAATATT TGCTTATACA ATCTTCCTGT TTTTGGGGCT TTTCTGATTA  6900
6901  TCAACCGGGG TACATATGAT TGACATGCTA GTTTTACGAT TACCGTTCAT CGATTCTCTT  6960
6961  GTTTGCTCCA GACTCTCAGG CAATGACCTG ATAGCCTTTG TAGATCTCTC AAAAATAGCT  7020
7021  ACCCTCTCCG GCATTAATTT ATCAGCTAGA ACGGTTGAAT ATCATATTGA TGGTGATTTG  7080
7081  ACTGTCTCCG GCCTTTCTCA CCCTTTTGAA TCTTTACCTA CACATTACTC AGGCATTGCA  7140
7141  TTTAAAATAT ATGAGGGTTC TAAAAATTTT TATCCTTGCG TTGAAATAAA GGCTTCTCCC  7200
7201  GCAAAAGTAT TACAGGGTCA TAATGTTTTT GGTACAACCG ATTTAGCTTT ATGCTCTGAG  7260
7261  GCTTTATTGC TTAATTTTGC TAATTCTTTG CCTTGCCTGT ATGATTTATT GGATGTT     7317
        |   10       |   20       |   30       |   40       |   50       |   60
```

FIG. 3C

```
         |   10       |   20       |   30       |   40       |   50       |   60
   1   AATGCTACTA CTATTAGTAG AATTGATGCC ACCTTTTCAG CTCGCGCCCC AAATGAAAAT    60
  61   ATAGCTAAAC AGGTTATTGA CCATTTGCGA AATGTATCTA ATGGTCAAAC TAAATCTACT   120
 121   CGTTCGCAGA ATTGGGAATC AACTGTTACA TGGAATGAAA CTTCCAGACA CCGTACTTTA   180
 181   GTTGCATATT TAAAACATGT TGAGCTACAG CACCAGATTC AGCAATTAAG CTCTAAGCCA   240
 241   TCCGCAAAAA TGACCTCTTA TCAAAAGGAG CAATTAAAGG TACTCTCTAA TCCTGACCTG   300
 301   TTGGAGTTTG CTTCCGGTCT GGTTCGCTTT GAAGCTCGAA TTAAAACGCG ATATTTGAAG   360
 361   TCTTTCGGGC TTCCTCTTAA TCTTTTTGAT GCAATCCGCT TGCTTCTGA CTATAATAGT    420
 421   CAGGGTAAAG ACCTGATTTT TGATTTATGG TCATTCTCGT TTTCTGAACT GTTTAAAGCA   480
 481   TTTGAGGGGG ATTCAATGAA TATTTATGAC GATTCCGCAG TATTGGACGC TATCCAGTCT   540
 541   AAACATTTTA CTATTACCCC CTCTGGCAAA ACTTCTTTTG CAAAAGCCTC TCGCTATTTT   600
 601   GGTTTTTATC GTCGTCTGGT AAACGAGGGT TATGATAGTG TTGCTCTTAC TATGCCTCGT   660
 661   AATTCCTTTT GGCGTTATGT ATCTGCATTA GTTGAATGTG GTATTCCTAA ATCTCAACTG   720
 721   ATGAATCTTT CTACCTGTAA TAATGTTGTT CCGTTAGTTC GTTTTATTAA CGTAGATTTT   780
 781   TCTTCCCAAC GTCCTGACTG GTATAATGAG CCAGTTCTTA AAATCGCATA AGGTAATTCA   840
 841   CAATGATTAA AGTTGAAATT AAACCATCTC AAGCCCAATT TACTACTCGT TCTGGTGTTT   900
 901   CTCGTCAGGG CAAGCCTTAT TCACTGAATG AGCAGCTTTG TTACGTTGAT TTGGGTAATG   960
 961   AATATCCGGT TCTTGTCAAG ATTACTCTTG ATGAAGGTCA GCCAGCCTAT GCGCCTGGTC  1020
1021   TGTACACCGT TCATCGTGCC TCTTTCAAAG TTGGTCAGTT CGGTTCCCTT ATGATTGACC  1080
1081   GTCTGCGCCT CGTTCCGGCT AAGTAACATG GAGCAGGTCG CGGATTTCGA CACAATTTAT  1140
1141   CAGGCGATGA TACAAATCTC CGTTGTACTT TGTTTCGCGC TTGGTATAAT CGCTGGGGGT  1200
1201   CAAAGATGAG TGTTTTAGTG TATTCTTTCG CCTCTTTCGT TTTAGGTTGG TGCCTTCGTA  1260
1261   GTGGCATTAC GTATTTTACC CGTTTAATGG AAACTTCCTC ATGAAAAGT CTTTAGTCCT    1320
1321   CAAAGCCTCT GTAGCCGTTG CTACCCTCGT TCCGATGCTG TCTTTCGCTG CTGAGGGTGA  1380
1381   CGATCCCGCA AAAGCGGCCT TTAACTCCCT GCAAGCCTCA GCGACCGAAT ATATCGGTTA  1440
1441   TGCGTGGGCG ATGGTTGTTG TCATTGTCGG CGCAACTATC GGTATCAAGC TGTTTAAGAA  1500
1501   ATTCACCTCG AAAGCAAGCT GATAAACCGA TACAATTAAA GGCTCCTTTT GGAGCCTTTT  1560
1561   TTTTTGGAGA TTTTCAACGT GAAAAAATTA TTATTCGCAA TTCCTTTAGT TGTTCCTTTC  1620
1621   TATTCTCACT CCGCTGAAAC TGTTGAAAGT TGTTTAGCAA AACCCCATAC AGAAAATTCA  1680
1681   TTTACTAACG TCTGGAAAGA CGACAAAACT TTAGATCGTT ACGCTAACTA TGAGGGTTGT  1740
1741   CTGTGGAATG CTACAGGCGT TGTAGTTTGT ACTGGTGACG AAACTCAGTG TTACGGTACA  1800
1801   TGGGTTCCTA TTGGGCTTGC TATCCCTGAA AATGAGGGTG GTGGCTCTGA GGGTGGCGGT  1860
1861   TCTGAGGGTG GCGGTTCTGA GGGTGGCGGT ACTAAACCTC CTGAGTACGG TGATACACCT  1920
1921   ATTCCGGGCT ATACTTATAT CAACCCTCTC GACGGCACTT ATCCGCCTGG TACTGAGCAA  1980
1981   AACCCCGCTA ATCCTAATCC TTCTCTTGAG GAGTCTCAGC CTCTTAATAC TTTCATGTTT  2040
2041   CAGAATAATA GGTTCCGAAA TAGGCAGGGG GCATTAACTG TTTATACGGG CACTGTTACT  2100
2101   CAAGGCACTG ACCCCGTTAA AACTTATTAC CAGTACACTC CTGTATCATC AAAAGCCATG  2160
2161   TATGACGCTT ACTGGAACGG TAAATTCAGA GACTGCGCTT TCCATTCTGG CTTTAATGAA  2220
2221   GATCCATTCG TTTGTGAATA TCAAGGCCAA TCGTCTGACC TGCCTCAACC TCCTGTCAAT  2280
2281   GCTGGCGGCG GCTCTGGTGG TGGTTCTGGT GGCGGCTCTG AGGGTGGTGG CTCTGAGGGT  2340
2341   GGCGGTTCTG AGGGTGGCGG CTCTGAGGGA GGCGGTTCCG GTGGTGGCTC TGGTTCCGGT  2400
2401   GATTTTGATT ATGAAAAGAT GGCAAACGCT AATAAGGGGG CTATGACCGA AAATGCCGAT  2460
2461   GAAAACGCGC TACAGTCTGA CGCTAAAGGC AAACTTGATT CTGTCGCTAC TGATTACGGT  2520
2521   GCTGCTATCG ATGGTTTCAT TGGTGACGTT TCCGGCCTTG CTAATGGTAA TGGTGCTACT  2580
2581   GGTGATTTTG CTGGCTCTAA TTCCCAAATG GCTCAAGTCG GTGACGGTGA TAATTCACCT  2640
2641   TTAATGAATA ATTTCCGTCA ATATTTACCT TCCCTCCCTC AATCGGTTGA ATGTCGCCCT  2700
2701   TTTGTCTTTA GCGCTGGTAA ACCATATGAA TTTTCTATTG ATTGTGACAA AATAAACTTA  2760
2761   TTCCGTGGTG TCTTTGCGTT TCTTTTATAT GTTGCCACCT TTATGTATGT ATTTTCTACG  2820
2821   TTTGCTAACA TACTGCGTAA TAAGGAGTCT TAATCATGCC AGTTCTTTTG GGTATTCCGT  2880
2881   TATTATTGCG TTTCCTCGGT TTCCTTCTGG TAACTTTGTT CGGCTATCTG CTTACTTTTC  2940
2941   TTAAAAGGG CTTCGGTAAG ATAGCTATTG CCTGTTTCTT GCTCTTATTA TTGGGCTTAA    3000
         |   10       |   20       |   30       |   40       |   50       |   60
```

FIG. 4A

```
      |   10       |   20       |   30       |   40       |   50       |   60
3001  CTCAATTCTT  GTGGGTTATC  TCTCTGATAT  TAGCGCTCAA  TTACCCTCTG  ACTTTGTTCA  3060
3061  GGGTGTTCAG  TTAATTCTCC  CGTCTAATGC  GCTTCCCTGT  TTTTATGTTA  TTCTCTCTGT  3120
3121  AAAGGCTGCT  ATTTTCATTT  TTGACGTTAA  ACAAAAAATC  GTTTCTTATT  TGGATTGGGA  3180
3181  TAAATAATAT  GGCTGTTTAT  TTTGTAACTG  GCAAATTAGG  CTCTGGAAAG  ACGCTCGTTA  3240
3241  GCGTTGGTAA  GATTCAGGAT  AAAATTGTAG  CTGGGTGCAA  AATAGCAACT  AATCTTGATT  3300
3301  TAAGGCTTCA  AAACCTCCCG  CAAGTCGGGA  GGTTCGCTAA  AACGCCTCGC  GTTCTTAGAA  3360
3361  TACCGGATAA  GCCTTCTATA  TCTGATTTGC  TTGCTATTGG  GCGCGGTAAT  GATTCCTACG  3420
3421  ATGAAAATAA  AAACGGCTTG  CTTGTTCTCG  ATGAGTGCGG  TACTTGGTTT  AATACCCGTT  3480
3481  CTTGGAATGA  TAAGGAAAGA  CAGCCGATTA  TTGATTGGTT  TCTACATGCT  CGTAAATTAG  3540
3541  GATGGGATAT  TATTTTTCTT  GTTCAGGACT  TATCTATTGT  TGATAAACAG  GCGCGTTCTG  3600
3601  CATTAGCTGA  ACATGTTGTT  TATTGTCGTC  GTCTGGACAG  AATTACTTTA  CCTTTTGTCG  3660
3661  GTACTTTATA  TTCTCTTATT  ACTGGCTCGA  AAATGCCTCT  GCCTAAATTA  CATGTTGGCG  3720
3721  TTGTTAAATA  TGGCGATTCT  CAATTAAGCC  CTACTGTTGA  GCGTTGGCTT  TATACTGGTA  3780
3781  AGAATTTGTA  TAACGCATAT  GATACTAAAC  AGGCTTTTTC  TAGTAATTAT  GATTCCGGTG  3840
3841  TTTATTCTTA  TTTAACGCCT  TATTTATCAC  ACGGTCGGTA  TTTCAAACCA  TTAAATTTAG  3900
3901  GTCAGAAGAT  GAAGCTTACT  AAAATATATT  TGAAAAGTT   TTCACGCGTT  CTTTGTCTTG  3960
3961  CGATTGGATT  TGCATCAGCA  TTTACATATA  GTTATATAAC  CCAACCTAAG  CCGGAGGTTA  4020
4021  AAAAGGTAGT  CTCTCAGACC  TATGATTTTG  ATAAATTCAC  TATTGACTCT  TCTCAGCGTC  4080
4081  TTAATCTAAG  CTATCGCTAT  GTTTTCAAGG  ATTCTAAGGG  AAAATTAATT  AATAGCGACG  4140
4141  ATTTACAGAA  GCAAGGTTAT  TCACTCACAT  ATATTGATTT  ATGTACTGTT  TCCATTAAAA  4200
4201  AAGGTAATTC  AAATGAAATT  GTTAAATGTA  ATTAATTTTG  TTTTCTTGAT  GTTTGTTTCA  4260
4261  TCATCTTCTT  TTGCTCAGGT  AATTGAAATG  AATAATTCGC  CTCTGCGCGA  TTTTGTAACT  4320
4321  TGGTATTCAA  AGCAATCAGG  CGAATCCGTT  ATTGTTTCTC  CCGATGTAAA  AGGTACTGTT  4380
4381  ACTGTATATT  CATCTGACGT  TAAACCTGAA  AATCTACGCA  ATTTCTTTAT  TTCTGTTTTA  4440
4441  CGTGCTAATA  ATTTTGATAT  GGTTGGTTCA  ATTCCTTCCA  TAATTCAGAA  GTATAATCCA  4500
4501  AACAATCAGG  ATTATATTGA  TGAATTGCCA  TCATCTGATA  ATCAGGAATA  TGATGATAAT  4560
4561  TCCGCTCCTT  CTGGTGGTTT  CTTTGTTCCG  CAAAATGATA  ATGTTACTCA  AACTTTTAAA  4620
4621  ATTAATAACG  TTCGGGCAAA  GGATTTAATA  CGAGTTGTCG  AATTGTTTGT  AAAGTCTAAT  4680
4681  ACTTCTAAAT  CCTCAAATGT  ATTATCTATT  GACGGCTCTA  ATCTATTAGT  TGTTAGTGCA  4740
4741  CCTAAAGATA  TTTTAGATAA  CCTTCCTCAA  TTCCTTTCTA  CTGTTGATTT  GCCAACTGAC  4800
4801  CAGATATTGA  TTGAGGGTTT  GATATTTGAG  GTTCAGCAAG  GTGATGCTTT  AGATTTTTCA  4860
4861  TTTGCTGCTG  GCTCTCAGCG  TGGCACTGTT  GCAGGCGGTG  TTAATACTGA  CCGCCTCACC  4920
4921  TCTGTTTTAT  CTTCTGCTGG  TGGTTCGTTC  GGTATTTTTA  ATGGCGATGT  TTTAGGGCTA  4980
4981  TCAGTTCGCG  CATTAAAGAC  TAATAGCCAT  TCAAAATATA  TGTCTGTGCC  ACGTATTCTT  5040
5041  ACGCTTTCAG  GTCAGAAGGG  TTCTATCTCT  GTTGGCCAGA  ATGTCCCTTT  TATTACTGGT  5100
5101  CGTGTGACTG  GTGAATCTGC  CAATGTAAAT  AATCCATTTC  AGACGATTGA  GCGTCAAAAT  5160
5161  GTAGGTATTT  CCATGAGCGT  TTTTCCTGTT  GCAATGGCTG  GCGGTAATAT  TGTTCTGGAT  5220
5221  ATTACCAGCA  AGGCCGATAG  TTTGAGTTCT  TCTACTCAGG  CAAGTGATGT  TATTACTAAT  5280
5281  CAAAGAAGTA  TTGCTACAAC  GGTTAATTTG  CGTGATGGAC  AGACTCTTTT  ACTCGGTGGC  5340
5341  CTCACTGATT  ATAAAAACAC  TTCTCAAGAT  TCTGGCGTAC  CGTTCCTGTC  TAAAATCCCT  5400
5401  TTAATCGGCC  TCCTGTTTAG  CTCCCGCTCT  GATTCCAACG  AGGAAAGCAC  GTTATACGTG  5460
5461  CTCGTCAAAG  CAACCATAGT  ACGCGCCCTG  TAGCGGCGCA  TTAAGCGCGG  CGGGTGTGGT  5520
5521  GGTTACGCGC  AGCGTGACCG  CTACACTTGC  CAGCGCCCTA  GCGCCCGCTC  CTTTCGCTTT  5580
5581  CTTCCCTTCC  TTTCTCGCCA  CGTTCGCCGG  CTTTCCCCGT  CAAGCTCTAA  ATCGGGGGCT  5640
5641  CCCTTTAGGG  TTCCGATTTA  GTGCTTTACG  GCACCTCGAC  CCCAAAAAAC  TTGATTTGGG  5700
5701  TGATGGTTCA  CGTAGTGGGC  CATCGCCCTG  ATAGACGGTT  TTTCGCCCTT  TGACGTTGGA  5760
5761  GTCCACGTTC  TTTAATAGTG  GACTCTTGTT  CCAAACTGGA  ACAACACTCA  ACCCTATCTC  5820
5821  GGGCTATTCT  TTTGATTTAT  AAGGGATTTT  GCCGATTTCG  GAACCACCAT  CAAACAGGAT  5880
5881  TTTCGCCTGC  TGGGGCAAAC  CAGCGTGGAC  CGCTTGCTGC  AACTCTCTCA  GGGCCAGGCG  5940
5941  GTGAAGGGCA  ATCAGCTGTT  GCCCGTCTCG  CTGGTGAAAA  GAAAAACCAC  CCTGGCGCCC  6000
      |   10       |   20       |   30       |   40       |   50       |   60
```

FIG. 4B

```
         |   10        |   20        |   30        |   40        |   50        |   60
6001  AATACGCAAA  CCGCCTCTCC  CCGCGCGTTG  GCCGATTCAT  TAATGCAGCT  GGCACGACAG  6060
6061  GTTTCCCGAC  TGGAAAGCGG  GCAGTGAGCG  CAACGCAATT  AATGTGAGTT  AGCTCACTCA  6120
6121  TTAGGCACCC  CAGGCTTTAC  ACTTTATGCT  TCCGGCTCGT  ATGTTGTGTG  GAATTGTGAG  6180
6181  CGGATAACAA  TTTCACACGC  CAAGGAGACA  GTCATAATGA  AATACCTATT  GCCTACGGCA  6240
6241  GCCGCTGGAT  TGTTATTACT  CGCTGCCCAA  CCAGCCATGG  CCGAGCTCTT  CCCGCCATCT  6300
6301  GATGAGCAGT  TGAAATCTGG  AACTGCCTCT  GTTGTGTGCC  TGCTGAATAA  CTTCTATCCC  6360
6361  AGAGAGGCCA  AAGTACAGTG  GAAGGTGGAT  AACGCCCTCC  AATCGGGTAA  CTCCCAGGAG  6420
6421  AGTGTCACAG  AGCAGGACAG  CAAGGACAGC  ACCTACAGCC  TCAGCAGCAC  CCTGACGCTG  6480
6481  AGCAAAGCAG  ACTACGAGAA  ACACAAAGTC  TACGCCTGCG  AAGTCACCCA  TCAGGGCCTG  6540
6541  AGCTCGCCCG  TCACAAAGAG  CTTCAACAGG  GGAGAGTGTT  CTAGAACGCG  TCACTTGGCA  6600
6601  CTGGCCGTCG  TTTTACAACG  TCGTGACTGG  GAAAACCCTG  GCGTTACCCA  AGCTTAATCG  6660
6661  CCTTGCAGAA  TTCCCTTTCG  CCAGCTGGCG  TAATAGCGAA  GAGGCCCGCA  CCGATCGCCC  6720
6721  TTCCCAACAG  TTGCGCAGCC  TGAATGGCGA  ATGGCGCTTT  GCCTGGTTTC  CGGCACCAGA  6780
6781  AGCGGTGCCG  GAAAGCTGGC  TGGAGTGCGA  TCTTCCTGAG  GCCGATACGG  TCGTCGTCCC  6840
6841  CTCAAACTGG  CAGATGCACG  GTTACGATGC  GCCCATCTAC  ACCAACGTAA  CCTATCCCAT  6900
6901  TACGGTCAAT  CCGCCGTTTG  TTCCCACGGA  GAATCCGACG  GGTTGTTACT  CGCTCACATT  6960
6961  TAATGTTGAT  GAAAGCTGGC  TACAGGAAGG  CCAGACGCGA  ATTATTTTTG  ATGGCGTTCC  7020
7021  TATTGGTTAA  AAAATGAGCT  GATTTAACAA  AAATTTAACG  CGAATTTTAA  CAAAATATTA  7080
7081  ACGTTTACAA  TTTAAATATT  TGCTTATACA  ATCTTCCTGT  TTTTGGGGCT  TTTCTGATTA  7140
7141  TCAACCGGGG  TACATATGAT  TGACATGCTA  GTTTTACGAT  TACCGTTCAT  CGATTCTCTT  7200
7201  GTTTGCTCCA  GACTCTCAGG  CAATGACCTG  ATAGCCTTTG  TAGATCTCTC  AAAAATAGCT  7260
7261  ACCCTCTCCG  GCATTAATTT  ATCAGCTAGA  ACGGTTGAAT  ATCATATTGA  TGGTGATTTG  7320
7321  ACTGTCTCCG  GCCTTTCTCA  CCCTTTTGAA  TCTTTACCTA  CACATTACTC  AGGCATTGCA  7380
7381  TTTAAAATAT  ATGAGGGTTC  TAAAAATTTT  TATCCTTGCG  TTGAAATAAA  GGCTTCTCCC  7440
7441  GCAAAAGTAT  TACAGGGTCA  TAATGTTTTT  GGTACAACCG  ATTTAGCTTT  ATGCTCTGAG  7500
7501  GCTTTATTGC  TTAATTTTGC  TAATTCTTTG  CCTTGCCTGT  ATGATTTATT  GGATGTT     7557
         |   10        |   20        |   30        |   40        |   50        |   60
```

FIG. 4C

```
           |  10        |  20        |  30        |  40        |  50        |  60
    1   AATGCTACTA CTATTAGTAG AATTGATGCC ACCTTTTCAG CTCGCGCCCC AAATGAAAAT   60
   61   ATAGCTAAAC AGGTTATTGA CCATTTGCGA AATGTATCTA ATGGTCAAAC TAAATCTACT  120
  121   CGTTCGCAGA ATTGGGAATC AACTGTTACA TGGAATGAAA CTTCCAGACA CCGTACTTTA  180
  181   GTTGCATATT TAAAACATGT TGAGCTACAG CACCAGATTC AGCAATTAAG CTCTAAGCCA  240
  241   TCTGCAAAAA TGACCTCTTA TCAAAAGGAG CAATTAAAGG TACTCTCTAA TCCTGACCTG  300
  301   TTGGAGTTTG CTTCCGGTCT GGTTCGCTTT GAAGCTCGAA TTAAAACGCG ATATTTGAAG  360
  361   TCTTTCGGGC TTCCTCTTAA TCTTTTTGAT GCAATCCGCT TTGCTTCTGA CTATAATAGT  420
  421   CAGGGTAAAG ACCTGATTTT TGATTTATGG TCATTCTCGT TTTCTGAACT GTTTAAAGCA  480
  481   TTTGAGGGGG ATTCAATGAA TATTTATGAC GATTCCGCAG TATTGGACGC TATCCAGTCT  540
  541   AAACATTTTA CTATTACCCC CTCTGGCAAA ACTTCTTTTG CAAAAGCCTC TCGCTATTTT  600
  601   GGTTTTTATC GTCGTCTGGT AAACGAGGGT TATGATAGTG TTGCTCTTAC TATGCCTCGT  660
  661   AATTCCTTTT GGCGTTATGT ATCTGCATTA GTTGAATGTG GTATTCCTAA ATCTCAACTG  720
  721   ATGAATCTTT CTACCTGTAA TAATGTTGTT CCGTTAGTTC GTTTTATTAA CGTAGATTTT  780
  781   TCTTCCCAAC GTCCTGACTG GTATAATGAG CCAGTTCTTA AAATCGCATA AGGTAATTCA  840
  841   CAATGATTAA AGTTGAAATT AAACCATCTC AAGCCCAATT TACTACTCGT TCTGGTGTTT  900
  901   CTCGTCAGGG CAAGCCTTAT TCACTGAATG AGCAGCTTTG TTACGTTGAT TTGGGTAATG  960
  961   AATATCCGGT TCTTGTCAAG ATTACTCTTG ATGAAGGTCA GCCAGCCTAT GCGCCTGGTC 1020
 1021   TGTACACCGT TCATCTGTCC TCTTTCAAAG TTGGTCAGTT CGGTTCCCTT ATGATTGACC 1080
 1081   GTCTGCGCCT CGTTCCGGCT AAGTAACATG GAGCAGGTCG CGGATTTCGA CACAATTTAT 1140
 1141   CAGGCGATGA TACAAATCTC CGTTGTACTT TGTTTCGCGC TTGGTATAAT CGCTGGGGGT 1200
 1201   CAAAGATGAG TGTTTTAGTG TATTCTTTCG CCTCTTTCGT TTTAGGTTGG TGCCTTCGTA 1260
 1261   GTGGCATTAC GTATTTTACC CGTTTAATGG AAACTTCCTC ATGAAAAAGT CTTTAGTCCT 1320
 1321   CAAAGCCTCT GTAGCCGTTG CTACCCTCGT TCCGATGCTG TCTTTCGCTG CTGAGGGTGA 1380
 1381   CGATCCCGCA AAAGCGGCCT TTAACTCCCT GCAAGCCTCA GCGACCGAAT ATATCGGTTA 1440
 1441   TGCGTGGGCG ATGGTTGTTG TCATTGTCGG CGCAACTATC GGTATCAAGC TGTTTAAGAA 1500
 1501   ATTCACCTCG AAAGCAAGCT GATAAACCGA TACAATTAAA GGCTCCTTTT GGAGCCTTTT 1560
 1561   TTTTTGGAGA TTTTCAACGT GAAAAAATTA TTATTCGCAA TTCCTTTAGT TGTTCCTTTC 1620
 1621   TATTCTCACT CCGCTGAAAC TGTTGAAAGT TGTTTAGCAA AACCCCATAC AGAAAATTCA 1680
 1681   TTTACTAACG TCTGGAAAGA CGACAAAACT TTAGATCGTT ACGCTAACTA TGAGGGTTGT 1740
 1741   CTGTGGAATG CTACAGGCGT TGTAGTTTGT ACTGGTGACG AAACTCAGTG TTACGGTACA 1800
 1801   TGGGTTCCTA TTGGGCTTGC TATCCCTGAA AATGAGGGTG GTGGCTCTGA GGGTGGCGGT 1860
 1861   TCTGAGGGTG GCGGTTCTGA GGGTGGCGGT ACTAAACCTC CTGAGTACGG TGATACACCT 1920
 1921   ATTCCGGGCT ATACTTATAT CAACCCTCTC GACGGCACTT ATCCGCCTGG TACTGAGCAA 1980
 1981   AACCCCGCTA ATCCTAATCC TTCTCTTGAG GAGTCTCAGC CTCTTAATAC TTTCATGTTT 2040
 2041   CAGAATAATA GGTTCCGAAA TAGGCAGGGG GCATTAACTG TTTATACGGG CACTGTTACT 2100
 2101   CAAGGCACTG ACCCCGTTAA AACTTATTAC CAGTACACTC CTGTATCATC AAAAGCCATG 2160
 2161   TATGACGCTT ACTGGAACGG TAAATTCAGA GACTGCGCTT TCCATTCTGG CTTTAATGAA 2220
 2221   GATCCATTCG TTTGTGAATA TCAAGGCCAA TCGTCTGACC TGCCTCAACC TCCTGTCAAT 2280
 2281   GCTGGCGGCG GCTCTGGTGG TGGTTCTGGT GGCGGCTCTG AGGGTGGTGG CTCTGAGGGT 2340
 2341   GGCGGTTCTG AGGGTGGCGG CTCTGAGGGA GGCGGTTCCG GTGGTGGCTC TGGTTCCGGT 2400
 2401   GATTTTGATT ATGAAAAGAT GGCAAACGCT AATAAGGGGG CTATGACCGA AAATGCCGAT 2460
 2461   GAAAACGCGC TACAGTCTGA CGCTAAAGGC AAACTTGATT CTGTCGCTAC TGATTACGGT 2520
 2521   GCTGCTATCG ATGGTTTCAT TGGTGACGTT TCCGGCCTTG CTAATGGTAA TGGTGCTACT 2580
 2581   GGTGATTTTG CTGGCTCTAA TTCCCAAATG GCTCAAGTCG GTGACGGTGA TAATTCACCT 2640
 2641   TTAATGAATA ATTTCCGTCA ATATTTACCT TCCCTCCCTC AATCGGTTGA ATGTCGCCCT 2700
 2701   TTTGTCTTTA GCGCTGGTAA ACCATATGAA TTTTCTATTG ATTGTGACAA AATAAACTTA 2760
 2761   TTCCGTGGTG TCTTTGCGTT TCTTTTATAT GTTGCCACCT TTATGTATGT ATTTTCTACG 2820
 2821   TTTGCTAACA TACTGCGTAA TAAGGAGTCT TAATCATGCC AGTTCTTTTG GGTATTCCGT 2880
 2881   TATTATTGCG TTTCCTCGG TTCCTTCTGG TAACTTTGTT CGGCTATCTG CTTACTTTTC 2940
 2941   TTAAAAAGGG CTTCGGTAAG ATAGCTATTG CTATTTCATT GTTTCTTGCT GTTATTATTG 3000
           |  10        |  20        |  30        |  40        |  50        |  60
```

FIG. 5A

```
       |   10       |   20       |   30       |   40       |   50       |   60
3001   GGCTTAACTC AATTCTTGTG GGTTATCTCT CTGATATTAG CGCTCAATTA CCCTCTGACT   3060
3061   TTGTTCAGGG TGTTCAGTTA ATTCTCCCGT CTAATGCGCT TCCCTGTTTT TATGTTATTC   3120
3121   TCTCTGTAAA GGCTGCTATT TTCATTTTTG ACGTTAAACA AAAAATCGTT TCTTATTTGG   3180
3181   ATTGGGATAA ATAATATGGC TGTTTATTTT GTAACTGGCA AATTAGGCTC TGGAAAGACG   3240
3241   CTCGTTAGCG TTGGTAAGAT TCAGGATAAA ATTGTAGCTG GGTGCAAAAT AGCAACTAAT   3300
3301   CTTGATTTAA GGCTTCAAAA CCTCCCGCAA GTCGGGAGGT TCGCTAAAAC GCCTCGCGTT   3360
3361   CTTAGAATAC CGGATAAGCC TTCTATATCT GATTTGCTTG CTATTGGGCG CGGTAATGAT   3420
3421   TCCTACGATG AAAATAAAAA CGGCTTGCTT GTTCTCGATG AGTGCGGTAC TTGGTTTAAT   3480
3481   ACCCGTTCTT GGAATGATAA GGAAAGACAG CCGATTATTG ATTGGTTTCT ACATGCTCGT   3540
3541   AAATTAGGAT GGGATATTAT TTTTCTTGTT CAGGACTTAT CTATTGTTGA TAAACAGGCG   3600
3601   CGTTCTGCAT TAGCTGAACA TGTTGTTTAT TGTCGTCGTC TGGACAGAAT TACTTTACCT   3660
3661   TTTGTCGGTA CTTTATATTC TCTTATTACT GGCTCGAAAA TGCCTCTGCC TAAATTACAT   3720
3721   GTTGGCGTTG TTAAATATGG CGATTCTCAA TTAAGCCCTA CTGTTGAGCG TTGGCTTTAT   3780
3781   ACTGGTAAGA ATTTGTATAA CGCATATGAT ACTAAACAGG CTTTTTCTAG TAATTATGAT   3840
3841   TCCGGTGTTT ATTCTTATTT AACGCCTTAT TTATCACACG GTCGGTATTT CAAACCATTA   3900
3901   AATTTAGGTC AGAAGATGAA GCTTACTAAA ATATATTTGA AAAAGTTTTC ACGCGTTCTT   3960
3961   TGTCTTGCGA TTGGATTTGC ATCAGCATTT ACATATAGTT ATATAACCCA ACCTAAGCCG   4020
4021   GAGGTTAAAA AGGTAGTCTC TCAGACCTAT GATTTTGATA AATTCACTAT TGACTCTTCT   4080
4081   CAGCGTCTTA ATCTAAGCTA TCGCTATGTT TTCAAGGATT CTAAGGGAAA ATTAATTAAT   4140
4141   AGCGACGATT TACAGAAGCA AGGTTATTCA CTCACATATA TTGATTTATG TACTGTTTCC   4200
4201   ATTAAAAAAG GTAATTCAAA TGAAATTGTT AAATGTAATT AATTTTGTTT TCTTGATGTT   4260
4261   TGTTTCATCA TCTTCTTTTG CTCAGGTAAT TGAAATGAAT AATTCGCCTC TGCGCGATTT   4320
4321   TGTAACTTGG TATTCAAAGC AATCAGGCGA ATCCGTTATT GTTTCTCCCG ATGTAAAAGG   4380
4381   TACTGTTACT GTATATTCAT CTGACGTTAA ACCTGAAAAT CTACGCAATT TCTTTATTTC   4440
4441   TGTTTTACGT GCTAATAATT TTGATATGGT TGGTTCAATT CCTTCCATAA TTCAGAAGTA   4500
4501   TAATCCAAAC AATCAGGATT ATATTGATGA ATTGCCATCA TCTGATAATC AGGAATATGA   4560
4561   TGATAATTCC GCTCCTTCTG GTGGTTTCTT TGTTCCGCAA AATGATAATG TTACTCAAAC   4620
4621   TTTTAAAATT AATAACGTTC GGGCAAAGGA TTTAATACGA GTTGTCGAAT TGTTTGTAAA   4680
4681   GTCTAATACT TCTAAATCCT CAAATGTATT ATCTATTGAC GGCTCTAATC TATTAGTTGT   4740
4741   TAGTGCACCT AAAGATATTT TAGATAACCT TCCTCAATTC CTTTCTACTG TTGATTTGCC   4800
4801   AACTGACCAG ATATTGATTG AGGGTTTGAT ATTTGAGGTT CAGCAAGGTG ATGCTTTAGA   4860
4861   TTTTTCATTT GCTGCTGGCT CTCAGCGTGG CACTGTTGCA GGCGGTGTTA ATACTGACCG   4920
4921   CCTCACCTCT GTTTTATCTT CTGCTGGTGG TTCGTTCGGT ATTTTTAATG GCGATGTTTT   4980
4981   AGGGCTATCA GTTCGCGCAT TAAAGACTAA TAGCCATTCA AAAATATTGT CTGTGCCACG   5040
5041   TATTCTTACG CTTTCAGGTC AGAAGGGTTC TATCTCTGTT GGCCAGAATG TCCCTTTTAT   5100
5101   TACTGGTCGT GTGACTGGTG AATCTGCCAA TGTAAATAAT CCATTTCAGA CGATTGAGCG   5160
5161   TCAAAATGTA GGTATTTCCA TGAGCGTTTT TCCTGTTGCA ATGGCTGGCG GTAATATTGT   5220
5221   TCTGGATATT ACCAGCAAGG CCGATAGTTT GAGTTCTTCT ACTCAGGCAA GTGATGTTAT   5280
5281   TACTAATCAA AGAAGTATTG CTACAACGGT TAATTTGCGT GATGGACAGA CTCTTTTACT   5340
5341   CGGTGGCCTC ACTGATTATA AAAACACTTC TCAAGATTCT GGCGTACCGT TCCTGTCTAA   5400
5401   AATCCCTTTA ATCGGCCTCC TGTTTAGCTC CCGCTCTGAT TCCAACGAGG AAAGCACGTT   5460
5461   ATACGTGCTC GTCAAAGCAA CCATAGTACG CGCCCTGTAG CGGCGCATTA AGCGCGGCGG   5520
5521   GTGTGGTGGT TACGCGCAGC GTGACCGCTA CACTTGCCAG CGCCCTAGCG CCCGCTCCTT   5580
5581   TCGCTTTCTT CCCTTCCTTT CTCGCCACGT TCGCCGGCTT TCCCCGTCAA GCTCTAAATC   5640
5641   GGGGGCTCCC TTTAGGGTTC CGATTTAGTG CTTTACGGCA CCTCGACCCC AAAAAACTTG   5700
5701   ATTTGGGTGA TGGTTCACGT AGTGGGCCAT CGCCCTGATA GACGGTTTTT CGCCCTTTGA   5760
5761   CGTTGGAGTC CACGTTCTTT AATAGTGGAC TCTTGTTCCA AACTGGAACA ACACTCAACC   5820
5821   CTATCTCGGG CTATTCTTTT GATTTATAAG GGATTTTGCC GATTTCGGAA CCACCATCAA   5880
5881   ACAGGATTTT CGCCTGCTGG GGCAAACCAG CGTGGACCGC TTGCTGCAAC TCTCTCAGGG   5940
5941   CCAGGCGGTG AAGGGCAATC AGCTGTTGCC CGTCTCGCTG GTGAAAAGAA AAACCACCCT   6000
       |   10       |   20       |   30       |   40       |   50       |   60
```

FIG. 5B

```
     |   10       |   20       |   30       |   40       |   50       |   60
6001 GGCGCCCAAT ACGCAAACCG CCTCTCCCCG CGCGTTGGCC GATTCATTAA TGCAGCTGGC 6060
6061 ACGACAGGTT TCCCGACTGG AAAGCGGGCA GTGAGCGCAA CGCAATTAAT GTGAGTTAGC 6120
6121 TCACTCATTA GGCACCCCAG GCTTTACACT TTATGCTTCC GGCTCGTATG TTGTGTGGAA 6180
6181 TTGTGAGCGG ATAACAATTT CACACGCGTC ACTTGGCACT GGCCGTCGTT TTACAACGTC 6240
6241 GTGACTGGGA AAACCCTGGC GTTACCCAAG CTTTGTACAT GGAGAAAATA AAGTGAAACA 6300
6301 AAGCACTATT GCACTGGCAC TCTTACCGTT ACTGTTTACC CCTGTGGCAA AAGCCCAGGT 6360
6361 CCAGCTGCTC GAGTCGGTCT TCCCCCTGGC ACCCTCCTCC AAGAGCACCT CTGGGGGCAC 6420
6421 AGCGGCCCTG GGCTGCCTGG TCAAGACTAA TTCCCCGAAC CGGTGACGGT GTCGTGGAAC 6480
6481 TCAGGCGCCC TGACCAGCGG CGTGCACACC TTCCGGCTG TCCTACAGTC CTCAGGACTC 6540
6541 TACTCCCTCA GCAGCGTGGT GACCGTGCCC TCCAGCAGCT TGGGCACCCA GACCTACATC 6600
6601 TGCAACGTGA ATCACAAGCC CAGCAACACC AAGGTGGACA AGAAAGCAGA GCCCAAATCT 6660
6661 TGTACTAGTG GATCCTACCC GTACGACGTT CCGGACTACG CTTCTTAGGC TGAAGGCGAT 6720
6721 GACCCTGCTA AGGCTGCATT CAATAGTTTA CAGGCAAGTG CTACTGAGTA CATTGGCTAC 6780
6781 GCTTGGGCTA TGGTAGTAGT TATAGTTGGT GCTACCATAG GGATTAAATT ATTCAAAAAG 6840
6841 TTTACGAGCA AGGCTTCTTA AGCAATAGCG AAGAGGCCCG CACCGATCGC CCTTCCCAAC 6900
6901 AGTTGCGCAG CCTGAATGGC GAATGGCGCT TTGCCTGGTT TCCGGCACCA GAAGCGGTGC 6960
6961 CGGAAAGCTG GCTGGAGTGC GATCTTCCTG AGGCCGATAC GGTCGTCGTC CCCTCAAACT 7020
7021 GGCAGATGCA CGGTTACGAT GCGCCCATCT ACACCAACGT AACCTATCCC ATTACGGTCA 7080
7081 ATCCGCCGTT TGTTCCCACG GAGAATCCGA CGGGTTGTTA CTCGCTCACA TTTAATGTTG 7140
7141 ATGAAAGCTG GCTACAGGAA GGCCAGACGC GAATTATTTT TGATGGCGTT CCTATTGGTT 7200
7201 AAAAAATGAG CTGATTTAAC AAAAATTTAA CGCGAATTTT AACAAAATAT TAACGTTTAC 7260
7261 AATTTAAATA TTTGCTTATA CAATCTTCCT GTTTTTGGGG CTTTTCTGAT TATCAACCGG 7320
7321 GGTACATATG ATTGACATGC TAGTTTTACG ATTACCGTTC ATCGATTCTC TTGTTTGCTC 7380
7381 CAGACTCTCA GGCAATGACC TGATAGCCTT TGTAGATCTC TCAAAAATAG CTACCCTCTC 7440
7441 CGGCATTAAT TTATCAGCTA GAACGGTTGA ATATCATATT GATGGTGATT TGACTGTCTC 7500
7501 CGGCCTTTCT CACCCTTTTG AATCTTTACC TACACATTAC TCAGGCATTG CATTTAAAAT 7560
7561 ATATGAGGGT TCTAAAAATT TTTATCCTTG CGTTGAAATA AAGGCTTCTC CCGCAAAAGT 7620
7621 ATTACAGGGT CATAATGTTT TTGGTACAAC CGATTTAGCT TTATGCTCTG AGGCTTTATT 7680
7681 GCTTAATTTT GCTAATTCTT TGCCTTGCCT GTATGATTTA TTGGACGTT               7729
     |   10       |   20       |   30       |   40       |   50       |   60
```

FIG. 5C

```
      |   10       |   20       |   30       |   40       |   50       |   60
   1  AATGCTACTA  CTATTAGTAG  AATTGATGCC  ACCTTTTCAG  CTCGCGCCCC  AAATGAAAAT   60
  61  ATAGCTAAAC  AGGTTATTGA  CCATTTGCGA  AATGTATCTA  ATGGTCAAAC  TAAATCTACT  120
 121  CGTTCGCAGA  ATTGGGAATC  AACTGTTACA  TGGAATGAAA  CTTCCAGACA  CCGTACTTTA  180
 181  GTTGCATATT  TAAAACATGT  TGAGCTACAG  CACCAGATTC  AGCAATTAAG  CTCTAAGCCA  240
 241  TCTGCAAAAA  TGACCTCTTA  TCAAAAGGAG  CAATTAAAGG  TACTCTCTAA  TCCTGACCTG  300
 301  TTGGAGTTTG  CTTCCGGTCT  GGTTCGCTTT  GAAGCTCGAA  TTAAAACGCG  ATATTTGAAG  360
 361  TCTTTCGGGC  TTCCTCTTAA  TCTTTTTGAT  GCAATCCGCT  TTGCTTCTGA  CTATAATAGT  420
 421  CAGGGTAAAG  ACCTGATTTT  TGATTTATGG  TCATTCTCGT  TTTCTGAACT  GTTTAAAGCA  480
 481  TTTGAGGGGG  ATTCAATGAA  TATTTATGAC  GATTCCGCAG  TATTGGACGC  TATCCAGTCT  540
 541  AAACATTTTA  CTATTACCCC  CTCTGGCAAA  ACTTCTTTTG  CAAAAGCCTC  TCGCTATTTT  600
 601  GGTTTTTATC  GTCGTCTGGT  AAACGAGGGT  TATGATAGTG  TTGCTCTTAC  TATGCCTCGT  660
 661  AATTCCTTTT  GGCGTTATGT  ATCTGCATTA  GTTGAATGTG  GTATTCCTAA  ATCTCAACTG  720
 721  ATGAATCTTT  CTACCTGTAA  TAATGTTGTT  CCGTTAGTTC  GTTTTATTAA  CGTAGATTTT  780
 781  TCTTCCCAAC  GTCCTGACTG  GTATAATGAG  CCAGTTCTTA  AAATCGCATA  AGGTAATTCA  840
 841  CAATGATTAA  AGTTGAAATT  AAACCATCTC  AAGCCCAATT  TACTACTCGT  TCTGGTGTTT  900
 901  CTCGTCAGGG  CAAGCCTTAT  TCACTGAATG  AGCAGCTTTG  TTACGTTGAT  TTGGGTAATG  960
 961  AATATCCGGT  TCTTGTCAAG  ATTACTCTTG  ATGAAGGTCA  GCCAGCCTAT  GCGCCTGGTC 1020
1021  TGTACACCGT  TCATCTGTCC  TCTTTCAAAG  TTGGTCAGTT  CGGTTCCCTT  ATGATTGACC 1080
1081  GTCTGCGCCT  CGTTCCGGCT  AAGTAACATG  GAGCAGGTCG  CGGATTTCGA  CACAATTTAT 1140
1141  CAGGCGATGA  TACAAATCTC  CGTTGTACTT  TGTTTCGCGC  TTGGTATAAT  CGCTGGGGGT 1200
1201  CAAAGATGAG  TGTTTTAGTG  TATTCTTTCG  CCTCTTTCGT  TTTAGGTTGG  TGCCTTCGTA 1260
1261  GTGGCATTAC  GTATTTTACC  CGTTTAATGG  AAACTTCCTC  ATGAAAAAGT  CTTTAGTCCT 1320
1321  CAAAGCCTCT  GTAGCCGTTG  CTACCCTCGT  TCCGATGCTG  TCTTTCGCTG  CTGAGGGTGA 1380
1381  CGATCCCGCA  AAAGCGGCCT  TTAACTCCCT  GCAAGCCTCA  GCGACCGAAT  ATATCGGTTA 1440
1441  TGCGTGGGCG  ATGGTTGTTG  TCATTGTCGG  CGCAACTATC  GGTATCAAGC  TGTTTAAGAA 1500
1501  ATTCACCTCG  AAAGCAAGCT  GATAAACCGA  TACAATTAAA  GGCTCCTTTT  GGAGCCTTTT 1560
1561  TTTTTGGAGA  TTTTCAACGT  GAAAAAATTA  TTATTCGCAA  TTCCTTTAGT  TGTTCCTTTC 1620
1621  TATTCTCACT  CCGCTGAAAC  TGTTGAAAGT  TGTTTAGCAA  AACCCCATAC  AGAAAATTCA 1680
1681  TTTACTAACG  TCTGGAAAGA  CGACAAAACT  TTAGATCGTT  ACGCTAACTA  TGAGGGTTGT 1740
1741  CTGTGGAATG  CTACAGGCGT  TGTAGTTTGT  ACTGGTGACG  AAACTCAGTG  TTACGGTACA 1800
1801  TGGGTTCCTA  TTGGGCTTGC  TATCCCTGAA  AATGAGGGTG  GTGGCTCTGA  GGGTGGCGGT 1860
1861  TCTGAGGGTG  GCGGTTCTGA  GGGTGGCGGT  ACTAAACCTC  CTGAGTACGG  TGATACACCT 1920
1921  ATTCCGGGCT  ATACTTATAT  CAACCCTCTC  GACGGCACTT  ATCCGCCTGG  TACTGAGCAA 1980
1981  AACCCCGCTA  ATCCTAATCC  TTCTCTTGAG  GAGTCTCAGC  CTCTTAATAC  TTTCATGTTT 2040
2041  CAGAATAATA  GGTTCCGAAA  TAGGCAGGGG  GCATTAACTG  TTTATACGGG  CACTGTTACT 2100
2101  CAAGGCACTG  ACCCCGTTAA  AACTTATTAC  CAGTACACTC  CTGTATCATC  AAAAGCCATG 2160
2161  TATGACGCTT  ACTGGAACGG  TAAATTCAGA  GACTGCGCTT  TCCATTCTGG  CTTTAATGAA 2220
2221  GATCCATTCG  TTTGTGAATA  TCAAGGCCAA  TCGTCTGACC  TGCCTCAACC  TCCTGTCAAT 2280
2281  GCTGGCGGCG  GCTCTGGTGG  TGGTTCTGGT  GGCGGCTCTG  AGGGTGGTGG  CTCTGAGGGT 2340
2341  GGCGGTTCTG  AGGGTGGCGG  CTCTGAGGGA  GGCGGTTCCG  GTGGTGGCTC  TGGTTCCGGT 2400
2401  GATTTTGATT  ATGAAAAGAT  GGCAAACGCT  AATAAGGGGG  CTATGACCGA  AAATGCCGAT 2460
2461  GAAAACGCGC  TACAGTCTGA  CGCTAAAGGC  AAACTTGATT  CTGTCGCTAC  TGATTACGGT 2520
2521  GCTGCTATCG  ATGGTTTCAT  TGGTGACGTT  TCCGGCCTTG  CTAATGGTAA  TGGTGCTACT 2580
2581  GGTGATTTTG  CTGGCTCTAA  TTCCCAAATG  GCTCAAGTCG  GTGACGGTGA  TAATTCACCT 2640
2641  TTAATGAATA  ATTTCCGTCA  ATATTTACCT  TCCCTCCCTC  AATCGGTTGA  ATGTCGCCCT 2700
2701  TTTGTCTTTA  GCGCTGGTAA  ACCATATGAA  TTTTCTATTG  ATTGTGACAA  AATAAACTTA 2760
2761  TTCCGTGGTG  TCTTTGCGTT  TCTTTTATAT  GTTGCCACCT  TTATGTATGT  ATTTTCTACG 2820
2821  TTTGCTAACA  TACTGCGTAA  TAAGGAGTCT  TAATCATGCC  AGTTCTTTTG  GGTATTCCGT 2880
2881  TATTATTGCG  TTTCCTCGGT  TTCCTTCTGG  TAACTTTGTT  CGGCTATCTG  CTTACTTTTC 2940
2941  TTAAAAAGGG  CTTCGGTAAG  ATAGCTATTG  CTATTTCATT  GTTTCTTGCT  CTTATTATTG 3000
      |   10       |   20       |   30       |   40       |   50       |   60
```

FIG. 6A

```
         |    10     |    20     |    30     |    40     |    50     |    60
3001  GGCTTAACTC AATTCTTGTG GGTTATCTCT CTGATATTAG CGCTCAATTA CCCTCTGACT  3060
3061  TTGTTCAGGG TGTTCAGTTA ATTCTCCCGT CTAATGCGCT TCCCTGTTTT TATGTTATTC  3120
3121  TCTCTGTAAA GGCTGCTATT TTCATTTTTG ACGTTAAACA AAAAATCGTT TCTTATTTGG  3180
3181  ATTGGGATAA ATAATATGGC TGTTTATTTT GTAACTGGCA AATTAGGCTC TGGAAAGACG  3240
3241  CTCGTTAGCG TTGGTAAGAT TCAGGATAAA ATTGTAGCTG GGTGCAAAAT AGCAACTAAT  3300
3301  CTTGATTTAA GGCTTCAAAA CCTCCCGCAA GTCGGGAGGT TCGCTAAAAC GCCTCGCGTT  3360
3361  CTTAGAATAC CGGATAAGCC TTCTATATCT GATTTGCTTG CTATTGGGCG CGGTAATGAT  3420
3421  TCCTACGATG AAAATAAAAA CGGCTTGCTT GTTCTCGATG AGTGCGGTAC TTGGTTTAAT  3480
3481  ACCCGTTCTT GGAATGATAA GGAAAGACAG CCGATTATTG ATTGGTTTCT ACATGCTCGT  3540
3541  AAATTAGGAT GGGATATTAT TTTTCTTGTT CAGGACTTAT CTATTGTTGA TAAACAGGCG  3600
3601  CGTTCTGCAT TAGCTGAACA TGTTGTTTAT TGTCGTCGTC TGGACAGAAT TACTTTACCT  3660
3661  TTTGTCGGTA CTTTATATTC TCTTATTACT GGCTCGAAAA TGCCTCTGCC TAAATTACAT  3720
3721  GTTGGCGTTG TTAAATATGG CGATTCTCAA TTAAGCCCTA CTGTTGAGCG TTGGCTTTAT  3780
3781  ACTGGTAAGA ATTTGTATAA CGCATATGAT ACTAAACAGG CTTTTTCTAG TAATTATGAT  3840
3841  TCCGGTGTTT ATTCTTATTT AACGCCTTAT TTATCACACG GTCGGTATTT CAAACCATTA  3900
3901  AATTTAGGTC AGAAGATGAA GCTTACTAAA ATATATTTGA AAAGTTTTC ACGCGTTCTT  3960
3961  TGTCTTGCGA TTGGATTTGC ATCAGCATTT ACATATAGTT ATATAACCCA ACCTAAGCCG  4020
4021  GAGGTAAAAA AGGTAGTCTC TCAGACCTAT GATTTTGATA AATTCACTAT TGACTCTTCT  4080
4081  CAGCGTCTTA ATCTAAGCTA TCGCTATGTT TTCAAGGATT CTAAGGGAAA ATTAATTAAT  4140
4141  AGCGACGATT TACAGAAGCA AGGTTATTCA CTCACATATA TTGATTTATG TACTGTTTCC  4200
4201  ATTAAAAAAG GTAATTCAAA TGAAATTGTT AAATGTAATT AATTTTGTTT TCTTGATGTT  4260
4261  TGTTTCATCA TCTTCTTTTG CTCAGGTAAT TGAAATGAAT AATTCGCCTC TGCGCGATTT  4320
4321  TGTAACTTGG TATTCAAAGC AATCAGGCGA ATCCGTTATT GTTTCTCCCG ATGTAAAAGG  4380
4381  TACTGTTACT GTATATTCAT CTGACGTTAA ACCTGAAAAT CTACGCAATT TCTTTATTTC  4440
4441  TGTTTTACGT GCTAATAATT TTGATATGGT TGGTTCAATT CCTTCCATAA TTCAGAAGTA  4500
4501  TAATCCAAAC AATCAGGATT ATATTGATGA ATTGCCATCA TCTGATAATC AGGAATATGA  4560
4561  TGATAATTCC GCTCCTTCTG GTGGTTTCTT TGTTCCGCAA AATGATAATG TTACTCAAAC  4620
4621  TTTTAAAATT AATAACGTTC GGGCAAAGGA TTTAATACGA GTTGTCGAAT TGTTTGTAAA  4680
4681  GTCTAATACT TCTAAATCCT CAAATGTATT ATCTATTGAC GGCTCTAATC TATTAGTTGT  4740
4741  TAGTGCACCT AAAGATATTT TAGATAACCT TCCTCAATTC CTTTCTACTG TTGATTTGCC  4800
4801  AACTGACCAG ATATTGATTG AGGGTTTGAT ATTTGAGGTT CAGCAAGGTG ATGCTTTAGA  4860
4861  TTTTTCATTT GCTGCTGGCT CTCAGCGTGG CACTGTTGCA GGCGGTGTTA ATACTGACCG  4920
4921  CCTCACCTCT GTTTTATCTT CTGCTGGTGG TTCGTTCGGT ATTTTTAATG GCGATGTTTT  4980
4981  AGGGCTATCA GTTCGCGCAT TAAAGACTAA TAGCCATTCA AAAATATTGT CTCTGCCACG  5040
5041  TATTCTTACG CTTTCAGGTC AGAAGGGTTC TATCTCTGTT GGCCAGAATG TCCCTTTTAT  5100
5101  TACTGGTCGT GTGACTGGTG AATCTGCCAA TGTAAATAAT CCATTTCAGA CGATTGAGCG  5160
5161  TCAAAATGTA GGTATTTCCA TGAGCGTTTT TCCTGTTGCA ATGGCTGGCG GTAATATTGT  5220
5221  TCTGGATATT ACCAGCAAGG GCGATAGTTT GAGTTCTTCT ACTCAGGCAA GTGATGTTAT  5280
5281  TACTAATCAA AGAAGTATTG CTACAACGGT TAATTTGCGT GATGGACAGA CTCTTTTACT  5340
5341  CGGTGGCCTC ACTGATTATA AAAACACTTC TCAAGATTCT GGCGTACCGT TCCTGTCTAA  5400
5401  AATCCCTTTA ATCGGCCTCC TGTTTAGCTC CCGCTCTGAT TCCAACGAGG AAAGCACGTT  5460
5461  ATACGTGCTC GTCAAAGCAA CCATAGTACG CGCCCTGTAG CGGCGCATTA AGCGCGGCGG  5520
5521  GTGTGGTGGT TACGCGCAGC GTGACCGCTA CACTTGCCAG CGCCCTAGCG CCCGCTCCTT  5580
5581  TCGCTTTCTT CCCTTCCTTT CTCGCCACGT TCGCCGGCTT TCCCCGTCAA GCTCTAAATC  5640
5641  GGGGGCTCCC TTTAGGGTTC CGATTTAGTG CTTTACGGCA CCTCGACCCC AAAAAACTTG  5700
5701  ATTTGGGTGA TGGTTCACGT AGTGGGCCAT CGCCCTGATA GACGGTTTTT CGCCCTTTGA  5760
5761  CGTTGGAGTC CACGTTCTTT AATAGTGGAC TCTTGTTCCA AACTGGAACA ACACTCAACC  5820
5821  CTATCTCGGG CTATTCTTTT GATTTATAAG GGATTTTGCC GATTTCGGAA CCACCATCAA  5880
5881  ACAGGATTTT CGCCTGCTGG GGCAAACCAG CGTGGACCGC TTGCTGCAAC TCTCTCAGGG  5940
5941  CCAGGCGGTG AAGGGCAATC AGCTGTTGCC CGTCTCGCTG GTGAAAAGAA AAACCACCCT  6000
         |    10     |    20     |    30     |    40     |    50     |    60
```

FIG. 6B

```
       |    10     |    20     |    30     |    40     |    50     |    60
6001   GGCGCCCAAT  ACGCAAACCG  CCTCTCCCCG  CGCGTTGGCC  GATTCATTAA  TGCAGCTGGC   6060
6061   ACGACAGGTT  TCCCGACTGG  AAAGCGGGCA  GTGAGCGCAA  CGCAATTAAT  GTGAGTTAGC   6120
6121   TCACTCATTA  GGCACCCCAG  GCTTTACACT  TTATGCTTCC  GGCTCGTATG  TTGTGTGGAA   6180
6181   TTGTGAGCGG  ATAACAATTT  CACACGCCAA  GGAGACAGTC  ATAATGAAAT  ACCTATTGCC   6240
6241   TACGGCAGCC  GCTGGATTGT  TATTACTCGC  TGCCCAACCA  GCCATGGCCG  AGCTCTTCCC   6300
6301   GCCATCTGAT  GAGCAGTTGA  AATCTGGAAC  TGCCTCTGTT  GTGTGCCTGC  TGAATAACTT   6360
6361   CTATCCCAGA  GAGGCCAAAG  TACAGTGGAA  GGTGGATAAC  GCCCTCCAAT  CGGGTAACTC   6420
6421   CCAGGAGAGT  GTCACAGAGC  AGGACAGCAA  GGACAGCACC  TACAGCCTCA  GCAGCACCCT   6480
6481   GACGCTGAGC  AAAGCAGACT  ACGAGAAACA  CAAAGTCTAC  GCCTGCGAAG  TCACCCATCA   6540
6541   GGGCCTGAGC  TCGCCCGTCA  CAAAGAGCTT  CAACAGGGGA  GAGTGTTCTA  GAACGCGTCA   6600
6601   CTTGGCACTG  GCCGTCGTTT  TACAACGTCG  TGACTGGGAA  AACCCTGGCG  TTACCCAAGC   6660
6661   TTTGTACATG  GAGAAAATAA  AGTGAAACAA  AGCACTATTG  CACTGGCACT  CTTACCGTTA   6720
6721   CTGTTTACCC  CTGTGGCAAA  AGCCGCCTCC  ACCAAGGGCC  CATCGGTCTT  CCCCCTGGCA   6780
6781   CCCTCCTCCA  AGAGCACCTC  TGGGGGCACA  GCGGCCCTGG  GCTGCCTGGT  CAAGACTAAT   6840
6841   TCCCCGAACC  GGTGACGGTG  TCGTGGAACT  CAGGCGCCCT  GACCAGCGGC  GTGCACACCT   6900
6901   TCCCGGCTGT  CCTACAGTCC  TCAGGACTCT  ACTCCCTCAG  CAGCGTGGTG  ACCGTGCCCT   6960
6961   CCAGCAGCTT  GGGCACCCAG  ACCTACATCT  GCAACGTGAA  TCACAAGCCC  AGCAACACCA   7020
7021   AGGTGGACAA  GAAAGCAGAG  CCCAAATCTT  GTACTAGTGG  ATCCTACCCG  TACGACGTTC   7080
7081   CGGACTACGC  TTCTTAGGCT  GAAGGCGATG  ACCCTGCTAA  GGCTGCATTC  AATAGTTTAC   7140
7141   AGGCAAGTGC  TACTGAGTAC  ATTGGCTACG  CTTGGGCTAT  GGTAGTAGTT  ATAGTTGGTG   7200
7201   CTACCATAGG  GATTAAATTA  TTCAAAAAGT  TTACGAGCAA  GGCTTCTTAA  GCAATAGCGA   7260
7261   AGAGGCCCGC  ACCGATCGCC  CTTCCCAACA  GTTGCGCAGC  CTGAATGGCG  AATGGCGCTT   7320
7321   TGCCTGGTTT  CCGGCACCAG  AAGCGGTGCC  GGAAAGCTGG  GTGGAGTGCG  ATCTTCCTGA   7380
7381   GGCCGATACG  GTCGTCGTCC  CCTCAAACTG  GCAGATGCAC  GGTTACGATG  CGCCCATCTA   7440
7441   CACCAACGTA  ACCTATCCCA  TTACGGTCAA  TCCGCCGTTT  GTTCCCACGG  AGAATCCGAC   7500
7501   GGGTTGTTAC  TCGCTCACAT  TTAATGTTGA  TGAAAGCTGG  CTACAGGAAG  GCCAGACGCG   7560
7561   AATTATTTTT  GATGGCGTTC  CTATTGGTTA  AAAAATGAGC  TGATTTAACA  AAAATTTAAC   7620
7621   GCGAATTTTA  ACAAAATATT  AACGTTTACA  ATTTAAATAT  TTGCTTATAC  AATCTTCCTG   7680
7681   TTTTTGGGGC  TTTTTCTGAT  TATCAACCGG  GTACATATGA  TTGACATGCT  AGTTTTACGA   7740
7741   TTACCGTTCA  TCGATTCTCT  TGTTTGCTCC  AGACTCTCAG  GCAATGACCT  GATAGCCTTT   7800
7801   GTAGATCTCT  CAAAAATAGC  TACCCTCTCC  GGCATTAATT  TATCAGCTAG  AACGGTTGAA   7860
7861   TATCATATTG  ATGGTGATTT  GACTGTCTCC  GGCCTTTCTC  ACCCTTTTGA  ATCTTTACCT   7920
7921   ACACATTACT  CAGGCATTGC  ATTTAAAATA  TATGAGGGTT  CTAAAAATTT  TTATCCTTGC   7980
7981   GTTGAAATAA  AGGCTTCTCC  CGCAAAAGTA  TTACAGGGTC  ATAATGTTTT  TGGTACAACC   8040
8041   GATTTAGCTT  TATGCTCTGA  GGCTTTATTG  CTTAATTTTG  CTAATTCTTT  GCCTTGCCTG   8100
8101   TATGATTTAT  TGGACGTT                                                     8118
       |    10     |    20     |    30     |    40     |    50     |    60
```

FIG. 6C

SURFACE EXPRESSION LIBRARIES OF HETEROMERIC RECEPTORS

This application is a continuation of application Ser. No. 08/120,648, filed Sep. 13, 1993, (now abandoned) which is a continuation of U.S. Ser. No. 07/767,136 filed Sep. 27, 1991, (now abandoned) which is a continuation-in-part of U.S. Ser. No. 07/590,219 filed Sep. 28, 1990 (now abandoned).

BACKGROUND OF THE INVENTION

This invention relates generally to recombinant expression of heteromeric receptors and, more particularly, to expression of such receptors on the surface of filamentous bacteriophage.

Antibodies are heteromeric receptors generated by a vertebrates organism's immune system which bind to an antigen. The molecules are composed of two heavy and two light chains disulfide bonded together. Antibodies have the appearance of a "Y"—shaped structure and the antigen binding portion being located at the end of both short arms of the Y. The region on the heavy and light chain polypeptides which corresponds to the antigen binding portion is known as variable region. The differences between antibodies within this region are primarily responsible for the variation in binding specificities between antibody molecules. The binding specificities are a composite of the antigen interactions with both heavy and light chain polypeptides.

The immune system has the capability of generating an almost infinite number of different antibodies. Such a large diversity is generated primarily through recombination to form the variable regions of each chain and through differential pairing of heavy and light chains. The ability to mimic the natural immune system and generate antibodies that bind to any desired molecule is valuable because such antibodies can be used for diagnostic and therapeutic purposes.

Until recently, generation of antibodies against a desired molecule was accomplished only through manipulation of natural immune responses. Methods included classical immunization techniques of laboratory animals and monoclonal antibody production. Generation of monoclonal antibodies is laborious and time consuming. It involves a series of different techniques and is only performed on animal cells. Animal cells have relatively long generation times and require extra precautions to be taken compared to procaryotic cells to ensure viability of the cultures.

A method for the generation of a large repertoire of diverse antibody molecules in bacteria has been described, Huse et al., Science, 246, 1275–1281 (1989), which is herein incorporated by reference. The method uses the bacteriophage lambda as the vector. The lambda vector is a long, linear double-stranded DNA molecule. Production of antibodies using this vector involves the cloning of heavy and light chain populations of DNA sequences into separate vectors. The vectors are subsequently combined randomly to form a single vector which directs the coexpression of heavy and light chains to form antibody fragments. A disadvantage to this method is that undesired combinations of vector portions are brought together when generating the coexpression vector. Although these undesired combinations do not produce viable phage, they do however, result in a significant loss of sequences from the population and, therefore, a loss in diversity of the number of different combinations which can be obtained between heavy and light chains. Additionally, the size of the lambda phage gene is large compared to the genes that encode the antibody segments. This makes the lambda system inherently more difficult to manipulate as compared to other available vector systems.

There thus exists a need for a method to generate diverse populations of heteromeric receptors which mimics the natural immune system, which is fast and efficient and results in only desired combinations without loss of diversity. The present invention satisfies these needs and provides related advantages as well.

SUMMARY OF THE INVENTION

The invention relates to a plurality of cells containing diverse combinations of first and second DNA sequences encoding first and second polypeptides which form a heteromeric receptor, said heteromeric receptors being expressed on the surface of a cell, preferably one which produces filamentous bacteriophage, such as M13. Vectors, cloning systems and methods of making and screening the heteromeric receptors are also provided.

BRIEF DESCRIPTION OF THE DRAWINGS

FIG. 1C shows the joining of vector population from heavy and light chain libraries to form the functional surface expression vector M13IXHL. FIG. 1D shows the generation of a surface expression library in a non-suppressor strain and the production of phage. The phage are used to infect a suppressor strain (FIG. 1E) for surface expression and screening of the library.

FIG. 2A, 2B and 2C is the nucleotide sequence of M13IX30 (SEQ ID NO: 1).

FIG. 3A, 3B and 3C is the nucleotide sequence of M13IX11 (SEQ ID NO:2).

FIG. 4A, 4B and 4C is the nucleotide sequence of M13IX34 (SEQ ID NO: 3).

FIG. 5A, 5B and 5C is the nucleotide sequence of M13IX13 (SEQ ID NO: 4).

FIG. 6A, 6B and 6C is the nucleotide sequence of M13IX60 (SEQ ID NO: 5).

DETAILED DESCRIPTION OF THE INVENTION

Figure 1:
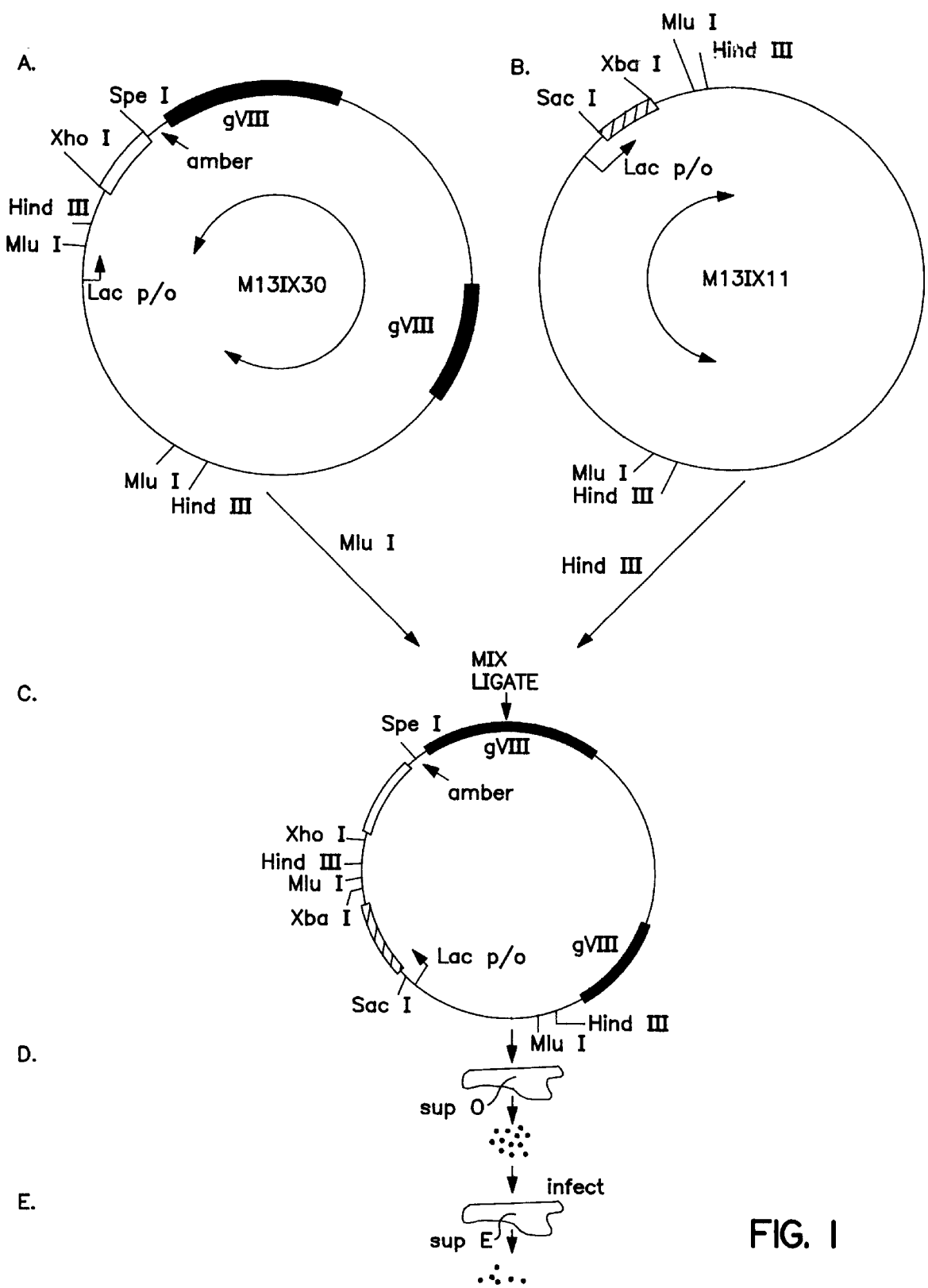
FIG. 1 is a schematic diagram of the two vectors used for surface expression library construction from heavy and light chain libraries. M13IX30 (FIG. 1A) is the vector used to clone the heavy chain sequences (open box). The single-headed arrow represents the Lac p/o expression sequences and the double-headed arrow represents the portion of M13IX30 which is to be combined with M13IX11. The amber stop codon and relevant restriction sites are also shown. M13IX11 (FIG. 1B) is the vector used to clone the light chain sequences (hatched box). Thick lines represent the pseudo-wild type ($\Psi$ gVIII) and wild type (gVIII) gene VIII sequences. The double-headed arrow represents the portion of M13IX11 which is to be combined with M13IX30. Relevant restriction sites are also shown.

This invention is directed to simple and efficient methods to generate a large repertoire of diverse combinations of heteromeric receptors. The method is advantageous in that only proper combinations of vector portions are randomly brought together for the coexpression of different DNA sequences without loss of population size or diversity. The receptors can be expressed on the surface of cells, such as those producing filamentous bacteriophage, which can be screened in large numbers. The nucleic acid sequences encoding the receptors be readily characterized because the filamentous bacteriophage produce single strand DNA for efficient sequencing and mutagenesis methods. The heteromeric receptors so produced are useful in an unlimited number of diagnostic and therapeutic procedures.

In one embodiment, two populations of diverse heavy (Hc) and light (Lc) chain sequences are synthesized by polymerase chain reaction (PCR). These populations are cloned into separate M13-based vector containing elements necessary for expression. The heavy chain vector contains a gene VIII (gVIII) coat protein sequence so that translation of the Hc sequences produces gVIII-Hc fusion proteins. The populations of two vectors are randomly combined such that only the vector portions containing the Hc and Lc sequences are joined into a single circular vector. The combined vector directs the coexpression of both Hc and Lc sequences for assembly of the two polypeptides and surface expression on M13. A mechanism also exists to control the expression of gVIII-Hc fusion proteins during library construction and screening.

As used herein, the term "heteromeric receptors" refers to proteins composed of two or more subunits which together exhibit binding activity toward particular molecule. It is understood that the term includes the subunit fragments so long as assembly of the polypeptides and function of the assembled complex is retained. Heteromeric subunits include, for example, antibodies and fragments thereof such as Fab and (Fab)$_2$ portions, T cell receptors, integrins, hormone receptors and transmitter receptors.

As used herein, the term "preselected molecule" refers to a molecule which is chosen from a number of choices. The molecule can be, for example, a protein or peptide, or an organic molecule such as a drug. Benzodiazapam is a specific example of a preselected molecule.

As used herein, the term "coexpression" refers to the expression of two or more nucleic acid sequences usually expressed as separate polypeptides. For heteromeric receptors, the coexpressed polypeptides assemble to form the heteromer. Therefore, "expression elements" as used herein, refers to sequences necessary for the transcription, translation, regulation and sorting of the expressed polypeptides which make up the heteromeric receptors. The term also includes the expression of two subunit polypeptides which are linked but are able to assemble into a heteromeric receptor. A specific example of coexpression of linked polypeptides is where Hc and Lc polypeptides are expressed with a flexible peptide or polypeptide linker joining the two subunits into a single chain. The linker is flexible enough to allow association of Hc and Lc portions into a functional Fab fragment.

The invention provides for a composition of matter comprising a plurality of procaryotic cells containing diverse combinations of first and second DNA sequences encoding first and second polypeptides which form a heteromeric receptor exhibiting binding activity toward a preselected molecule, said heteromeric receptors being expressed on the surface of filamentous bacteriophage.

DNA sequences encoding the polypeptides of heteromeric receptors are obtained by methods known to one skilled in the art. Such methods include, for example, cDNA synthesis and polymerase chain reaction (PCR). The need will determine which method or combinations of methods is to be used to obtain the desired populations of sequences. Expression can be performed in any compatible vector/host system. Such systems include, for example, plasmids or phagemids in procaryotes such as *E. coli*, yeast systems and other eucaryotic systems such as mammalian cells, but will be described herein in context with its presently preferred embodiment, i.e. expression on the surface of filamentous bacteriophage. Filamentous bacteriophage include, for example, M13, f1 and fd. Additionally, the heteromeric receptors can also be expressed in soluble or secreted form depending on the need and the vector/host system employed.

Expression of heteromeric receptors such as antibodies or functional fragments thereof on the surface of M13 can be accomplished, for example, using the vector system shown in FIG. 1. Construction of the vectors enabling one of ordinary skill to make them are explicitly set out in Example I. The complete nucleotide sequences are given in FIGS. 2A, 2B and 2C and FIGS. 3A, 3B and 3C (SEQ ID NOS: 1 and 2). This system randomly combined populations of heavy (Hc) and light (Lc) chain antibody fragments functionally linked to expression elements. The Hc polypeptide is produced as a fusion protein with the M13 coat protein encoded by gene VIII. The gVIII-Hc fusion protein therefore anchors the assembled Hc and Lc polypeptides on the surface of M13. The diversity of Hc and Lc combinations obtained by this system can be $5 \times 10^7$ or greater. Diversity of less than $5 \times 10^7$ can also be obtained and will be determined by the need and type of heteromeric receptor to be expressed.

Populations of Hc and Lc encoding sequences to be combined into a vector for coexpression are each cloned into separate vectors. For the vectors shown in FIG. 1, diverse populations of sequences encoding Hc polypeptides are cloned into M13IX30 (SEQ ID NO: 1). Sequences encoding Lc polypeptides are cloned into M13IX11 (SEQ ID NO: 2). The populations are inserted between the Xho I-Spe I or Stu I restriction enzyme sites in M13IX30 and between the Sac I-Xba I or Eco RV sites in M13IX11 (FIGS. 1A and B, respectively).

The populations of Hc and Lc sequences inserted into the vectors can be synthesized with appropriate restriction recognition sequences flanking opposite ends of the encoding sequences but this is not necessary. The sites allow annealing and ligation in-frame with expression elements of these sequences into a double-stranded vector restricted with the appropriate restriction enzyme. Alternatively, and a preferred embodiment, the Hc and Lc sequences can be inserted into the vector without restriction of the DNA. This method of cloning is beneficial because naturally encoded restriction enzyme sites may be present within the sequences, thus, causing destruction of the sequence when treated with a restriction enzyme. For cloning without restriction, the sequences are treated briefly with a 3' to 5' exonuclease such as T4 DNA polymerase or exonuclease III. A 5' to 3' exonuclease will also accomplish the same function. The protruding 5' termini which remains should be complementary to single-stranded overhangs within the vector which remain after restriction at the cloning site and treatment with exonuclease. The exonuclease treated inserts are annealed with the restricted vector by methods known to one skilled in the art. The exonuclease method decreases background and is easier to perform.

The vector used for Hc populations, M13IX30 (FIG. 1A; SEQ ID NO: 1) contains, in addition to expression elements, a sequence encoding the pseudo-wild type gVIII product downstream and in frame with the cloning sites. This gene encodes the wild type M13 gVIII amino acid sequence but has been changed at the nucleotide level to reduce homologous recombination with the wild type gVIII contained on the same vector. The wild type gVIII is present to ensure that at least some functional, non-fusion coat protein will be produced. The inclusion of a wild type gVIII therefore reduces the possibility of non-viable phage production and biological selection against certain peptide fusion proteins. Differential regulation of the two genes can also be used to control the relative ratio of the pseudo and wild type proteins.

Also contained downstream and in frame with the cloning sites is an amber stop codon. The stop codon is located between the inserted Hc sequences and the gVIII sequence and is in frame. As was the function of the wild type gVIII, the amber stop codon also reduces biological selection when combining vector portions to produce functional surface expression vectors. This is accomplished by using a non-suppressor (sup O) host strain because the non-suppressor strains will terminate expression after the Hc sequences but before the pseudo gVIII sequences. Therefore, the pseudo gVIII will essentially never be expressed on the phage surface under these circumstances. Instead, only soluble Hc polypeptides will be produced. Expression in a non-suppressor host strain can be advantageously utilized when one wishes to produce large populations of antibody fragments. Stop codons other than amber, such as opal and ochre, or molecular switches, such as inducible repressor elements, can also be used to unlink peptide expression from surface expression.

The vector used for Lc populations, M13IX11 (SEQ ID NO: 2), contains necessary expression elements and cloning sites for the Lc sequences, FIG. 1B. As with M13IX30, upstream and in frame with the cloning sites is a leader sequence for sorting to the phage surface. Additionally, a ribosome binding site and Lac Z promoter/operator elements are also present for transcription and translation of the DNA sequences.

Both vectors contain two pairs of Mlu I-Hind III restriction enzyme sites (FIGS. 1A and B) for joining together the Hc and Lc encoding sequences and their associated vector sequences. Mlu I and Hind III are non-compatible restriction sites. The two pairs are symmetrically orientated about the cloning site so that only the vector portions containing the sequences to be expressed are exactly combined into a single vector. The two pairs of sites are oriented identically with respect to one another on both vectors and the DNA between the two sites must be homologous enough between both vectors to allow annealing. This orientation allows cleavage of each circular vector into two portions and combination of essential components within each vector into a single circular vector where the encoded polypeptides can be coexpressed (FIG. 1C).

Any two pairs of restriction enzyme sites can be used so long as they are symmetrically orientated about the cloning site and identically orientated on both vectors. The sites within each pair, however, should be non-identical or able to be made differentially recognized as a cleavage substrate. For example, the two pairs of restriction sites contained within the vectors shown in FIG. 1 are Mlu I and Hind III. The sites are differentially cleavable by Mlu I and Hind III respectively. One skilled in the art knows how to substitute alternative pairs of restriction enzyme sites for the Mlu I-Hind III pairs described above. Also, instead of two Hind III and two Mlu I sites, a Hind III and Not I site can be paired with a Mlu I and a Sal I site, for example.

The combining step randomly brings together different Hc and Lc encoding sequences within the two diverse populations into a single vector (FIG. 1C; M13IXHL). The vector sequences donated from each independent vector, M13IX30 and M13IX11, are necessary for production of viable phage. Also, since the pseudo gVIII sequences are contained in M13IX30, coexpression of functional antibody fragments as Lc associated gVIII-Hc fusion proteins cannot be accomplished on the phage surface until the vector sequences are linked as shown in M13IXHL.

The combining step is performed by restricting each population of Hc and Lc containing vectors with Mlu I and Hind III, respectively. The 3' termini of each restricted vector population is digested with a 3' to 5' exonuclease as described above for inserting sequences into the cloning sites. The vector populations are mixed, allowed to anneal and introduced into an appropriate host. A non-suppressor host (FIG. 1D) is preferably used during initial construction of the library to ensure that sequences are not selected against due to expression as fusion proteins. Phage isolated from the library constructed in a non-suppressor strain can be used to infect a suppressor strain for surface expression of antibody fragments.

A method for selecting a heteromeric receptor exhibiting binding activity toward a preselected molecule from a population of diverse heteromeric receptors, comprising: (a) operationally linking to a first vector a first population of diverse DNA sequences encoding a diverse population of first polypeptides, said first vector having two pairs of restriction sites symmetrically oriented about a cloning site; (b) operationally linking to a second vector a second population of diverse DNA sequences encoding a diverse population of second polypeptides, said second vector having two pairs of restriction sites symmetrically oriented about a cloning site in an identical orientation to that of the first vector; (c) combining the vector products of step (a) and (b) under conditions which allow only the operational combination of vector sequences containing said first and second DNA sequences; (d) introducing said population of combined vectors into a compatible host under conditions sufficient for expressing said population of first and second DNA sequences; and (e) determining the heteromeric receptors which bind to said preselected molecule. The invention also provides for determining the nucleic acid sequences encoding such polypeptides as well.

Surface expression of the antibody library is performed in an amber suppressor strain. As described above, the amber stop codon between the Hc sequence and the gVIII sequence unlinks the two components in a non-suppressor strain. Isolating the phage produced from the non-suppressor strain and infecting a suppressor strain will link the Hc sequences to the gVIII sequence during expression (FIG. 1E). Culturing the suppressor strain after infection allows the coexpression on the surface of M13 of all antibody species within the library as gVIII fusion proteins (gVIII-Fab fusion proteins). Alternatively, the DNA can be isolated from the non-suppressor strain and then introduced into a suppressor strain to accomplish the same effect.

The level of expression of gVIII-Fab fusion proteins can additionally be controlled at the transcriptional level. Both polypeptides of the gVIII-Fab fusion proteins are under the inducible control of the Lac Z promoter/operator system. Other inducible promoters can work as well and are known by one skilled in the art. For high levels of surface expression, the suppressor library is cultured in an inducer of the Lac Z promoter such as isopropylthio-β-galactoside (IPTG). Inducible control is beneficial because biological selection against non-functional gVIII-Fab fusion proteins can be minimized by culturing the library under non-expressing conditions. Expression can then be induced only at the time of screening to ensure that the entire population of antibodies within the library are accurately represented on the phage surface. Also, this can be used to control the valency of the antibody on the phage surface.

The surface expression library is screened for specific Fab fragments which bind preselected molecules by standard affinity isolation procedures. Such methods include, for example, panning, affinity chromatography and solid phase blotting procedures. Panning as described by Parmley and Smith, Gene 73:305–318 (1988), which is incorporated herein by reference, is preferred because high titers of phage can be screened easily, quickly and in small volumes. Furthermore, this procedure can select minor Fab fragments species within the population, which otherwise would have been undetectable, and amplified to substantially homogenous populations. The selected Fab fragments can be characterized by sequencing the nucleic acids encoding the polypeptides after amplification of the phage population.

The following examples are intended to illustrate but not limit the invention.

EXAMPLE I

Construction Expression and Screening of Antibody Fragments on the Surface of M13

This example shows the synthesis of a diverse population of heavy (Hc) and light (Lc) chain antibody fragments and their expression on the surface of M13 as gene VIII-Fab fusion proteins. The expressed antibodies derive from the random mixing and coexpression of a Hc and Lc pair. Also demonstrated is the isolation and characterization of the expressed Fab fragments which bind benzodiazapam (BDP) and their corresponding nucleotide sequence.

Isolation of mRNA and PCR Amplification of Antibody Fragments

The surface expression library is constructed from mRNA isolated from a mouse that had been immunized with KLH-coupled benzodiazapam (BDP). BDP was coupled to keyhole limpet hemocyanin (KLH) using the techniques described in *Antibodies: A Laboratory Manual*, Harlow and Lane, eds., Cold Spring Harbor, N.Y. (1988), which is incorporated herein by reference. Briefly, 10.0 milligrams (mg) of keyhole limpet hemocyanin and 0.5 mg of BDP with a glutaryl spacer arm N-hydroxysuccinimide linker appendages. Coupling was performed as in Jonda et al., *Science*, 241:1188 (1988), which is incorporated herein by reference. The KLH-BDP conjugate was removed by gel filtration chromatography through Sephadex G-25.

The KLH-BDP conjugate was prepared for injection into mice by adding 100 μg of the conjugate to 250 μl of phosphate buffered saline (PBS). An equal volume of complete Freund's adjuvant was added and emulsified the entire solution for 5 minutes. Mice were injected with 300 μl of the emulsion. Injections were given subcutaneously at several sites using a 21 gauge needle. A second immunization with BDP was given two weeks later. This injection was prepared as follows: 50 μg of BDP was diluted in 250 μl of PBS and an equal volume of alum was mixed with the solution. The mice were injected intraperitoneally with 500 μl of the solution using a 23 gauge needle. One month later the mice were given a final injection of 50 μg of the conjugate diluted to 200 μl in PBS. This injection was given intravenously in the lateral tail vein using a 30 gauge needle. Five days after this final injection the mice were sacrificed and total cellular RNA was isolated from their spleens.

Total RNA was isolated from the spleen of a single mouse immunized as described above by the method of Chomczynski and Sacchi, *Anal. Biochem.*, 162:156–159 (1987), which is incorporated herein by reference. Briefly, immediately after removing the spleen from the immunized mouse, the tissue was homogenized in 10 ml of a denaturing solution containing 4.0M guanine isothiocyanate, 0.25M sodium citrate at pH 7.0, and 0.1M 2-mercaptoethanol using a glass homogenizer. One ml of sodium acetate at a concentration of 2M at pH 4.0 was mixed with the homogenized spleen. One ml of saturated phenol was also mixed with the denaturing solution containing the homogenized spleen. Two ml of a chloroform: isoamyl alcohol (24:1 v/v) mixture was added to this homogenate. The homogenate was mixed vigorously for ten seconds and maintained on ice for 15 minutes. The homogenate was then transferred to a thick-walled 50 ml polypropylene centrifuge tube (Fisher Scientific Company, Pittsburgh, Pa.). The solution was centrifuged at 10,000×g for 20 minutes at 4° C. The upper RNA-containing aqueous layer was transferred to a fresh 50 ml polypropylene centrifuge tube and mixed with an equal volume of isopropyl alcohol. This solution was maintained at −20° C. for at least one hour to precipitate the RNA. The solution containing the precipitated RNA was centrifuged at 10,000×g for twenty minutes at 4° C. The pelleted total cellular RNA was collected and dissolved in 3 ml of the denaturing solution described above. Three mls of isopropyl alcohol was added to the resuspended total cellular RNA and vigorously mixed. This solution was maintained at −20° C. for at least 1 hour to precipitate the RNA. The solution containing the precipitated RNA was centrifuged at 10,000×g for ten minutes at 4° C. The pelleted RNA was washed once with a solution containing 75% ethanol. The pelleted RNA was dried under vacuum for 15 minutes and then resuspended in dimethyl pyrocarbonate (DEPC) treated (DEPC-H$_2$O) H$_2$O.

Poly A$^+$RNA for use in first strand cDNA synthesis was prepared from the above isolated total RNA using a spin-column kit (Pharmacia, Piscataway, N.J.) as recommended by the manufacturer. The basic methodology has been described by Aviv and Leder, *Proc. Natl. Acad. Sci., USA*, 69:1408–1412 (1972), which is incorporated herein by reference. Briefly, one half of the total RNA isolated from a single immunized mouse spleen prepared as described above was resuspended in one ml of DEPC-treated dH$_2$O and maintained at 65° C. for five minutes. One ml of 2× high salt loading buffer (100 mM Tris-HCL at pH 7.5, 1M sodium chloride, 2.0 mM disodium ethylene diamine tetraacetic acid (EDTA) at pH 8.0, and 0.2% sodium dodecyl sulfate (SDS)) was added to the resuspended RNA and the mixture was allowed to cool to room temperature. The mixture was then applied to an oligo-dT (Collaborative Research Type 2 or Type 3 Bedford, Mass.) column that was previously prepared by washing the oligo-dT with a solution containing 0.1M sodium hydroxide and 5 mM EDTA and then equilibrating the column with DEPC-treated dH$_2$O The eluate was collected in a sterile polypropylene tube and reapplied to the same column after heating the eluate for 5 minutes at 65° C. The oligo dT column was then washed with 2 ml of high salt loading buffer consisting of 50 mM Tris-HCL at pH 7.5, 500 mM sodium chloride, 1 mM EDTA at pH 8.0 and 0.1% SDS. The oligo dT column was then washed with 2 ml of 1×medium salt buffer (50 mM Tris-HCL at pH 7.5, 100 mM sodium chloride, 1 mM EDTA at pH 8.0 and 0.1% SDS). The mRNA was eluted with 1 ml of buffer consisting of 10 mM Tris-HCL at pH 7.5, 1 mM EDTA at pH 8.0 and 0.05% SDS. The messenger RNA was purified by extracting this solution with phenol/chloroform followed by a single extraction with 100% chloroform, ethanol precipitated and resuspended in DEPC treated dH$_2$O.

In preparation for PCR amplification, mRNA was used as a template for cDNA synthesis. In a typical 250 μl reverse transcription reaction mixture, 5–10 μg of spleen mRNA in water was first annealed with 500 ng (0.5 pmol) of either the 3' $V_H$ primer (primer 12, Table I) or the 3' $V_L$ primer (primer 9, Table II) at 65° C. for 5 minutes. Subsequently, the mixture was adjusted to contain 0.8 mM dATP, 0.8 mM dCTP, 0.8 mM dGTP, 0.8 mM dTTP, 100 mM Tris-HCL (pH 8.6), 10 mM $MgCl_2$, 40 mM KCl, and 20 mM 2-ME. Moloney-Murine Leukemia Virus (Bethesda Research Laboratories (BRL), Gaithersburg, Md. Reverse transcriptase, 26 units, was added and the solution was incubated for 1 hour at 40° C. The resultant first strand cDNA was phenol extracted, ethanol precipitated and then used in the polymerase chain reaction (PCR) procedures described below for amplification of heavy and light chain sequences.

Primers used for amplification of heavy chain Fd fragments for construction of the M13IX30 library is shown in Table I. Amplification was performed in eight separate reactions, as described by Saiki et al., *Science*, 239:487–491 (1988), which is incorporated herein by reference, each reaction containing one of the 5' primers (primers 2 to 9; SEQ ID NOS: 7 through 14, respectively) and one of the 3' primers (primer 12; SEQ ID NO: 17) listed in Table I. The remaining 5' primers, used for amplification in a single reaction, are either a degenerate primer (primer 1; SEQ ID NO: 6) or a primer that incorporates inosine at four degenerate positions (primer 10; SEQ ID NO: 15). The remaining 3' primer (primer 11; SEQ ID NO: 16) was used to construct Fv fragments. The underlined portion of the 5' primers incorporates an Xho I site and that of the 3' primer an Spe I restriction site for cloning the amplified fragments into the M13IX30 vector in a predetermined reading frame for expression.

TABLE I

HEAVY CHAIN PRIMERS

| | |
|---|---|
| 1) | 5' - AGGT CC A CT G CTCGAGTC GG - 3'<br>GA A T A |
| 2) | 5' - AGGTCCAGCTGCTCGAGTCTGG - 3' |
| 3) | 5' - AGGTCCAGCTGCTCGAGTCAGG - 3' |
| 4) | 5' - AGGTCCAGCTTCTCGAGTCTGG - 3' |
| 5) | 5' - AGGTCCAGCTTCTCGAGTCAGG - 3' |
| 6) | 5' - AGGTCCAACTGCTCGAGTCTGG - 3' |
| 7) | 5' - AGGTCCAACTGCTCGAGTCAGG - 3' |
| 8) | 5' - AGGTCCAACTTCTCGAGTCTGG - 3' |
| 9) | 5' - AGGTCCAACTTCTCGAGTCAGG - 3'<br>T |
| 10) | 5' - AGGTIIAICTICTCGAGTC GG - 3'<br>A |
| 11) | 5' - CTATTAACTAGTAACGGTAACAGT - GGTGCCTTGCCCCA - 3' |
| 12) | 5' - AGGCTTACTAGTACAATCCCTGG - GCACAAT - 3' |

Primers used for amplification of mouse kappa light chain sequences for construction of the M13IX11 library are shown in Table II. These primers were chosen to contain restriction sites which were compatible with vector and not present in the conserved sequences of the mouse light chain mRNA. Amplification was performed as described above in five separate reactions, each containing one of the 5' primers (primers 3 to 7; SEQ ID NOS: 20 through 24, respectively) and one of the 3' primers (primer 9; SEQ ID NO: 26) listed in Table II. The remaining 3' primer (primer 8; SEQ ID NO: 25) was used to construct Fv fragments. The underlined portion of the 5' primers depicts a Sac I restriction site and that of the 3' primers an Xba I restriction site for cloning of the amplified fragments into the M13IX11 vector in a predetermined reading frame for expression.

TABLE II

LIGHT CHAIN PRIMERS

| | |
|---|---|
| 1) | 5' - CCAGTTCCGAGCTCGTTGTGACTCAGGAATCT - 3' |
| 2) | 5' - CCAGTTCCGAGCTCGTGTTGACGCAGCCGCCC - 3' |
| 3) | 5' - CCAGTTCCGAGCTCGTGCTCACCCAGTCTCCA - 3' |
| 4) | 5' - CCAGTTCCGAGCTCCAGATGACCCAGTCTCCA - 3' |
| 5) | 5' - CCAGATGTGAGCTCGTGATGACCCAGACTCCA - 3' |
| 6) | 5' - CCAGATGTGAGCTCGTCATGACCCAGTCTCCA - 3' |
| 7) | 5' - CCAGTTCCGAGCTCGTGATGACACAGTCTCCA - 3' |
| 8) | 5' - GCAGCATTCTAGAGTTTCAGCTCCAGCTTGCC - 3' |
| 9) | 5' - GCGCCGTCTAGAATTAACACTCATTCCTGTTGAA - 3' |

PCR amplification for heavy and light chain fragments was performed in a 100 µl reaction mixture containing the above described products of the reverse transcription reaction ($\approx 5\mu g$ of the cDNA-RNA hybrid), 300 nmol of 3' $V_H$ primer (primer 12, Table I; SEQ ID NO: 17), and one of the 5' $V_H$ primers (primers 2–9, Table I; SEQ ID NOS: 7 through 14, respectively) for heavy chain amplification, or, 300 nmol of 3' $V_L$ primer (primer 9, Table II; SEQ ID NO: 26), and one of the 5' $V_L$ primers (primers 3–7, Table II; SEQ ID NOS: 20 through 24, respectively) for each light chain amplification, a mixture of dNTPs at 200 mM, 50 mM KCl, 10 mM Tris-HCl (pH 8.3), 15 mM $MgCl_2$, 0.1% gelatin, and 2 units of Thermus aquaticus DNA polymerase. The reaction mixture was overlaid with mineral oil and subjected to 40 cycles of amplification. Each amplification cycle involved denaturation at 92° C. for 1 minute, annealing at 52° C. for 2 minutes, and elongation at 72° C. for 1.5 minutes. The amplified samples were extracted twice with phenol/$CHCl_3$ and once with $CHCl_3$, ethanol-precipitated, and stored at –70° C. in 10 mM Tris-HCl, pH 7.5 1 mM EDTA. The resultant products were used in constructing the M13IX30 and M13IX11 libraries (see below).

Vector Construction

Two M13-based vectors, M13IX30 (SEQ ID NO: 1) and M13IX11 (SEQ ID NO: 2), were constructed for the cloning and propagation of Hc and Lc populations of antibody fragments, respectively. The vectors were constructed to facilitate the random joining and subsequent surface expression of antibody fragment populations.

M13TX30 (SEQ ID NO: 1), or the Hc vector, was constructed to harbor diverse populations of Hc antibody fragments. M13mp19 (Pharmacia, Piscataway, N.J.) was the starting vector. This vector was modified to contain, in addition to the encoded wild type M13 gene VIII: (1) a pseudo-wild type gene VIII sequence with an amber stop codon between it and the restriction sites for cloning oligonucleotides; (2) Stu I restriction site for insertion of sequences by hybridization and, Spe I and Xho I restriction sites in-frame with the pseudo-wild type gene VIII for cloning Hc sequences; (3) sequences necessary for expression, such as a promoter, signal sequence and translation initiation signals; (4) two pairs of Hind III-Mlu I sites for random joining of Hc and Lc vector portions, and (5) various other mutations to remove redundant restriction sites and the amino terminal portion of Lac Z.

Construction of M13IX30 was performed in four steps. In the first step, an M13-based vector containing the pseudo gVIII and various other mutations was constructed, M13IX01F. The second step involved the construction of a small cloning site in a separate M13mp18 vector to yield M13IX03. This vector was then expanded to contain expression sequences and restriction sites for Hc sequences to form M13IX04B. The fourth and final step involved the incorporation of the newly constructed sequences in M13IX04B into M13IX01F to yield M13IX30.

Construction of M13IX01F first involved the generation of a pseudo wild-type gVIII sequence for surface expression of antibody fragments. The pseudo-wild type gene encodes the identical amino acid sequence as that of the wild type gene; however, the nucleotide sequence has been altered so that only 63% identity exists between this gene and the encoded wild type gene VIII. Modification of the gene VIII nucleotide sequence used for surface expression reduces the possibility of homologous recombination with the wild type gene VIII contained on the same vector. Additionally, the wild type M13 gene VIII was retained in the vector system to ensure that at least some functional, non-fusion coat protein would be produced. The inclusion of wild type gene VIII facilitates the growth of phage under conditions where there is surface expression of the polypeptides and therefore reduces the possibility of non-viable phage production from the fusion genes.

The pseudo-wild type gene VIII was constructed by chemically synthesizing a series of oligonucleotides which encode both strands of the gene. The oligonucleotides are presented in Table III.

TABLE III

Pseudo-Wild Type Gene VIII Oligonucleotide Series

Sequence (5' to 3')

Top Strand Oligonucleotides

| | |
|---|---|
| VIII 03 | GATCC TAG GCT GAA GGC GAT GAC CCT GCT AAG GCT GC |
| VIII 04 | A TTC AAT AGT TTA CAG GCA AGT GCT ACT GAG TAC A |
| VIII 05 | TT GGC TAC GCT TGG GCT ATG GTA GTA GTT ATA GTT |
| VIII 06 | GGT GCT ACC ATA GGG ATT AAA TTA TTC AAA AAG TT |
| VIII 07 | T ACG AGC AAG GCT TCT TA |

Bottom Strand Oligonucleotides

| | |
|---|---|
| VIII 08 | AGC TTA AGA AGC CTT GCT CGT AAA CTT TTT GAA TAA TTT |
| VIII 09 | AAT CCC TAT GGT AGC ACC AAC TAT AAC TAC TAC CAT |
| VIII 10 | AGC CCA AGC GTA GCC AAT GTA CTC AGT AGC ACT TG |
| VIII 11 | C CTG TAA ACT ATT GAA TGC AGC CTT AGC AGG GTC |
| VIII 12 | ATC GCC TTC AGC CTA G |

Except for the terminal oligonucleotides VIII 03 (SEQ ID NO: 27) and VIII 08 (SEQ ID NO: 32), the above oligonucleotides (oligonucleotides VIII 04–07 (SEQ ID NOS: 28 through 31, respectively) and VIII 09–12 (SEQ ID NOS: 33 through 36, respectively)) were mixed at 200 ng each in 10 μl final volume, phosphorylated with T4 polynucleotide Kinase (Pharmacia) and 1 mM ATP at 37° C. for 1 hour, heated to 70° C. for 5 minutes, and annealed into double-stranded form by heating to 65° C. for 3 minutes, followed by cooling to room temperature over a period of 30 minutes. The reactions were treated with 1.0 U of T4 DNA ligase (BRL) and 1 mM ATP at room temperature for 1 hour, followed by heating to 70° C. for 5 minutes. Terminal oligonucleotides were then annealed to the ligated oligonucleotides. The annealed and ligated oligonucleotides yielded a double-stranded DNA flanked by a Bam HI site at its 5' end and by a Hind III site at its 3' end. A translational stop codon (amber) immediately follows the Bam HI site. The gene VIII sequence begins with the codon GAA (Glu) two codons 3' to the stop codon. The double-stranded insert was cloned in frame with the Eco RI and Sac I sites within the M13 polylinker. To do so, M13mpl19 was digested with Bam HI (New England Biolabs, Beverley, Mass.) and Hind III (New England Biolabs) and combined at a molar ratio of 1:10 with the double-stranded insert. The ligations were performed at room temperature overnight in 1×ligase buffer (50 mM Tris-HCl, pH 7.8, 10 mM MgCl$_2$, 20 mM DTT, 1 mM ATP, 50 μg/ml BSA) containing 1.0 U of T4 DNA ligase (New England Biolabs). The ligation mixture was transformed into a host and screened for positive clones using standard procedures in the art.

Several mutations were generated within the construct to yield functional M13IX01F. The mutations were generated using the method of Kunkel et al., Meth. Enzymol. 154:367–382 (1987), which is incorporated herein by reference, for site-directed mutagenesis. The reagents, strains and protocols were obtained from a Bio Rad Mutagenesis kit (Bio Rad, Richmond, Calif.) and mutagenesis was performed as recommended by the manufacturer.

Two Fok I sites were removed from the vector as well as the Hind III site at the end of the pseudo gene VIII sequence using the mutant oligonucleotides 5'-CATTTTTGCAGATGGCTTAGA-3' (SEQ ID NO: 37) and 5'-TAGCATTAACGTCCAATA-3' (SEQ ID NO: 38). New Hind III and Mlu I sites were also introduced at position 3919 and 3951 of M13IX01F. The oligonucleotides used for this mutagenesis had the sequences 5'-ATATATTTTAGTAAGCTTCATCTTCT-3' (SEQ ID NO: 39) and 5'-GACAAAGAACGCGTGAAAACTTT-3' (SEQ ID NO: 40), respectively. The amino terminal portion of Lac Z was deleted by oligonucleotide-directed mutagenesis using the mutant oligonucleotide 5'-GCGGG CCTCTTCGCTATTGCTTAAGAAGCCTTGCT-31' (SEQ ID NO: 41). In constructing the above mutations, all changes made in a M13 coding region were performed such that the amino acid sequence remained unaltered. The resultant vector, M13IX01F, was used in the final step to construct M13IX30 (see below).

In the second step, M13mp18 was mutated to remove the 5' end of Lac Z up to the Lac i binding site and including the Lac Z ribosome binding site and start codon. Additionally, the polylinker was removed and a Mlu I site was introduced in the coding region of Lac Z. A single oligonucleotide was used for these mutagenesis and had the sequence 5 '-AAACGACGGCCAGTGCCAAGTGACGCGTGTGAA ATTGTTATCC-3' (SEQ ID NO: 42). Restriction enzyme sites for Hind III and Eco RI were introduced downstream of the Mlu I site using the oligonucleotide 5 '-GGC GAAAGGGAATTCTGCAAGGCGATTAAGCTTGGG TAACGCC-3' (SEQ ID NO. 43). These modifications of M13mp18 yielded the precursor vector M13IX03.

The expression sequences and cloning sites were introduced into M13IX03 by chemically synthesizing a series of oligonucleotides which encode both strands of the desired sequence. The oligonucleotides are presented in Table IV.

TABLE IV

M13IX30 Oligonucleotide Series

| Top Strand Oligonucleotides | Sequence (5' to 3') |
| --- | --- |
| 084 | GGCGTTACCCAAGCTTTGTACATGGAGAAAATAAAG |
| 027 | TGAAACAAAGCACTATTGCACTGGCACTCTTACCGT TACCGT |
| 028 | TACTGTTTACCCCTGTGACAAAAGCCGCCCAGGTCC AGCTGC |
| 029 | TCGAGTCAGGCCTATTGTGCCCAGGGATTGTACTAG TGGATCCG |

| Bottom Oligonucleotides | Sequence (5' to 3') |
| --- | --- |
| 085 | TGGCGAAAGGGAATTCGGATCCACTAGTACAATCCCTG |
| 031 | GGCACAATAGGCCTGACTCGAGCAGCTGGACCAGGGCG GCTT |
| 032 | TTGTCACAGGGGTAAACAGTAACGGTAACGGTAAGTGT GCCA |
| 033 | GTGCAATAGTGCTTTGTTTCACTTTATTTTCTCCATGT ACAA |

The above oligonucleotides of Table IV, except for the terminal oligonucleotides 084 (SEQ ID NO: 44) and 085 (SEQ ID NO: 48), were mixed, phosphorylated, annealed and ligated to form a double-stranded insert as described in Example I. However, instead of cloning directly into the intermediate vector the insert was first amplified by PCR. The terminal oligonucleotides were used as primers for PCR. Oligonucleotide 084 (SEQ ID NO: 44) contains a Hind III site, 10 nucleotides internal to its 5' end and oligonucleotide 085 (SEQ ID NO: 48) has an Eco RI site at its 5' end. Following amplification, the products were restricted with Hind III and Eco RI and ligated, as described in Example I, into the polylinker of M13mp18 digested with the same two enzymes. The resultant double stranded insert contained a ribosome binding site, a translation initiation codon followed by a leader sequence and three restriction enzyme sites for cloning random oligonucleotides (Xho I, Stu I, Spe I). The intermediate vector was named M13IX04.

During cloning of the double-stranded insert, it was found that one of the GCC codons in oligonucleotides 028 and its complement in 031 was deleted. Since this deletion did not affect function, the final construct is missing one of the two GCC codons. Additionally, oligonucleotide 032 (SEQ ID NO: 50) contained a GTG codon where a GAG codon was needed. Mutagenesis was performed using the oligonucleotide 5'-TAACGGTAAGAGTGCCAGTGC-3' (SEQ ID NO: 52) to convert the codon to the desired sequence. The resultant vector is named M13IX04B.

The third step in constructing M13IX30 involved inserting the expression and cloning sequences from M13IX04B upstream of the pseudo wild-type gVIII in M13IX01F. This was accomplished by digesting M13IX04B with Dra III and Bam HI and gel isolating the 700 base pair insert containing the sequences of interest. M13IX01F was likewise digested with Dra III and Bam HI. The insert was combined with the double digested vector at a molar ratio of 1:1 and ligated as described in Example I. The sequence of the final construct M13IX30, is shown in FIG. 2A, 2B and 2C (SEQ ID NO: 1). FIG. 1A also shows M13IX30 where each of the elements necessary for surface expression of Hc fragments is marked. It should be noted during modification of the vectors, certain sequences differed from the published sequence of M13mp18. The new sequences are incorporated into the sequences recorded herein.

M13IX11 (SEQ ID NO: 2), or the Lc vector, was constructed to harbor diverse populations of Lc antibody fragments. This vector was also constructed from M13mp19 and contains: (1) sequences necessary for expression, such as a promoter, signal sequence and translation initiation signals; (2) Eco RV restriction site for insertion of sites for cl hybridization and Sac I and Xba I restriction sites for cloning of Lc sequences; (3) two pairs of Hind III-Mlu I sites for random joining of Hc and Lc vector portions, and (4) various other mutation to remove redundant restriction sites.

The expression, translation initiation signals, cloning sites, and one of the Mlu I sites were constructed by annealing of overlapping oligonucleotides as described above to produce a double-stranded insert containing a 5' Eco RI site and a 3' Hind III site. The overlapping oligonucleotides are shown in Table V and were ligated as a double-stranded insert between the Eco RI and Hind III sites of M13mp18 as described for the expression sequences inserted into M13IX03. The ribosome binding site (AGGAGAC) is located in oligonucleotide 015 and the translation initiation codon (ATG) is the first three nucleotides of oligonucleotide 016 (SEQ ID NO: 55).

TABLE V

| Oligonucleotide Series for Construction of Translation Signals in M13IX11 | |
| --- | --- |
| Oligonucleotide | Sequence (5' to 3') |
| 082 | CACC TTCATG AATTC GGC AAG GAGACA GTCAT |
| 015 | AATT C GCC AAG GAG ACA GTC AT |
| 016 | AATG AAA TAC CTA TTG CCT ACG GCA GCC GCT GGA TTG TT |
| 017 | ATTA CTC GCT GCC CAA CCA GCC ATG GCC GAG CTC GTG AT |
| 018 | GACC CAG ACT CCA GATATC CAA CAG GAA TGA GTG TTA AT |
| 019 | TCT AGA ACG CGT C |
| 083 | TTCAGGTTGAAGC TTA CGC GTT CTA GAA TTA ACA CTC ATT CCTGT |
| 021 | TG GAT ATC TGG AGT CTG GGT CAT CAC GAG CTC GGC CAT G |
| 022 | GC TGG TTG GGC AGC GAG TAA TAA CAA TCC AGC GGC TGC C |
| 023 | GT AGG CAA TAG GTA TTT CAT TAT GAC TGT CCT TGG CG |

Oligonucleotide 017 (SEQ ID NO: 56) contained a Sac I restriction site 67 nucleotides downstream from the ATG codon. The naturally occurring Eco RI site was removed and new Eco RI and Hind III sites were introduced downstream from the Sac I. Oligonucleotides 5'-TGACTG TCTCCTTGGCGTGTGAAATTGTTA-3' (SEQ ID NO: 63) and 5'-TAACACTCATTCCGGATGGAATTCTGGAGT CTGGGT-3' (SEQ ID NO: 64) were used to generate each of the mutations, respectively. The Lac Z ribosome binding site was removed when the original Eco RI site in M13mp19 was mutated. Additionally, when the new Eco RI and Hind III sites were generated, a spontaneous 100 bp deletion was found just 3' to these sites. Since the deletion does not affect the function, it was retained in the final vector.

In addition to the above mutations, a variety of other modifications were made to incorporate or remove certain sequences. The Hind III site used to ligate the double-stranded insert was removed with the oligonucleotide 5'-GCCAGTGCCAAGTGACGCGTTCTA-3' (SEQ ID NO: 65). Second Hind III and Mlu I sites were introduced at positions 3922 and 3952, respectively, using the oligonucleotides 5'-ATATATTTTAGTAAGCTTCATCTTCT-3' (SEQ ID NO: 66) for the Hind III mutagenesis and 5'-GACAAAGAACGCGTGAAAACTTT-3' (SEQ ID NO: 67) for the Mlu I mutagenesis. Again, mutations within the coding region did not alter the amino acid sequence.

The sequence of the resultant vector, M13IX11, is shown in FIG. 3A, 3B and 3C (SEQ ID NO: 2). FIG. 1B also shows M13IX11 where each of the elements necessary for producing a surface expression library between Lc fragments is marked.

Library Construction

Each population of Hc and Lc sequences synthesized by PCR above are separately cloned into M13IX30 and M13IX11, respectively, to create Hc and Lc libraries.

The Hc and Lc products (5 μg) are mixed, ethanol precipitated and resuspended in 20 μl of NaOAc buffer (33 mM Tris acetate, pH 7.9, 10 mM Mg-acetate, 66 mM K-acetate, 0.5 mM DTT). Five units of T4 DNA polymerase is added and the reactions incubated at 30° C. for 5 minutes to remove 3' termini by exonuclease digestion. Reactions are stopped by heating at 70° C. for 5 minutes. M13IX30 is digested with Stu I and M13IX11 is digested with Eco RV. Both vectors are treated with T4 DNA polymerase as described above and combined with the appropriate PCR products at a 1:1 molar ratio at 10 ng/μl to anneal in the above buffer at room temperature overnight. DNA from each annealing is electroporated into MK30-3 (Boehringer, Indianapolis, Ind.), as described below, to generate the Hc and Lc libraries.

E. coli MK30-3 is electroporated as described by Smith et al., Focus 12:38–40 (1990) which is incorporated herein by reference. The cells are prepared by inoculating a fresh colony of MK30-3 into 5 mls of SOB without magnesium (20 g bacto-tryptone, 5 g bacto-yeast extract, 0.584 g NaCl, 0.186 g KCl, dH$_2$O to 1,000 mls) and grown with vigorous aeration overnight at 37° C. SOB without magnesium (500 ml) is inoculated at 1:1000 with the overnight culture and grown with vigorous aeration at 37° C. until the OD$_{550}$ is 0.8 (about 2 to 3 h). The cells are harvested by centrifugation at 5,000 rpm (2,600×g) in a GS3 rotor (Sorvall, Newtown, Conn.) at 4° C. for 10 minutes, resuspended in 500 ml of ice-cold 10% (v/v) sterile glycerol, centrifuged and resuspended a second time in the same manner. After a third centrifugation, the cells are resuspended in 10% sterile glycerol at a final volume of about 2 ml, such that the OD$_{550}$ of the suspension was 200 to 300. Usually, resuspension is achieved in the 10% glycerol that remained in the bottle after pouring off the supernate. Cells are frozen in 40 μl aliquots in microcentrifuge tubes using a dry ice-ethanol bath and stored frozen at −70° C.

Frozen cells are electroporated by thawing slowly on ice before use and mixing with about 10 pg to 500 ng of vector per 40 μl of cell suspension. A 40 μl aliquot is placed in an 0.1 cm electroporation chamber (Bio-Rad, Richmond, Calif.) and pulsed once at 0° C. using 4 kΩ parallel resistor 25 μF, 1.88 KV, which gives a pulse length (τ) of ~4 ms. A 10 μl aliquot of the pulsed cells are diluted into 1 ml SOC (98 mls SOB plus 1 ml of 2M MgCl$_2$ and 1 ml of 2M glucose) in a 12-×75-mm culture tube, and the culture is shaken at 37° C. for 1 hour prior to culturing in selective media, (see below).

Each of the libraries are cultured using methods known to one skilled in the art. Such methods can be found in Sanbrook et al., Molecular Cloning: A Laboratory Manuel, Cold Spring Harbor Laboratory, Cold Spring Harbor, 1989, and in Ausubel et al., Current Protocols in Molecular Biology, John Wiley and Sons, New York, 1989, both of which are incorporated herein by reference. Briefly, the above 1 ml library cultures are grown up by diluting 50-fold into 2XYT media (16 g tryptone, 10 g yeast extract, 5 g NaCl) and culturing at 37° C. for 5–8 hours. The bacteria are pelleted by centrifugation at 10,000×g. The supernatant containing phage is transferred to a sterile tube and stored at 4° C.

Double strand vector DNA containing Hc and Lc antibody fragments are isolated from the cell pellet of each library. Briefly, the pellet is washed in TE (10 mM Tris, pH 8.0, 1 mM EDTA) and recollected by centrifugation at 7,000 rpm for 5' in a Sorval centrifuge (Newtown, Conn.). Pellets are resuspended in 6 mls of 10% Sucrose, 50 mM Tris, pH 8.0. 3.0 ml of 10 mg/μl lysozyne is added and incubated on ice for 20 minutes. 12 mls of 0.2M NaOH, 1% SDS is added followed by 10 minutes on ice. The suspensions are then incubated on ice for 20 minutes after addition of 7.5 mls of 3M NaOAc, pH 4.6. The samples are centrifuged at 15,000 rpm for 15 minutes at 4° C., RNased and extracted with phenol/chloroform, followed by ethanol precipitation. The pellets are resuspended, weighed and an equal weight of CsCl$_2$ is dissolved into each tube until a density of 1.60 g/ml is achieved. EtBr is added to 600 μg/ml and the double-stranded DNA is isolated by equilibrium centrifugation in a TV-1665 rotor (Sorval) at 50,000 rpm for 6 hours. These DNAs from each right and left half sublibrary are used to generate forty libraries in which the right and left halves of the randomized oligonucleotides have been randomly joined together.

The surface expression library is formed by the random joining of the Hc containing portion of M13IX30 with the Lc containing portion of M13IX11. The DNAs isolated from each library was digested separately with an excess amount of restriction enzyme. The Lc population (5 μg) is digested with Hind III. The Hc (5 μg) population is digested with Mlu I. The reactions are stopped by phenol/chloroform extraction followed by ethanol precipitation. The pellets are washed in 70% ethanol and resuspended in 20 μl of NaOAc buffer. Five units of T4 DNA polymerase (Pharmacia) is added and the reactions incubated at 30° C. for 5 minutes. Reactions are stopped by heating at 70° C. for 5 minutes. The Hc and Lc DNAs are mixed to a final concentration of 10 ng each vector/μl and allowed to anneal at room temperature overnight. The mixture is electroporated into MK30-3 cells as described above.

Screening of Surface Expression Libraries

Purified phage are prepared from 50 ml liquid cultures of XL1 Blue™ cells (Stratagene, La Jolla, Calif.) which had been infected at a m.o.i. of 10 from the phage stocks stored at 4° C. The cultures are induced with 2 mM IPTG. Supernatants are cleared by two centrifugations, and the phage are precipitated by adding 1/7.5 volumes of PEG solution (25% PEG-8000, 2.5M NaCl), followed by incubation at 4° C. overnight. The precipitate is recovered by centrifugation for 90 minutes at 10,000×g. Phage pellets are resuspended in 25 ml of 0.01M Tris-HCl, pH 7.6, 1.0 mM EDTA, and 0.1% Sarkosyl and then shaken slowly at room temperature for 30 minutes. The solutions are adjusted to 0.5M NaCl and to a final concentration of 5% polyethylene glycol. After 2 hours at 4° C., the precipitates containing the phage are recovered by centrifugation for 1 hour at 15,000×g. The precipitates are resuspended in 10 ml of NET buffer (0.1M NaCl, 1.0 mM EDTA, and 0.01M Tris-HCl, pH 7.6), mixed well, and the phage repelleted by centrifugation at 170,000×g for 3 hours. The phage pellets are resuspended overnight in 2 ml of NET buffer and subjected to cesium chloride centrifugation for 18 hours at 110,000×g (3.86 g of cesium chloride in 10 ml of buffer). Phage bands are collected, diluted 7-hold with NET buffer, recentrifuged at 170,000×g for 3 hours, resuspended, and stored at 4° C. in 0.3 ml of NET buffer containing 0.1 mM sodium azide.

The BDP used for panning on streptavidin coated dishes is first biotinylated and then absorbed against UV-inactivated blocking phage (see below). The biotinylating reagents are dissolved in dimethylformamide at a ratio of 2.4 mg solid NHS-SS-Biotin (sulfosuccinimidyl 2-(biotinamido) ethyl-1,3'-dithiopropionate; Pierce, Rockford, Ill.) to 1 ml solvent and used as recommended by the manufacturer. Small-scale reactions are accomplished by mixing 1 $\mu$l dissolved reagent with 43 $\mu$l of 1 mg/ml BDP diluted in sterile bicarbonate buffer (0.1M $NaHCO_3$, pH 8.6). After 2 hours at 25° C., residual biotinylating reagent is reacted with 500 $\mu$l 1M ethanolamine (pH adjusted to 9 with HCl) for an additional 2 hours. The entire sample is diluted with 1 ml TBS containing 1 mg/ml BSA, concentrated to about 50 $\mu$l on a Centricon 30 ultra-filter (Amicon), and washed on the same filter three times with 2 ml TBS and once with 1 ml TBS containing 0.02% $NaN_3$ and $7\times10^{12}$ UV-inactivated blocking phage (see below); the final retentate (60–80 $\mu$l) is stored at 4° C. BDP biotinylated with the NHS-SS-Biotin reagent is linked to biotin via a disulfide-containing chain.

UV-irradiated M13 phage are used for blocking any biotinylated BDP which fortuitously binds filamentous phage in general. M13mp8 (Messing and Vieira, Gene 19: 262–276 (1982), which is incorporated herein by reference) is chosen because it carries two amber mutations, which ensure that the few phage surviving irradiation will not grow in the sup O strains used to titer the surface expression library. A 5 ml sample containing $5\times10^{13}$ M13mp8 phage, purified as described above, is placed in a small petri plate and irradiated with a germicidal lamp at a distance of two feet for 7 minutes (flux 150 $\mu W/cm^2$). $NaN_3$ is added to 0.02% and phage particles concentrated to $10^{14}$ particles/ml on a Centricon 30-kDa ultrafilter (Amicon).

For panning, polystyrene petri plates (60×15 mm) are incubated with 1 ml of 1 mg/ml of streptavidin (BRL) in 0.1M $NaHCO_3$ pH 8.6–0.02% $NaN_3$ in a small, air-tight plastic box overnight in a cold room. The next day streptavidin is removed and replaced with at least 10 ml blocking solution (29 mg/ml of BSA; 3 $\mu$g/ml of streptavidin; 0.1M $NaHCO_3$ pH 8.6–0.02% $NaN_3$) and incubated at least 1 hour at room temperature. The blocking solution is removed and plates are washed rapidly three times with Tris buffered saline containing 0.5% Tween 20 (TBS-0.5% Tween 20).

Selection of phage expressing antibody fragments which bind BDP is performed with 5 $\mu$l (2.7 $\mu$g BDP) of blocked biotinylated BDP reacted with a 50 $\mu$l portion of the library. Each mixture is incubated overnight at 4° C., diluted with 1 ml TBS-0.5% Tween 20, and transferred to a streptavidin-coated petri plate prepared as described above. After rocking 10 minutes at room temperature, unbound phage are removed and plates washed ten times with TBS-0.5% Tween 20 over a period of 30–90 minutes. Bound phage are eluted from plates with 800 $\mu$l sterile elution buffer (1 mg/ml BSA, 0.1M HCl, pH adjusted to 2.2 with glycerol) for 15 minutes and eluates neutralized with 48 $\mu$l 2M Tris (pH unadjusted). A 20 $\mu$l portion of each eluate is titered on MK30-3 concentrated cells with dilutions of input phage.

A second round of panning is performed by treating 750 $\mu$l of first eluate from the library with 5 mM DTT for 10 minutes to break disulfide bonds linking biotin groups to residual biotinylated binding proteins. The treated eluate is concentrated on a Centricon 30 ultrafilter (Amicon), washed three times with TBS-0.5% Tween 20, and concentrated to a final volume of about 50 $\mu$l. Final retentate is transferred to a tube containing 5.0 $\mu$l (2.7 $\mu$g BDP) blocked biotinylated BDP and incubated overnight. The solution is diluted with 1 ml TBS-0.5% Tween 20, panned, and eluted as described above on fresh streptavidin-coated petri plates. The entire second eluate (800 $\mu$l) is neutralized with 48 $\mu$l 2M Tris, and 20 $\mu$l is titered simultaneously with the first eluate and dilutions of the input phage. If necessary, further rounds of panning can be performed to obtain homogeneous populations of phage. Additionally, phage can be plaque purified if reagents are available for detection.

Template Preparation and Sequencing

Templates are prepared for sequencing by inoculating a 1 ml culture of 2XYT containing a 1:100 dilution of an overnight culture of XL1 with an individual plaque from the purified population. The plaques are picked using a sterile toothpick. The culture is incubated at 37° C. for 5–6 hours with shaking and then transferred to a 1.5 ml microfuge tube. 200 $\mu$l of PEG solution is added, followed by vortexing and placed on ice for 10 minutes. The phage precipitate is recovered by centrifugation in a microfuge at 12,000×g for 5 minutes. The supernatant is discarded and the pellet is resuspended in 230 $\mu$l of TE (10 mM Tris-HCl, pH 7.5, 1 mM EDTA) by gently pipeting with a yellow pipet tip. Phenol (200 $\mu$l) is added, followed by a brief vortex and microfuged to separate the phases. The aqueous phase is transferred to a separate tube and extracted with 200 $\mu$l of phenol/chloroform (1:1) as described above for the phenol extraction. A 0.1 volume of 3M NaOAc is added, followed by addition of 2.5 volumes of ethanol and precipated at –20° C. for 20 minutes. The precipitated templates are recovered by centrifugation in a microfuge at 12,000×g for 8 minutes. The pellet is washed in 70% ethanol, dried and resuspended in 25 $\mu$l TE. Sequencing was performed using a Sequenase™ sequencing kit following the protocol supplied by the manufacturer (U.S. Biochemical, Cleveland, Ohio).

EXAMPLE II

Cloning of Heavy and Light Chain Sequences Without Restriction Enzyme Digestion

This example shows the simultaneous incorporation of antibody heavy and light chain fragment encoding sequences into a M13IXHL-type vector with the use of restriction endonucleases.

For the simultaneous incorporation of heavy and light chain encoding sequences into a single coexpression vector, a M13IXHL vector was produced that contained heavy and light chain encoding sequences for a mouse monoclonal antibody (DAN-18H4; Biosite, San Diego, Calif.). The inserted antibody fragment sequences are used as complementary sequences for the hybridization and incorporation of Hc and Lc sequences by site-directed mutagenesis. The genes encoding the heavy and light chain polypeptides were inserted into M13IX30 (SEQ ID NO: 1) and M13IX11 (SEQ ID NO: 2), respectively, and combined into a single surface expression vector as described in Example I. The resultant M13IXHL-type vector is termed M13IX50.

The combinations were performed under conditions that facilitate the formation of one Hc and one Lc vector half into a single circularized vector. Briefly, the overhangs generated between the pairs of restriction sites after restriction with Mlu I or Hind III and exonuclease digestion are unequal (i.e., 64 nucleotides compared to 32 nucleotides). These unequal lengths result in differential hybridization temperatures for specific annealing of the complementary ends from each vector. The specific hybridization of each end of each vector half was accomplished by first annealing at 65° C. in a small volume (about 100 μg/μl) to form a dimer of one Hc vector half and one Lc vector half. The dimers were circularized by diluting the mixture (to about 20 μg/μl) and lowering the temperature to about 25°–370° C. to allow annealing. T4 ligase was present to covalently close the circular vectors.

M13IX50 was modified such that it did not produce a functional polypeptide for the DAN monoclonal antibody. To do this, about eight amino acids were changed within the variable region of each chain by mutagenesis. The Lc variable region was mutagenized using the oligonucleotide 5'-CTGAACCTGTCTGGGACCACAGTTGATGCTATA GGATCAGATCTAGAATTCATT TAGAGACTGGCCTGGCTTCTGC-3' (SEQ ID NO: 68). The Hc sequence was mutagenized with the oligonucleotide 5'-TCGACCGTTGGTAGGAATAATGCAATTAATG GAGTAGCTCTAAATTCAGAATTCATCTACACCCAG TGCATCCAGTAGCT-31' (SEQ ID NO: 69). An additional mutation was also introduced into M13IX50 to yield the final form of the vector. During construction of an intermediate to M13IX50 (M13IX04 described in Example I), a six nucleotide sequence was duplicated in oligonucleotide 027 and its complement 032. This sequence, 5'-TTACCG-3' was deleted by mutagenesis using the oligonucleotide 5'-GGTAAACAGTAACGGTAAGAGTGCCAG-3' (SEQ ID NO: 70). The resultant vector was designated M13IX53.

M13IX53 can be produced as a single stranded form and contains all the functional elements of the previously described M13IXHL vector except that it does not express functional antibody heteromers. The single-stranded vector can be hybridized to populations of single-stranded Hc and Lc encoding sequences for their incorporation into the vector by mutagenesis. Populations of single-stranded Hc and Lc encoding sequences can be produced by one skilled in the art from the PCR products described in Example I or by other methods known to one skilled in the art using the primers and teachings described therein. The resultant vectors with Hc and Lc encoding sequences randomly incorporated are propagated and screened for desired binding specificities as described in Example I.

Other vectors similar to M13IX53 and the vectors it's derived from, M13IX11 and M13IX30, have also been produced for the incorporation of Hc and Lc encoding sequences without restriction. In contrast to M13IX53, these vectors contain human antibody sequences for the efficient hybridization and incorporation of populations of human Hc and Lc sequences. These vectors are briefly described below. The starting vectors were either the Hc vector (M13IX30) or the Lc vector (M13IX11) previously described.

M13IX32 was generated from M13IX30 by removing the six nucleotide redundant sequence 5'-TTACCG-3' described above and mutation of the leader sequence to increase secretion of the product. The oligonucleotide used to remove the redundant sequence is the same as that given above. The mutation in the leader sequence was generated using the oligonucleotide 5'GGGCTTTTGCCACAGGGGT-3'. This mutagenesis resulted in the A residue at position 6353 of M13IX30 being changed to a G residue.

A decapeptide tag for affinity purification of antibody fragments was incorporated in the proper reading frame at the carboxy-terminal end of the Hc expression site in M13IX32. The oligonucleotide used for this mutagenesis was 5'-CGCCTTCAGCCTAAGAAGCGTAGTCCGGAA CGTCGTACGGGTAGGATCCA CTAG-3' (SEQ ID NO: 71). The resultant vector was designated M13IX33. Modifications to this or other vectors are envisioned which include various features known to one skilled in the art. For example, a peptidase cleavage site can be incorporated following the decapeptide tag which allows the antibody to be cleaved from the gene VIII portion of the fusion protein.

M13IX34 (SEQ ID NO: 3) was created from M13IX33 by cloning in the gene encoding a human IgGl heavy chain. The reading frame of the variable region was changed and a stop codon was introduced to ensure that a functional polypeptide would not be produced. The oligonucleotide used for the mutagenesis of the variable region was 5'-CACCGGTTCGGGGAATTAGTCTTGACCAGGCA GCCCAGGGC-3' (SEQ ID NO: 72). The complete nucleotide sequence of this vector is shown in FIG. 4A, 4B and 4C (SEQ ID NO: 3).

Several vectors of the M13IX11 series were also generated to contain similar modifications as that described for the vectors M13IX53 and M13IX34. The promoter region in M13IX11 was mutated to conform to the 35 consensus sequence to generate M13IX12. The oligonucleotide used for this mutagenesis was 5'-ATTCCACAC ATTATAC-GAGCCGGAAGCATAAAGTGTCAAGCCT GGGGTGCC-3' (SEQ ID NO: 73). A human kappa light chain sequence was cloned into M13IX12 and the variable region subsequently deleted to generate M13IX13 (SEQ ID NO: 4). The complete nucleotide sequence of this vector is shown in FIG. 5A, 5B and 5C (SEQ ID NO: 4). A similar vector, designated M13IX14, was also generated in which the human lambda light chain was inserted into M13IX12 followed by deletion of the variable region. The oligonucleotides used for the variable region deletion of M13IX13 and M13IX14 were 5'-CTG CTCATCAGATGGCGGG AAGAGCTCGGCCATGGCTGGTTG-3' (SEQ ID NO: 74) and 5'-GAACAGAGT GACCGAGGGGGCGAGCT CGGCCATGGCTGGTTG-31' (SEQ ID NO: 75), respectively.

The Hc and Lc vectors or modified forms thereof can be combined using the methods described in Example I to produce a single vector similar to M13IX53 that allows the efficient incorporation of human Hc and Lc encoding sequences by mutagenesis. An example of such a vector is the combination of M13IX13 with M13IX34. The complete nucleotide sequence of this vector, M13IX60, is shown in FIG. 6A, 6B and 6C (SEQ ID NO: 5).

Additional modifications to any of the previously described vectors can also be performed to generate vectors which allow the efficient incorporation and surface expression of Hc and Lc sequences. For example, to alleviate the use of uracil selection against wild-type template during mutagenesis procedures, the variable region locations within the vectors can be substituted by a set of palindromic restriction enzyme sites (i.e., two similar sites in opposite orientation). The palindromic sites will loop out and hybridize together during the mutagenesis and thus form a double-stranded substrate for restriction endonuclease digestion. Cleavage of the site results in the destruction of the wild-type template. The variable region of the inserted Hc or Lc sequences will not be affected since they will be in single stranded form.

Following the methods of Example I, single-stranded Hc or Lc populations can be produced by a variety of methods known to one skilled in the art. For example, the PCR primers described in Example I can be used in asymmetric PCR to generate such populations. Gelfand et al., "PCR Protocols: A Guide to Methods and Applications", Ed by M. A. Innis (1990), which is incorporated herein by reference. Asymmetric PCR is a PCR method that differentially amplifies only a single strand of the double stranded template. Such differential amplification is accomplished by decreasing the primer amount for the undesirable strand about 10-fold compared to that for the desirable strand. Alternatively, single-stranded populations can be produced from double-stranded PCR products generated as described in Example I except that the primer(s) used to generate the undesirable strand of the double-stranded products is first phosphorylated at its 5' end with a kinase. The resultant products can then be treated with a 5' to 3' exonuclease, such as lambda exonuclease (BRL, Bethesda, MD) to digest away the unwanted strand.

Single-stranded Hc and Lc populations generated by the methods described above or by others known to one skilled in the art are hybridized to complementary sequences encoded in the previously described vectors. The population of the sequences are subsequently incorporated into a double-stranded form of the vector by polymerase extension of the hybridized templates. Propagation and surface expression of the randomly combined Hc and Lc sequences are performed as described in Example I.

Although the invention has been described with reference to the presently preferred embodiment, it should be understood that various modifications can be made without departing from the spirit of the invention. Accordingly, the invention is limited only by the claims.

I claim:

1. A composition of matter comprising a plurality of cells containing only operatively combined vectors having diverse combinations of first and second DNA sequences encoding first and second polypeptides which form heteromeric receptors of the immunoglobulin superfamily, one or both of said polypeptides being expressed as fusion proteins on the surface of a cell or a bacteriophage, said operatively combined vectors being formed by the recombination of first and second vectors having two p airs of restriction sites symmetrically oriented about a cloning site for containing said first and second DNA sequences, said recombination effected between the two pairs of restriction sites.

2. The composition of claim 1, wherein said heteromeric receptors of the immunoglobulin superfamily are selected from the group consisting of antibodies and T cell receptors.

3. The composition of claim 1, wherein said first and second DNA sequences encode functional portions of heteromeric receptors of the immunoglobulin superfamily.

4. The composition of claim 1, wherein said plurality of cells is a plurality of prokaryotic cells.

5. The composition of claim 4, wherein said vectors are filamentous bacteriophage.

6. The composition of claim 5, wherein said plurality of cells are E. coli.

7. The composition of claim 5, wherein said cells produce said filamentous bacteriophage.

8. The composition of claim 7, wherein said filamentous bacteriophage are selected from the group consisting of M13, fd and fl.

9. The composition of claim 7, wherein at least one of the encoded first or second polypeptides is expressed as a fusion protein with gene VIII.

10. A composition of matter comprising a plurality of cells containing only operatively combined vectors having diverse combinations of first and second DNA sequences encoding functional portions of variable heavy and variable light chains of an antibody, one or both of said functional portions of said variable heavy and variable light chains being expressed as fusion proteins on the surface of a cell or a bacteriophage, said operatively combined vectors being formed by the recombination of first and second vectors having two pairs of restriction sites symmetrically oriented about a cloning site for containing said first and second DNA sequences, said recombination effected between the two pairs of restriction sites.

11. A cloning system for the coexpression of two or more DNA sequences encoding polypeptides which form a heteromeric receptor of the immunoglobulin superfamily, comprising a set of first vectors having a diverse population of first DNA sequences and a set of second vectors having a diverse population of second DNA sequences, said diverse populations of first and second DNA sequences encoding polypeptides which form heteromeric receptors of the immunoglobulin superfamily and said first and second vectors having two pairs of restriction sites symmetrically oriented about a cloning site for containing said first and second populations of DNA sequences so as to allow only the operational combination of vector sequences containing said first and second DNA sequences.

12. The cloning system of claim 11, wherein said first and second vectors are circular.

13. The cloning system of claim 11, wherein said heteromeric receptors of the immunoglobulin superfamily are selected from the group consisting of antibodies and T cell receptors.

14. The cloning system of claim 11, wherein said first and second DNA sequences encode functional binding portions of heteromeric receptors of the immunoglobulin superfamily.

15. The cloning system of claim 11, wherein said two pairs of restriction sites are Hind III-Mlu I and Hind III-Mlu I.

16. The cloning system of claim 11, wherein said coexpression of two or more DNA sequences encoding polypeptides which form a heteromeric receptor of the immunoglobulin superfamily is on the surface of a cell or a bacteriophage.

17. The cloning system of claim 16, wherein said first and second vectors are filamentous bacteriophage.

18. The cloning system of claim 17 wherein said filamentous bacteriophage are selected from the group consisting of M13, fd and fl.

19. The cloning system of claim 18, wherein at least one of the DNA sequences is expressed as a fusion protein with the protein product of gene VIII.

20. A cloning system for the coexpression of two or more DNA sequences encoding functional portions of variable heavy and variable light chains which form an antibody, comprising a set of first vectors having a diverse population of first DNA sequences and a set of second vectors having a diverse population of second DNA sequences, said first and second vectors having two pairs of restriction sites symmetrically oriented about a cloning site for containing said first and second populations of DNA sequences so as to allow only the operational combination of vector sequences containing said first and second DNA sequences.

21. A plurality of expression vectors containing a plurality of first and second DNA sequences encoding a plurality of first and second polypeptides, said expression vectors formed from two pairs of restriction sites symmetrically oriented about a cloning site for containing said first and second DNA sequences, wherein any random combination of a first DNA sequence and a second DNA sequence can only be operatively linked to encode first and second polypeptides that form a plurality of heteromeric receptors of the immunoglobulin superfamily, said plurality of heteromeric receptors of the immunoglobulin superfamily being characterized by at least one heteromeric receptor exhibiting binding activity toward a preselected molecule, said DNA sequences being further operatively linked to at least one gene encoding a surface protein of a cell or a bacteriophage.

22. The expression vectors of claim 21, wherein said expression vectors are circular.

23. The expression vectors of claim 21, wherein said heteromeric receptors of the immunoglobulin superfamily are selected from the group consisting of antibodies and T cell receptors.

24. The expression vectors of claim 23, wherein said first and second DNA sequences encode functional portions of heteromeric receptors of the immunoglobulin superfamily.

25. The expression vectors of claim 21, wherein said vectors are filamentous bacteriophage.

26. The expression vectors of claim 25, wherein said filamentous bacteriophage are produced in a prokaryotic cell.

27. The expression vectors of claim 26, wherein said filamentous bacteriophage are selected from the group consisting of M13, fd and fl.

28. The expression vectors of claim 27, wherein at least one of the encoded first or second polypeptides is expressed as a fusion protein with gene VIII.

29. A plurality of expression vectors containing a plurality of first and second DNA sequences encoding a plurality of functional portions of variable heavy and variable light chains of an antibody, said expression vectors formed from two pairs of restriction sites symmetrically oriented about a cloning site for containing said first and second DNA sequences, wherein any random combination of a first DNA sequence and a second DNA sequence can only be operatively linked to encode functional portions of the variable heavy and variable light chains of an antibody that form a plurality of antibodies, said plurality of antibodies being characterized by at least one antibody exhibiting binding activity toward a preselected molecule, said DNA sequences being further operatively linked to at least one gene encoding a surface protein of a cell or a bacteriophage.

30. A composition of matter comprising a plurality of cells containing only operatively combined vectors having diverse combinations of first and second DNA sequences encoding functional binding portions of the first chain and second chain of a T cell receptor, one or both of said functional binding portions of said first chain and second chain being expressed as fusion proteins on the surface of a cell or a bacteriophage, said operatively combined vectors being formed by the recombination of first and second vectors having two pairs of restriction sites symmetrically oriented about a cloning site for containing said first and second DNA sequences, said recombination effected between the two pairs of restriction sites.

31. A cloning system for the coexpression of two or more DNA sequences encoding functional binding portions of the first chain and second chain which form a T cell receptor, comprising a set of first vectors having a diverse population of first DNA sequences and a set of second vectors having a diverse population of second DNA sequences, said first and second vectors having two pairs of restriction sites symmetrically oriented about a cloning site for containing said first and second populations of DNA sequences so as to allow only the operational combination of vector sequences containing said first and second DNA sequences.

32. A plurality of expression vectors containing a plurality of first and second DNA sequences encoding a plurality of functional binding portions of the first chain and second chain of a T cell receptor, said expression vectors formed from two pairs of restriction sites symmetrically oriented about a cloning site for containing said first and second DNA sequences, wherein any random combination of a first DNA sequence and a second DNA sequence can only be operatively linked to encode functional binding portions of the first chain and second chain of a T cell receptor that form a plurality of T cell receptors, said plurality of T cell receptors being characterized by at least one T cell receptor exhibiting binding activity toward a preselected molecule, said DNA sequences being further operatively linked to at least one gene encoding a surface protein of a cell or a bacteriophage.

* * * * *

UNITED STATES PATENT AND TRADEMARK OFFICE
CERTIFICATE OF CORRECTION

PATENT NO. : 5,871,974
DATED : February 16, 1999
INVENTOR(S) : William D. Huse

It is certified that error appears in the above-identified patent and that said Letters Patent is hereby corrected as shown below:

Column 2,
Line 67, please delete "receptors be" and replace therefor -- receptors can be --.

Column 3,
Line 22, please delete "toward particular" and replace therefor -- toward a particular --.

Column 8,
Lines 41, 54, 57 and 60, please delete "HCL" and replace therefor -- HCl --.
Line 50, please delete "dH$_2$0The" and replace therefor -- dH$_2$0. The --

Column 9,
Line 5, please delete "HCL" and replace therefor -- HCl --.
Line 8, please delete "Md. Reverse" and replace therefor -- Md) Reverse --
Line 14, please delete "library is" and replace therefor -- library are --.

Column 10,
Line 42, please delete "M13TX30" and replace therefor -- M13IX30 --.

Column 16,
Line 52, please delete "was" and replace therefor -- were --.

Column 17,
Line 21, please delete "7-hold" and replace therefor -- 7-fold --.

Column 19,
Line 25, please delete "25º-370º C" and replace therefor -- 25º-37º C. --

UNITED STATES PATENT AND TRADEMARK OFFICE
CERTIFICATE OF CORRECTION

PATENT NO. : 5,871,974
DATED : February 16, 1999
INVENTOR(S) : William D. Huse

It is certified that error appears in the above-identified patent and that said Letters Patent is hereby corrected as shown below:

<u>Column 81,</u>
Line 12, please delete "23" and replace therefor -- 21 --.

Signed and Sealed this

Twenty-third Day of July, 2002

Attest:

Attesting Officer

JAMES E. ROGAN
*Director of the United States Patent and Trademark Office*

SEQUENCE LISTING ( 1 ) GENERAL INFORMATION:

( i i i ) NUMBER OF SEQUENCES: 75

( 2 ) INFORMATION FOR SEQ ID NO:1:

( i ) SEQUENCE CHARACTERISTICS:
( A ) LENGTH: 7445 base pairs
( B ) TYPE: nucleic acid
( C ) STRANDEDNESS: both
( D ) TOPOLOGY: circular ( x i ) SEQUENCE DESCRIPTION: SEQ ID NO:1:

```
AATGCTACTA  CTATTAGTAG  AATTGATGCC  ACCTTTTCAG  CTCGCGCCCC  AAATGAAAAT      60

ATAGCTAAAC  AGGTTATTGA  CCATTTGCGA  AATGTATCTA  ATGGTCAAAC  TAAATCTACT     120

CGTTCGCAGA  ATTGGGAATC  AACTGTTACA  TGGAATGAAA  CTTCCAGACA  CCGTACTTTA     180

GTTGCATATT  TAAAACATGT  TGAGCTACAG  CACCAGATTC  AGCAATTAAG  CTCTAAGCCA     240

TCTGCAAAAA  TGACCTCTTA  TCAAAGGAG   CAATTAAAGG  TACTCTCTAA  TCCTGACCTG     300

TTGGAGTTTG  CTTCCGGTCT  GGTTCGCTTT  GAAGCTCGAA  TTAAAACGCG  ATATTTGAAG     360

TCTTTCGGGC  TTCCTCTTAA  TCTTTTTGAT  GCAATCCGCT  TTGCTTCTGA  CTATAATAGT     420

CAGGGTAAAG  ACCTGATTTT  TGATTTATGG  TCATTCTCGT  TTTCTGAACT  GTTTAAAGCA     480

TTTGAGGGGG  ATTCAATGAA  TATTTATGAC  GATTCCGCAG  TATTGGACGC  TATCCAGTCT     540

AAACATTTTA  CTATTACCCC  CTCTGGCAAA  ACTTCTTTTG  CAAAAGCCTC  TCGCTATTTT     600

GGTTTTTATC  GTCGTCTGGT  AAACGAGGGT  TATGATAGTG  TTGCTCTTAC  TATGCCTCGT     660

AATTCCTTTT  GGCGTTATGT  ATCTGCATTA  GTTGAATGTG  GTATTCCTAA  ATCTCAACTG     720

ATGAATCTTT  CTACCTGTAA  TAATGTTGTT  CCGTTAGTTC  GTTTTATTAA  CGTAGATTTT     780

TCTTCCCAAC  GTCCTGACTG  GTATAATGAG  CCAGTTCTTA  AAATCGCATA  AGGTAATTCA     840

CAATGATTAA  AGTTGAAATT  AAACCATCTC  AAGCCCAATT  TACTACTCGT  TCTGGTGTTT     900

CTCGTCAGGG  CAAGCCTTAT  TCACTGAATG  AGCAGCTTTG  TTACGTTGAT  TTGGGTAATG     960
```

| | | | | | | |
|---|---|---|---|---|---|---|
| AATATCCGGT | TCTTGTCAAG | ATTACTCTTG | ATGAAGGTCA | GCCAGCCTAT | GCGCCTGGTC | 1020 |
| TGTACACCGT | TCATCTGTCC | TCTTTCAAAG | TTGGTCAGTT | CGGTTCCCTT | ATGATTGACC | 1080 |
| GTCTGCGCCT | CGTTCCGGCT | AAGTAACATG | GAGCAGGTCG | CGGATTTCGA | CACAATTTAT | 1140 |
| CAGGCGATGA | TACAAATCTC | CGTTGTACTT | TGTTTCGCGC | TTGGTATAAT | CGCTGGGGGT | 1200 |
| CAAAGATGAG | TGTTTTAGTG | TATTCTTTCG | CCTCTTTCGT | TTTAGGTTGG | TGCCTTCGTA | 1260 |
| GTGGCATTAC | GTATTTTACC | CGTTTAATGG | AAACTTCCTC | ATGAAAAAGT | CTTTAGTCCT | 1320 |
| CAAAGCCTCT | GTAGCCGTTG | CTACCCTCGT | TCCGATGCTG | TCTTTCGCTG | CTGAGGGTGA | 1380 |
| CGATCCCGCA | AAAGCGGCCT | TTAACTCCCT | GCAAGCCTCA | GCGACCGAAT | ATATCGGTTA | 1440 |
| TGCGTGGGCG | ATGGTTGTTG | TCATTGTCGG | CGCAACTATC | GGTATCAAGC | TGTTTAAGAA | 1500 |
| ATTCACCTCG | AAAGCAAGCT | GATAAACCGA | TACAATTAAA | GGCTCCTTTT | GGAGCCTTTT | 1560 |
| TTTTTGGAGA | TTTTCAACGT | GAAAAAATTA | TTATTCGCAA | TTCCTTTAGT | TGTTCCTTTC | 1620 |
| TATTCTCACT | CCGCTGAAAC | TGTTGAAAGT | TGTTTAGCAA | AACCCCATAC | AGAAAATTCA | 1680 |
| TTTACTAACG | TCTGGAAAGA | CGACAAAACT | TTAGATCGTT | ACGCTAACTA | TGAGGGTTGT | 1740 |
| CTGTGGAATG | CTACAGGCGT | TGTAGTTTGT | ACTGGTGACG | AAACTCAGTG | TTACGGTACA | 1800 |
| TGGGTTCCTA | TTGGGCTTGC | TATCCCTGAA | AATGAGGGTG | GTGGCTCTGA | GGGTGGCGGT | 1860 |
| TCTGAGGGTG | GCGGTTCTGA | GGGTGGCGGT | ACTAAACCTC | CTGAGTACGG | TGATACACCT | 1920 |
| ATTCCGGGCT | ATACTTATAT | CAACCCTCTC | GACGGCACTT | ATCCGCCTGG | TACTGAGCAA | 1980 |
| AACCCCGCTA | ATCCTAATCC | TTCTCTTGAG | GAGTCTCAGC | CTCTTAATAC | TTTCATGTTT | 2040 |
| CAGAATAATA | GGTTCCGAAA | TAGGCAGGGG | GCATTAACTG | TTTATACGGG | CACTGTTACT | 2100 |
| CAAGGCACTG | ACCCCGTTAA | AACTTATTAC | CAGTACACTC | CTGTATCATC | AAAAGCCATG | 2160 |
| TATGACGCTT | ACTGGAACGG | TAAATTCAGA | GACTGCGCTT | TCCATTCTGG | CTTTAATGAA | 2220 |
| GATCCATTCG | TTTGTGAATA | TCAAGGCCAA | TCGTCTGACC | TGCCTCAACC | TCCTGTCAAT | 2280 |
| GCTGGCGGCG | GCTCTGGTGG | TGGTTCTGGT | GGCGGCTCTG | AGGGTGGTGG | CTCTGAGGGT | 2340 |
| GGCGGTTCTG | AGGGTGGCGG | CTCTGAGGGA | GGCGGTTCCG | GTGGTGGCTC | TGGTTCCGGT | 2400 |
| GATTTTGATT | ATGAAAAGAT | GGCAAACGCT | AATAAGGGGG | CTATGACCGA | AAATGCCGAT | 2460 |
| GAAAACGCGC | TACAGTCTGA | CGCTAAAGGC | AAACTTGATT | CTGTCGCTAC | TGATTACGGT | 2520 |
| GCTGCTATCG | ATGGTTTCAT | TGGTGACGTT | TCCGGCCTTG | CTAATGGTAA | TGGTGCTACT | 2580 |
| GGTGATTTTG | CTGGCTCTAA | TTCCCAAATG | GCTCAAGTCG | GTGACGGTGA | TAATTCACCT | 2640 |
| TTAATGAATA | ATTTCCGTCA | ATATTTACCT | TCCCTCCCTC | AATCGGTTGA | ATGTCGCCCT | 2700 |
| TTTGTCTTTA | GCGCTGGTAA | ACCATATGAA | TTTTCTATTG | ATTGTGACAA | AATAAACTTA | 2760 |
| TTCCGTGGTG | TCTTTGCGTT | TCTTTTATAT | GTTGCCACCT | TTATGTATGT | ATTTTCTACG | 2820 |
| TTTGCTAACA | TACTGCGTAA | TAAGGAGTCT | TAATCATGCC | AGTTCTTTTG | GGTATTCCGT | 2880 |
| TATTATTGCG | TTTCCTCGGT | TTCCTTCTGG | TAACTTTGTT | CGGCTATCTG | CTTACTTTTC | 2940 |
| TTAAAAAGGG | CTTCGGTAAG | ATAGCTATTG | CTATTTCATT | GTTTCTTGCT | CTTATTATTG | 3000 |
| GGCTTAACTC | AATTCTTGTG | GGTTATCTCT | CTGATATTAG | CGCTCAATTA | CCCTCTGACT | 3060 |
| TTGTTCAGGG | TGTTCAGTTA | ATTCTCCCGT | CTAATGCGCT | TCCCTGTTTT | TATGTTATTC | 3120 |
| TCTCTGTAAA | GGCTGCTATT | TTCATTTTTG | ACGTTAAACA | AAAAATCGTT | TCTTATTTGG | 3180 |
| ATTGGGATAA | ATAATATGGC | TGTTTATTTT | GTAACTGGCA | AATTAGGCTC | TGGAAAGACG | 3240 |
| CTCGTTAGCG | TTGGTAAGAT | TCAGGATAAA | ATTGTAGCTG | GGTGCAAAAT | AGCAACTAAT | 3300 |
| CTTGATTTAA | GGCTTCAAAA | CCTCCCGCAA | GTCGGGAGGT | TCGCTAAAAC | GCCTCGCGTT | 3360 |

| | | | | | | |
|---|---|---|---|---|---|---|
| CTTAGAATAC | CGGATAAGCC | TTCTATATCT | GATTTGCTTG | CTATTGGGCG | CGGTAATGAT | 3420 |
| TCCTACGATG | AAAATAAAAA | CGGCTTGCTT | GTTCTCGATG | AGTGCGGTAC | TTGGTTTAAT | 3480 |
| ACCCGTTCTT | GGAATGATAA | GGAAAGACAG | CCGATTATTG | ATTGGTTTCT | ACATGCTCGT | 3540 |
| AAATTAGGAT | GGGATATTAT | TTTTCTTGTT | CAGGACTTAT | CTATTGTTGA | TAAACAGGCG | 3600 |
| CGTTCTGCAT | TAGCTGAACA | TGTTGTTTAT | TGTCGTCGTC | TGGACAGAAT | TACTTTACCT | 3660 |
| TTTGTCGGTA | CTTTATATTC | TCTTATTACT | GGCTCGAAAA | TGCCTCTGCC | TAAATTACAT | 3720 |
| GTTGGCGTTG | TTAAATATGG | CGATTCTCAA | TTAAGCCCTA | CTGTTGAGCG | TTGGCTTTAT | 3780 |
| ACTGGTAAGA | ATTTGTATAA | CGCATATGAT | ACTAAACAGG | CTTTTTCTAG | TAATTATGAT | 3840 |
| TCCGGTGTTT | ATTCTTATTT | AACGCCTTAT | TTATCACACG | GTCGGTATTT | CAAACCATTA | 3900 |
| AATTTAGGTC | AGAAGATGAA | GCTTACTAAA | ATATATTTGA | AAAGTTTTC | ACGCGTTCTT | 3960 |
| TGTCTTGCGA | TTGGATTTGC | ATCAGCATTT | ACATATAGTT | ATATAACCCA | ACCTAAGCCG | 4020 |
| GAGGTTAAAA | AGGTAGTCTC | TCAGACCTAT | GATTTTGATA | AATTCACTAT | TGACTCTTCT | 4080 |
| CAGCGTCTTA | ATCTAAGCTA | TCGCTATGTT | TTCAAGGATT | CTAAGGGAAA | ATTAATTAAT | 4140 |
| AGCGACGATT | TACAGAAGCA | AGGTTATTCA | CTCACATATA | TTGATTTATG | TACTGTTTCC | 4200 |
| ATTAAAAAAG | GTAATTCAAA | TGAAATTGTT | AAATGTAATT | AATTTTGTTT | CTTGATGTT | 4260 |
| TGTTTCATCA | TCTTCTTTTG | CTCAGGTAAT | TGAAATGAAT | AATTCGCCTC | TGCGCGATTT | 4320 |
| TGTAACTTGG | TATTCAAAGC | AATCAGGCGA | ATCCGTTATT | GTTTCTCCCG | ATGTAAAAGG | 4380 |
| TACTGTTACT | GTATATTCAT | CTGACGTTAA | ACCTGAAAAT | CTACGCAATT | TCTTTATTTC | 4440 |
| TGTTTTACGT | GCTAATAATT | TTGATATGGT | TGGTTCAATT | CCTTCCATAA | TTCAGAAGTA | 4500 |
| TAATCCAAAC | AATCAGGATT | ATATTGATGA | ATTGCCATCA | TCTGATAATC | AGGAATATGA | 4560 |
| TGATAATTCC | GCTCCTTCTG | GTGGTTTCTT | TGTTCCGCAA | AATGATAATG | TTACTCAAAC | 4620 |
| TTTTAAAATT | AATAACGTTC | GGGCAAAGGA | TTTAATACGA | GTTGTCGAAT | TGTTTGTAAA | 4680 |
| GTCTAATACT | TCTAAATCCT | CAAATGTATT | ATCTATTGAC | GGCTCTAATC | TATTAGTTGT | 4740 |
| TAGTGCACCT | AAAGATATTT | TAGATAACCT | TCCTCAATTC | CTTTCTACTG | TTGATTTGCC | 4800 |
| AACTGACCAG | ATATTGATTG | AGGGTTTGAT | ATTTGAGGTT | CAGCAAGGTG | ATGCTTTAGA | 4860 |
| TTTTTCATTT | GCTGCTGGCT | CTCAGCGTGG | CACTGTTGCA | GGCGGTGTTA | ATACTGACCG | 4920 |
| CCTCACCTCT | GTTTTATCTT | CTGCTGGTGG | TTCGTTCGGT | ATTTTTAATG | GCGATGTTTT | 4980 |
| AGGGCTATCA | GTTCGCGCAT | TAAAGACTAA | TAGCCATTCA | AAAATATTGT | CTGTGCCACG | 5040 |
| TATTCTTACG | CTTTCAGGTC | AGAAGGGTTC | TATCTCTGTT | GGCCAGAATG | TCCCTTTTAT | 5100 |
| TACTGGTCGT | GTGACTGGTG | AATCTGCCAA | TGTAAATAAT | CCATTTCAGA | CGATTGAGCG | 5160 |
| TCAAAATGTA | GGTATTTCCA | TGAGCGTTTT | TCCTGTTGCA | ATGGCTGGCG | GTAATATTGT | 5220 |
| TCTGGATATT | ACCAGCAAGG | CCGATAGTTT | GAGTTCTTCT | ACTCAGGCAA | GTGATGTTAT | 5280 |
| TACTAATCAA | AGAAGTATTG | CTACAACGGT | TAATTTGCGT | GATGGACAGA | CTCTTTTACT | 5340 |
| CGGTGGCCTC | ACTGATTATA | AAAACACTTC | TCAAGATTCT | GGCGTACCGT | TCCTGTCTAA | 5400 |
| AATCCCTTTA | ATCGGCCTCC | TGTTTAGCTC | CCGCTCTGAT | TCCAACGAGG | AAAGCACGTT | 5460 |
| ATACGTGCTC | GTCAAAGCAA | CCATAGTACG | CGCCCTGTAG | CGGCGCATTA | AGCGCGGCGG | 5520 |
| GTGTGGTGGT | TACGCGCAGC | GTGACCGCTA | CACTTGCCAG | CGCCCTAGCG | CCCGCTCCTT | 5580 |
| TCGCTTTCTT | CCCTTCCTTT | CTCGCCACGT | TCGCCGGCTT | TCCCCGTCAA | GCTCTAAATC | 5640 |
| GGGGGCTCCC | TTTAGGGTTC | CGATTTAGTG | CTTTACGGCA | CCTCGACCCC | AAAAAACTTG | 5700 |
| ATTTGGGTGA | TGGTTCACGT | AGTGGGCCAT | CGCCCTGATA | GACGGTTTTT | CGCCCTTTGA | 5760 |

-continued

| | | | | | |
|---|---|---|---|---|---|
| CGTTGGAGTC | CACGTTCTTT | AATAGTGGAC | TCTTGTTCCA | AACTGGAACA | ACACTCAACC | 5820
| CTATCTCGGG | CTATTCTTTT | GATTTATAAG | GGATTTTGCC | GATTTCGGAA | CCACCATCAA | 5880
| ACAGGATTTT | CGCCTGCTGG | GGCAAACCAG | CGTGGACCGC | TTGCTGCAAC | TCTCTCAGGG | 5940
| CCAGGCGGTG | AAGGGCAATC | AGCTGTTGCC | CGTCTCGCTG | GTGAAAAGAA | AAACCACCCT | 6000
| GGCGCCCAAT | ACGCAAACCG | CCTCTCCCCG | CGCGTTGGCC | GATTCATTAA | TGCAGCTGGC | 6060
| ACGACAGGTT | TCCCGACTGG | AAAGCGGGCA | GTGAGCGCAA | CGCAATTAAT | GTGAGTTAGC | 6120
| TCACTCATTA | GGCACCCCAG | GCTTTACACT | TTATGCTTCC | GGCTCGTATG | TTGTGTGGAA | 6180
| TTGTGAGCGG | ATAACAATTT | CACACGCGTC | ACTTGGCACT | GGCCGTCGTT | TTACAACGTC | 6240
| GTGACTGGGA | AAACCCTGGC | GTTACCCAAG | CTTTGTACAT | GGAGAAAATA | AAGTGAAACA | 6300
| AAGCACTATT | GCACTGGCAC | TCTTACCGTT | ACCGTTACTG | TTTACCCCTG | TGACAAAAGC | 6360
| CGCCCAGGTC | CAGCTGCTCG | AGTCAGGCCT | ATTGTGCCCA | GGGGATTGTA | CTAGTGGATC | 6420
| CTAGGCTGAA | GGCGATGACC | CTGCTAAGGC | TGCATTCAAT | AGTTTACAGG | CAAGTGCTAC | 6480
| TGAGTACATT | GGCTACGCTT | GGGCTATGGT | AGTAGTTATA | GTTGGTGCTA | CCATAGGGAT | 6540
| TAAATTATTC | AAAAAGTTTA | CGAGCAAGGC | TTCTTAAGCA | ATAGCGAAGA | GGCCCGCACC | 6600
| GATCGCCCTT | CCCAACAGTT | GCGCAGCCTG | AATGGCGAAT | GGCGCTTTGC | CTGGTTTCCG | 6660
| GCACCAGAAG | CGGTGCCGGA | AAGCTGGCTG | GAGTGCGATC | TTCCTGAGGC | CGATACGGTC | 6720
| GTCGTCCCCT | CAAACTGGCA | GATGCACGGT | TACGATGCGC | CCATCTACAC | CAACGTAACC | 6780
| TATCCCATTA | CGGTCAATCC | GCCGTTTGTT | CCCACGGAGA | ATCCGACGGG | TTGTTACTCG | 6840
| CTCACATTTA | ATGTTGATGA | AAGCTGGCTA | CAGGAAGGCC | AGACGCGAAT | TATTTTTGAT | 6900
| GGCGTTCCTA | TTGGTTAAAA | AATGAGCTGA | TTTAACAAAA | ATTTAACGCG | AATTTTAACA | 6960
| AAATATTAAC | GTTTACAATT | TAAATATTTG | CTTATACAAT | CTTCCTGTTT | TGGGGCTTT | 7020
| TCTGATTATC | AACCGGGGTA | CATATGATTG | ACATGCTAGT | TTTACGATTA | CCGTTCATCG | 7080
| ATTCTCTTGT | TTGCTCCAGA | CTCTCAGGCA | ATGACCTGAT | AGCCTTTGTA | GATCTCTCAA | 7140
| AAATAGCTAC | CCTCTCCGGC | ATTAATTTAT | CAGCTAGAAC | GGTTGAATAT | CATATTGATG | 7200
| GTGATTTGAC | TGTCTCCGGC | CTTTCTCACC | CTTTTGAATC | TTTACCTACA | CATTACTCAG | 7260
| GCATTGCATT | TAAAATATAT | GAGGGTTCTA | AAAATTTTTA | TCCTTGCGTT | GAAATAAAGG | 7320
| CTTCTCCCGC | AAAAGTATTA | CAGGGTCATA | ATGTTTTTGG | TACAACCGAT | TTAGCTTTAT | 7380
| GCTCTGAGGC | TTTATTGCTT | AATTTTGCTA | ATTCTTTGCC | TTGCCTGTAT | GATTATTGG | 7440
| ACGTT | | | | | | 7445

( 2 ) INFORMATION FOR SEQ ID NO:2:

( i ) SEQUENCE CHARACTERISTICS:
        ( A ) LENGTH: 7317 base pairs
        ( B ) TYPE: nucleic acid
        ( C ) STRANDEDNESS: both
        ( D ) TOPOLOGY: circular ( x i ) SEQUENCE DESCRIPTION: SEQ ID NO:2:

| | | | | | |
|---|---|---|---|---|---|
| AATGCTACTA | CTATTAGTAG | AATTGATGCC | ACCTTTTCAG | CTCGCGCCCC | AAATGAAAAT | 60
| ATAGCTAAAC | AGGTTATTGA | CCATTTGCGA | AATGTATCTA | ATGGTCAAAC | TAAATCTACT | 120
| CGTTCGCAGA | ATTGGGAATC | AACTGTTACA | TGGAATGAAA | CTTCCAGACA | CCGTACTTTA | 180
| GTTGCATATT | TAAAACATGT | TGAGCTACAG | CACCAGATTC | AGCAATTAAG | CTCTAAGCCA | 240
| TCCGCAAAAA | TGACCTCTTA | TCAAAGGAG | CAATTAAAGG | TACTCTCTAA | TCCTGACCTG | 300
| TTGGAGTTTG | CTTCCGGTCT | GGTTCGCTTT | GAAGCTCGAA | TTAAAACGCG | ATATTTGAAG | 360

-continued

| | | | | | |
|---|---|---|---|---|---|
| TCTTTCGGGC | TTCCTCTTAA | TCTTTTTGAT | GCAATCCGCT | TTGCTTCTGA | CTATAATAGT | 420 |
| CAGGGTAAAG | ACCTGATTTT | TGATTTATGG | TCATTCTCGT | TTTCTGAACT | GTTTAAAGCA | 480 |
| TTTGAGGGGG | ATTCAATGAA | TATTTATGAC | GATTCCGCAG | TATTGGACGC | TATCCAGTCT | 540 |
| AAACATTTTA | CTATTACCCC | CTCTGGCAAA | ACTTCTTTTG | CAAAAGCCTC | TCGCTATTTT | 600 |
| GGTTTTTATC | GTCGTCTGGT | AAACGAGGGT | TATGATAGTG | TTGCTCTTAC | TATGCCTCGT | 660 |
| AATTCCTTTT | GGCGTTATGT | ATCTGCATTA | GTTGAATGTG | GTATTCCTAA | ATCTCAACTG | 720 |
| ATGAATCTTT | CTACCTGTAA | TAATGTTGTT | CCGTTAGTTC | GTTTATTAA | CGTAGATTT | 780 |
| TCTTCCCAAC | GTCCTGACTG | GTATAATGAG | CCAGTTCTTA | AAATCGCATA | AGGTAATTCA | 840 |
| CAATGATTAA | AGTTGAAATT | AAACCATCTC | AAGCCCAATT | TACTACTCGT | TCTGGTGTTT | 900 |
| CTCGTCAGGG | CAAGCCTTAT | TCACTGAATG | AGCAGCTTTG | TTACGTTGAT | TTGGGTAATG | 960 |
| AATATCCGGT | TCTTGTCAAG | ATTACTCTTG | ATGAAGGTCA | GCCAGCCTAT | GCGCCTGGTC | 1020 |
| TGTACACCGT | TCATCTGTCC | TCTTTCAAAG | TTGGTCAGTT | CGGTTCCCTT | ATGATTGACC | 1080 |
| GTCTGCGCCT | CGTTCCGGCT | AAGTAACATG | GAGCAGGTCG | CGGATTTCGA | CACAATTTAT | 1140 |
| CAGGCGATGA | TACAAATCTC | CGTTGTACTT | TGTTTCGCGC | TTGGTATAAT | CGCTGGGGGT | 1200 |
| CAAAGATGAG | TGTTTTAGTG | TATTCTTTCG | CCTCTTTCGT | TTTAGGTTGG | TGCCTTCGTA | 1260 |
| GTGGCATTAC | GTATTTTACC | CGTTTAATGG | AAACTTCCTC | ATGAAAAGT | CTTTAGTCCT | 1320 |
| CAAAGCCTCT | GTAGCCGTTG | CTACCCTCGT | TCCGATGCTG | TCTTTCGCTG | CTGAGGGTGA | 1380 |
| CGATCCCGCA | AAAGCGGCCT | TTAACTCCCT | GCAAGCCTCA | GCGACCGAAT | ATATCGGTTA | 1440 |
| TGCGTGGGCG | ATGGTTGTTG | TCATTGTCGG | CGCAACTATC | GGTATCAAGC | TGTTTAAGAA | 1500 |
| ATTCACCTCG | AAAGCAAGCT | GATAAACCGA | TACAATTAAA | GGCTCCTTTT | GGAGCCTTTT | 1560 |
| TTTTGGAGA | TTTTCAACGT | GAAAAAATTA | TTATTCGCAA | TTCCTTTAGT | TGTTCCTTTC | 1620 |
| TATTCTCACT | CCGCTGAAAC | TGTTGAAAGT | TGTTTAGCAA | AACCCCATAC | AGAAAATTCA | 1680 |
| TTTACTAACG | TCTGGAAAGA | CGACAAAACT | TTAGATCGTT | ACGCTAACTA | TGAGGGTTGT | 1740 |
| CTGTGGAATG | CTACAGGCGT | TGTAGTTTGT | ACTGGTGACG | AAACTCAGTG | TTACGGTACA | 1800 |
| TGGGTTCCTA | TTGGGCTTGC | TATCCCTGAA | AATGAGGGTG | GTGGCTCTGA | GGGTGGCGGT | 1860 |
| TCTGAGGGTG | GCGGTTCTGA | GGGTGGCGGT | ACTAAACCTC | CTGAGTACGG | TGATACACCT | 1920 |
| ATTCCGGGCT | ATACTTATAT | CAACCCTCTC | GACGGCACTT | ATCCGCCTGG | TACTGAGCAA | 1980 |
| AACCCCGCTA | ATCCTAATCC | TTCTCTTGAG | GAGTCTCAGC | CTCTTAATAC | TTTCATGTTT | 2040 |
| CAGAATAATA | GGTTCCGAAA | TAGGCAGGGG | GCATTAACTG | TTTATACGGG | CACTGTTACT | 2100 |
| CAAGGCACTG | ACCCCGTTAA | AACTTATTAC | CAGTACACTC | CTGTATCATC | AAAAGCCATG | 2160 |
| TATGACGCTT | ACTGGAACGG | TAAATTCAGA | GACTGCGCTT | TCCATTCTGG | CTTTAATGAA | 2220 |
| GATCCATTCG | TTTGTGAATA | TCAAGGCCAA | TCGTCTGACC | TGCCTCAACC | TCCTGTCAAT | 2280 |
| GCTGGCGGCG | GCTCTGGTGG | TGGTTCTGGT | GGCGGCTCTG | AGGGTGGTGG | CTCTGAGGGT | 2340 |
| GGCGGTTCTG | AGGGTGGCGG | CTCTGAGGGA | GGCGGTTCCG | GTGGTGGCTC | TGGTTCCGGT | 2400 |
| GATTTTGATT | ATGAAAAGAT | GGCAAACGCT | AATAAGGGGG | CTATGACCGA | AAATGCCGAT | 2460 |
| GAAAACGCGC | TACAGTCTGA | CGCTAAAGGC | AAACTTGATT | CTGTCGCTAC | TGATTACGGT | 2520 |
| GCTGCTATCG | ATGGTTTCAT | TGGTGACGTT | TCCGGCCTTG | CTAATGGTAA | TGGTGCTACT | 2580 |
| GGTGATTTTG | CTGGCTCTAA | TTCCCAAATG | GCTCAAGTCG | GTGACGGTGA | TAATTCACCT | 2640 |
| TTAATGAATA | ATTTCCGTCA | ATATTTACCT | TCCCTCCCTC | AATCGGTTGA | ATGTCGCCCT | 2700 |
| TTTGTCTTTA | GCGCTGGTAA | ACCATATGAA | TTTTCTATTG | ATTGTGACAA | AATAAACTTA | 2760 |

```
TTCCGTGGTG TCTTTGCGTT TCTTTTATAT GTTGCCACCT TTATGTATGT ATTTTCTACG    2820
TTTGCTAACA TACTGCGTAA TAAGGAGTCT TAATCATGCC AGTTCTTTTG GGTATTCCGT    2880
TATTATTGCG TTTCCTCGGT TTCCTTCTGG TAACTTTGTT CGGCTATCTG CTTACTTTTC    2940
TTAAAAAGGG CTTCGGTAAG ATAGCTATTG CTATTTCATT GTTTCTTGCT CTTATTATTG    3000
GGCTTAACTC AATTCTTGTG GGTTATCTCT CTGATATTAG CGCTCAATTA CCCTCTGACT    3060
TTGTTCAGGG TGTTCAGTTA ATTCTCCCGT CTAATGCGCT TCCCTGTTTT TATGTTATTC    3120
TCTCTGTAAA GGCTGCTATT TTCATTTTTG ACGTTAAACA AAAAATCGTT TCTTATTTGG    3180
ATTGGGATAA ATAATATGGC TGTTTATTTT GTAACTGGCA AATTAGGCTC TGGAAAGACG    3240
CTCGTTAGCG TTGGTAAGAT TCAGGATAAA ATTGTAGCTG GGTGCAAAAT AGCAACTAAT    3300
CTTGATTTAA GGCTTCAAAA CCTCCCGCAA GTCGGGAGGT TCGCTAAAAC GCCTCGCGTT    3360
CTTAGAATAC CGGATAAGCC TTCTATATCT GATTTGCTTG CTATTGGGCG CGGTAATGAT    3420
TCCTACGATG AAAATAAAAA CGGCTTGCTT GTTCTCGATG AGTGCGGTAC TTGGTTTAAT    3480
ACCCGTTCTT GGAATGATAA GGAAAGACAG CCGATTATTG ATTGGTTTCT ACATGCTCGT    3540
AAATTAGGAT GGGATATTAT TTTTCTTGTT CAGGACTTAT CTATTGTTGA TAAACAGGCG    3600
CGTTCTGCAT TAGCTGAACA TGTTGTTTAT TGTCGTCGTC TGGACAGAAT TACTTTACCT    3660
TTTGTCGGTA CTTTATATTC TCTTATTACT GGCTCGAAAA TGCCTCTGCC TAAATTACAT    3720
GTTGGCGTTG TTAAATATGG CGATTCTCAA TTAAGCCCTA CTGTTGAGCG TTGGCTTTAT    3780
ACTGGTAAGA ATTTGTATAA CGCATATGAT ACTAAACAGG CTTTTTCTAG TAATTATGAT    3840
TCCGGTGTTT ATTCTTATTT AACGCCTTAT TTATCACACG GTCGGTATTT CAAACCATTA    3900
AATTTAGGTC AGAAGATGAA GCTTACTAAA ATATATTTGA AAAGTTTTC ACGCGTTCTT    3960
TGTCTTGCGA TTGGATTTGC ATCAGCATTT ACATATAGTT ATATAACCCA ACCTAAGCCG    4020
GAGGTTAAAA AGGTAGTCTC TCAGACCTAT GATTTTGATA AATTCACTAT TGACTCTTCT    4080
CAGCGTCTTA ATCTAAGCTA TCGCTATGTT TTCAAGGATT CTAAGGGAAA ATTAATTAAT    4140
AGCGACGATT TACAGAAGCA AGGTTATTCA CTCACATATA TTGATTTATG TACTGTTTCC    4200
ATTAAAAAAG GTAATTCAAA TGAAATTGTT AAATGTAATT AATTTTGTTT TCTTGATGTT    4260
TGTTTCATCA TCTTCTTTTG CTCAGGTAAT TGAAATGAAT AATTCGCCTC TGCGCGATTT    4320
TGTAACTTGG TATTCAAAGC AATCAGGCGA ATCCGTTATT GTTTCTCCCG ATGTAAAAGG    4380
TACTGTTACT GTATATTCAT CTGACGTTAA ACCTGAAAAT CTACGCAATT TCTTTATTTC    4440
TGTTTTACGT GCTAATAATT TTGATATGGT TGGTTCAATT CCTTCCATAA TTCAGAAGTA    4500
TAATCCAAAC AATCAGGATT ATATTGATGA ATTGCCATCA TCTGATAATC AGGAATATGA    4560
TGATAATTCC GCTCCTTCTG GTGGTTTCTT TGTTCCGCAA AATGATAATG TTACTCAAAC    4620
TTTTAAAATT AATAACGTTC GGGCAAAGGA TTTAATACGA GTTGTCGAAT TGTTTGTAAA    4680
GTCTAATACT TCTAAATCCT CAAATGTATT ATCTATTGAC GGCTCTAATC TATTAGTTGT    4740
TAGTGCACCT AAAGATATTT TAGATAACCT TCCTCAATTC CTTTCTACTG TTGATTTGCC    4800
AACTGACCAG ATATTGATTG AGGGTTTGAT ATTTGAGGTT CAGCAAGGTG ATGCTTTAGA    4860
TTTTTCATTT GCTGCTGGCT CTCAGCGTGG CACTGTTGCA GGCGGTGTTA ATACTGACCG    4920
CCTCACCTCT GTTTTATCTT CTGCTGGTGG TTCGTTCGGT ATTTTTAATG GCGATGTTTT    4980
AGGGCTATCA GTTCGCGCAT TAAAGACTAA TAGCCATTCA AAAATATTGT CTGTGCCACG    5040
TATTCTTACG CTTTCAGGTC AGAAGGGTTC TATCTCTGTT GGCCAGAATG TCCCTTTTAT    5100
TACTGGTCGT GTGACTGGTG AATCTGCCAA TGTAAATAAT CCATTTCAGA CGATTGAGCG    5160
```

```
TCAAAATGTA GGTATTTCCA TGAGCGTTTT TCCTGTTGCA ATGGCTGGCG GTAATATTGT    5220

TCTGGATATT ACCAGCAAGG CCGATAGTTT GAGTTCTTCT ACTCAGGCAA GTGATGTTAT    5280

TACTAATCAA AGAAGTATTG CTACAACGGT TAATTGCGT  GATGGACAGA CTCTTTTACT    5340

CGGTGGCCTC ACTGATTATA AAACACTTC  TCAAGATTCT GGCGTACCGT TCCTGTCTAA    5400

AATCCCTTTA ATCGGCCTCC TGTTTAGCTC CCGCTCTGAT TCCAACGAGG AAAGCACGTT    5460

ATACGTGCTC GTCAAAGCAA CCATAGTACG CGCCCTGTAG CGGCGCATTA AGCGCGGCGG    5520

GTGTGGTGGT TACGCGCAGC GTGACCGCTA CACTTGCCAG CGCCCTAGCG CCCGCTCCTT    5580

TCGCTTTCTT CCCTTCCTTT CTCGCCACGT TCGCCGGCTT TCCCCGTCAA GCTCTAAATC    5640

GGGGGCTCCC TTTAGGGTTC CGATTTAGTG CTTTACGGCA CCTCGACCCC AAAAAACTTG    5700

ATTTGGGTGA TGGTTCACGT AGTGGGCCAT CGCCCTGATA GACGGTTTTT CGCCCTTTGA    5760

CGTTGGAGTC CACGTTCTTT AATAGTGGAC TCTTGTTCCA AACTGGAACA ACACTCAACC    5820

CTATCTCGGG CTATTCTTTT GATTTATAAG GGATTTTGCC GATTTCGGAA CCACCATCAA    5880

ACAGGATTTT CGCCTGCTGG GGCAAACCAG CGTGGACCGC TTGCTGCAAC TCTCTCAGGG    5940

CCAGGCGGTG AAGGGCAATC AGCTGTTGCC CGTCTCGCTG GTGAAAAGAA AAACCACCCT    6000

GGCGCCCAAT ACGCAAACCG CCTCTCCCCG CGCGTTGGCC GATTCATTAA TGCAGCTGGC    6060

ACGACAGGTT TCCCGACTGG AAAGCGGGCA GTGAGCGCAA CGCAATTAAT GTGAGTTAGC    6120

TCACTCATTA GGCACCCCAG GCTTTACACT TTATGCTTCC GGCTCGTATG TTGTGTGGAA    6180

TTGTGAGCGG ATAACAATTT CACACGCCAA GGAGACAGTC ATAATGAAAT ACCTATTGCC    6240

TACGGCAGCC GCTGGATTGT TATTACTCGC TGCCCAACCA GCCATGGCCG AGCTCGTGAT    6300

GACCCAGACT CCAGATATCC AACAGGAATG AGTGTTAATT CTAGAACGCG TCACTTGGCA    6360

CTGGCCGTCG TTTTACAACG TCGTGACTGG GAAAACCCTG GCGTTACCCA AGCTTAATCG    6420

CCTTGCAGAA TTCCCTTTCG CCAGCTGGCG TAATAGCGAA GAGGCCCGCA CCGATCGCCC    6480

TTCCCAACAG TTGCGCAGCC TGAATGGCGA ATGGCGCTTT GCCTGGTTTC CGGCACCAGA    6540

AGCGGTGCCG GAAAGCTGGC TGGAGTGCGA TCTTCCTGAG GCCGATACGG TCGTCGTCCC    6600

CTCAAACTGG CAGATGCACG GTTACGATGC GCCCATCTAC ACCAACGTAA CCTATCCCAT    6660

TACGGTCAAT CCGCCGTTTG TTCCCACGGA GAATCCGACG GGTTGTTACT CGCTCACATT    6720

TAATGTTGAT GAAAGCTGGC TACAGGAAGG CCAGACGCGA ATTATTTTTG ATGGCGTTCC    6780

TATTGGTTAA AAAATGAGCT GATTAACAA  AAATTTAACG CGAATTTTAA CAAAATATTA    6840

ACGTTTACAA TTTAAATATT TGCTTATACA ATCTTCCTGT TTTTGGGGCT TTTCTGATTA    6900

TCAACCGGGG TACATATGAT TGACATGCTA GTTTTACGAT TACCGTTCAT CGATTCTCTT    6960

GTTTGCTCCA GACTCTCAGG CAATGACCTG ATAGCCTTTG TAGATCTCTC AAAAATAGCT    7020

ACCCTCTCCG GCATTAATTT ATCAGCTAGA ACGGTTGAAT ATCATATTGA TGGTGATTTG    7080

ACTGTCTCCG GCCTTTCTCA CCCTTTTGAA TCTTTACCTA CACATTACTC AGGCATTGCA    7140

TTTAAAATAT ATGAGGGTTC TAAAAATTTT TATCCTTGCG TTGAAATAAA GGCTTCTCCC    7200

GCAAAAGTAT TACAGGGTCA TAATGTTTTT GGTACAACCG ATTTAGCTTT ATGCTCTGAG    7260

GCTTTATTGC TTAATTTTGC TAATTCTTTG CCTTGCCTGT ATGATTTATT GGATGTT      7317
```

( 2 ) INFORMATION FOR SEQ ID NO:3:

( i ) SEQUENCE CHARACTERISTICS:
        ( A ) LENGTH: 7729 base pairs
        ( B ) TYPE: nucleic acid
        ( C ) STRANDEDNESS: both ( D ) TOPOLOGY: circular ( x i ) SEQUENCE DESCRIPTION: SEQ ID NO:3:

| | | | | | |
|---|---|---|---|---|---|
| AATGCTACTA | CTATTAGTAG | AATTGATGCC | ACCTTTTCAG | CTCGCGCCCC | AAATGAAAAT | 60
| ATAGCTAAAC | AGGTTATTGA | CCATTTGCGA | AATGTATCTA | ATGGTCAAAC | TAAATCTACT | 120
| CGTTCGCAGA | ATTGGGAATC | AACTGTTACA | TGGAATGAAA | CTTCCAGACA | CCGTACTTTA | 180
| GTTGCATATT | TAAAACATGT | TGAGCTACAG | CACCAGATTC | AGCAATTAAG | CTCTAAGCCA | 240
| TCTGCAAAAA | TGACCTCTTA | TCAAAGGAG | CAATTAAAGG | TACTCTCTAA | TCCTGACCTG | 300
| TTGGAGTTTG | CTTCCGGTCT | GGTTCGCTTT | GAAGCTCGAA | TTAAACGCG | ATATTTGAAG | 360
| TCTTTCGGGC | TTCCTCTTAA | TCTTTTTGAT | GCAATCCGCT | TTGCTTCTGA | CTATAATAGT | 420
| CAGGGTAAAG | ACCTGATTTT | TGATTTATGG | TCATTCTCGT | TTTCTGAACT | GTTTAAAGCA | 480
| TTTGAGGGGG | ATTCAATGAA | TATTTATGAC | GATTCCGCAG | TATTGGACGC | TATCCAGTCT | 540
| AAACATTTTA | CTATTACCCC | CTCTGGCAAA | ACTTCTTTTG | CAAAAGCCTC | TCGCTATTTT | 600
| GGTTTTTATC | GTCGTCTGGT | AAACGAGGGT | TATGATAGTG | TTGCTCTTAC | TATGCCTCGT | 660
| AATTCCTTTT | GGCGTTATGT | ATCTGCATTA | GTTGAATGTG | GTATTCCTAA | ATCTCAACTG | 720
| ATGAATCTTT | CTACCTGTAA | TAATGTTGTT | CCGTTAGTTC | GTTTTATTAA | CGTAGATTTT | 780
| TCTTCCCAAC | GTCCTGACTG | GTATAATGAG | CCAGTTCTTA | AAATCGCATA | AGGTAATTCA | 840
| CAATGATTAA | AGTTGAAATT | AAACCATCTC | AAGCCCAATT | TACTACTCGT | TCTGGTGTTT | 900
| CTCGTCAGGG | CAAGCCTTAT | TCACTGAATG | AGCAGCTTTG | TTACGTTGAT | TTGGGTAATG | 960
| AATATCCGGT | TCTTGTCAAG | ATTACTCTTG | ATGAAGGTCA | GCCAGCCTAT | GCGCCTGGTC | 1020
| TGTACACCGT | TCATCTGTCC | TCTTTCAAAG | TTGGTCAGTT | CGGTTCCCTT | ATGATTGACC | 1080
| GTCTGCGCCT | CGTTCCGGCT | AAGTAACATG | GAGCAGGTCG | CGGATTTCGA | CACAATTTAT | 1140
| CAGGCGATGA | TACAAATCTC | CGTTGTACTT | TGTTTCGCGC | TTGGTATAAT | CGCTGGGGGT | 1200
| CAAAGATGAG | TGTTTTAGTG | TATTCTTTCG | CCTCTTTCGT | TTTAGGTTGG | TGCCTTCGTA | 1260
| GTGGCATTAC | GTATTTTACC | CGTTTAATGG | AAACTTCCTC | ATGAAAAGT | CTTTAGTCCT | 1320
| CAAAGCCTCT | GTAGCCGTTG | CTACCCTCGT | TCCGATGCTG | TCTTTCGCTG | CTGAGGGTGA | 1380
| CGATCCCGCA | AAAGCGGCCT | TTAACTCCCT | GCAAGCCTCA | GCGACCGAAT | ATATCGGTTA | 1440
| TGCGTGGGCG | ATGGTTGTTG | TCATTGTCGG | CGCAACTATC | GGTATCAAGC | TGTTTAAGAA | 1500
| ATTCACCTCG | AAAGCAAGCT | GATAAACCGA | TACAATTAAA | GGCTCCTTTT | GGAGCCTTTT | 1560
| TTTTTGGAGA | TTTTCAACGT | GAAAAAATTA | TTATTCGCAA | TTCCTTTAGT | TGTTCCTTTC | 1620
| TATTCTCACT | CCGCTGAAAC | TGTTGAAAGT | TGTTTAGCAA | AACCCCATAC | AGAAAATTCA | 1680
| TTTACTAACG | TCTGGAAAGA | CGACAAAACT | TTAGATCGTT | ACGCTAACTA | TGAGGGTTGT | 1740
| CTGTGGAATG | CTACAGGCGT | TGTAGTTTGT | ACTGGTGACG | AAACTCAGTG | TTACGGTACA | 1800
| TGGGTTCCTA | TTGGGCTTGC | TATCCCTGAA | AATGAGGGTG | GTGGCTCTGA | GGGTGGCGGT | 1860
| TCTGAGGGTG | GCGGTTCTGA | GGGTGGCGGT | ACTAAACCTC | CTGAGTACGG | TGATACACCT | 1920
| ATTCCGGGCT | ATACTTATAT | CAACCCTCTC | GACGGCACTT | ATCCGCCTGG | TACTGAGCAA | 1980
| AACCCCGCTA | ATCCTAATCC | TTCTCTTGAG | GAGTCTCAGC | CTCTTAATAC | TTTCATGTTT | 2040
| CAGAATAATA | GGTTCCGAAA | TAGGCAGGGG | GCATTAACTG | TTTATACGGG | CACTGTTACT | 2100
| CAAGGCACTG | ACCCCGTTAA | AACTTATTAC | CAGTACACTC | CTGTATCATC | AAAAGCCATG | 2160
| TATGACGCTT | ACTGGAACGG | TAAATTCAGA | GACTGCGCTT | TCCATTCTGG | CTTTAATGAA | 2220
| GATCCATTCG | TTTGTGAATA | TCAAGGCCAA | TCGTCTGACC | TGCCTCAACC | TCCTGTCAAT | 2280

| | | | | | | |
|---|---|---|---|---|---|---|
| GCTGGCGGCG | GCTCTGGTGG | TGGTTCTGGT | GGCGGCTCTG | AGGGTGGTGG | CTCTGAGGGT | 2340 |
| GGCGGTTCTG | AGGGTGGCGG | CTCTGAGGGA | GGCGGTTCCG | GTGGTGGCTC | TGGTTCCGGT | 2400 |
| GATTTTGATT | ATGAAAAGAT | GGCAAACGCT | AATAAGGGGG | CTATGACCGA | AAATGCCGAT | 2460 |
| GAAAACGCGC | TACAGTCTGA | CGCTAAAGGC | AAACTTGATT | CTGTCGCTAC | TGATTACGGT | 2520 |
| GCTGCTATCG | ATGGTTTCAT | TGGTGACGTT | TCCGGCCTTG | CTAATGGTAA | TGGTGCTACT | 2580 |
| GGTGATTTTG | CTGGCTCTAA | TTCCCAAATG | GCTCAAGTCG | GTGACGGTGA | TAATTCACCT | 2640 |
| TTAATGAATA | ATTTCCGTCA | ATATTTACCT | TCCCTCCCTC | AATCGGTTGA | ATGTCGCCCT | 2700 |
| TTTGTCTTTA | GCGCTGGTAA | ACCATATGAA | TTTTCTATTG | ATTGTGACAA | AATAAACTTA | 2760 |
| TTCCGTGGTG | TCTTTGCGTT | TCTTTTATAT | GTTGCCACCT | TTATGTATGT | ATTTTCTACG | 2820 |
| TTTGCTAACA | TACTGCGTAA | TAAGGAGTCT | TAATCATGCC | AGTTCTTTTG | GGTATTCCGT | 2880 |
| TATTATTGCG | TTTCCTCGGT | TTCCTTCTGG | TAACTTTGTT | CGGCTATCTG | CTTACTTTTC | 2940 |
| TTAAAAAGGG | CTTCGGTAAG | ATAGCTATTG | CTATTTCATT | GTTTCTTGCT | CTTATTATTG | 3000 |
| GGCTTAACTC | AATTCTTGTG | GGTTATCTCT | CTGATATTAG | CGCTCAATTA | CCCTCTGACT | 3060 |
| TTGTTCAGGG | TGTTCAGTTA | ATTCTCCCGT | CTAATGCGCT | TCCCTGTTTT | TATGTTATTC | 3120 |
| TCTCTGTAAA | GGCTGCTATT | TTCATTTTTG | ACGTTAAACA | AAAAATCGTT | TCTTATTTGG | 3180 |
| ATTGGGATAA | ATAATATGGC | TGTTTATTTT | GTAACTGGCA | AATTAGGCTC | TGGAAAGACG | 3240 |
| CTCGTTAGCG | TTGGTAAGAT | TCAGGATAAA | ATTGTAGCTG | GGTGCAAAAT | AGCAACTAAT | 3300 |
| CTTGATTTAA | GGCTTCAAAA | CCTCCCGCAA | GTCGGGAGGT | TCGCTAAAAC | GCCTCGCGTT | 3360 |
| CTTAGAATAC | CGGATAAGCC | TTCTATATCT | GATTTGCTTG | CTATTGGGCG | CGGTAATGAT | 3420 |
| TCCTACGATG | AAAATAAAAA | CGGCTTGCTT | GTTCTCGATG | AGTGCGGTAC | TTGGTTTAAT | 3480 |
| ACCCGTTCTT | GGAATGATAA | GGAAAGACAG | CCGATTATTG | ATTGGTTTCT | ACATGCTCGT | 3540 |
| AAATTAGGAT | GGGATATTAT | TTTTCTTGTT | CAGGACTTAT | CTATTGTTGA | TAAACAGGCG | 3600 |
| CGTTCTGCAT | TAGCTGAACA | TGTTGTTTAT | TGTCGTCGTC | TGGACAGAAT | TACTTTACCT | 3660 |
| TTTGTCGGTA | CTTTATATTC | TCTTATTACT | GGCTCGAAAA | TGCCTCTGCC | TAAATTACAT | 3720 |
| GTTGGCGTTG | TTAAATATGG | CGATTCTCAA | TTAAGCCCTA | CTGTTGAGCG | TTGGCTTTAT | 3780 |
| ACTGGTAAGA | ATTTGTATAA | CGCATATGAT | ACTAAACAGG | CTTTTTCTAG | TAATTATGAT | 3840 |
| TCCGGTGTTT | ATTCTTATTT | AACGCCTTAT | TTATCACACG | GTCGGTATTT | CAAACCATTA | 3900 |
| AATTTAGGTC | AGAAGATGAA | GCTTACTAAA | ATATATTTGA | AAAAGTTTTC | ACGCGTTCTT | 3960 |
| TGTCTTGCGA | TTGGATTTGC | ATCAGCATTT | ACATATAGTT | ATATAACCCA | ACCTAAGCCG | 4020 |
| GAGGTTAAAA | AGGTAGTCTC | TCAGACCTAT | GATTTTGATA | AATTCACTAT | TGACTCTTCT | 4080 |
| CAGCGTCTTA | ATCTAAGCTA | TCGCTATGTT | TTCAAGGATT | CTAAGGGAAA | ATTAATTAAT | 4140 |
| AGCGACGATT | TACAGAAGCA | AGGTTATTCA | CTCACATATA | TTGATTTATG | TACTGTTTCC | 4200 |
| ATTAAAAAAG | GTAATTCAAA | TGAAATTGTT | AAATGTAATT | AATTTTGTTT | TCTTGATGTT | 4260 |
| TGTTTCATCA | TCTTCTTTTG | CTCAGGTAAT | TGAAATGAAT | AATTCGCCTC | TGCGCGATTT | 4320 |
| TGTAACTTGG | TATTCAAAGC | AATCAGGCGA | ATCCGTTATT | GTTTCTCCCG | ATGTAAAAGG | 4380 |
| TACTGTTACT | GTATATTCAT | CTGACGTTAA | ACCTGAAAAT | CTACGCAATT | TCTTTATTTC | 4440 |
| TGTTTTACGT | GCTAATAATT | TTGATATGGT | TGGTTCAATT | CCTTCCATAA | TTCAGAAGTA | 4500 |
| TAATCCAAAC | AATCAGGATT | ATATTGATGA | ATTGCCATCA | TCTGATAATC | AGGAATATGA | 4560 |
| TGATAATTCC | GCTCCTTCTG | GTGGTTTCTT | TGTTCCGCAA | AATGATAATG | TTACTCAAAC | 4620 |
| TTTTAAAATT | AATAACGTTC | GGGCAAAGGA | TTTAATACGA | GTTGTCGAAT | TGTTTGTAAA | 4680 |

| | | | | | | |
|---|---|---|---|---|---|---|
| GTCTAATACT | TCTAAATCCT | CAAATGTATT | ATCTATTGAC | GGCTCTAATC | TATTAGTTGT | 4740 |
| TAGTGCACCT | AAAGATATTT | TAGATAACCT | TCCTCAATTC | CTTTCTACTG | TTGATTTGCC | 4800 |
| AACTGACCAG | ATATTGATTG | AGGGTTTGAT | ATTTGAGGTT | CAGCAAGGTG | ATGCTTTAGA | 4860 |
| TTTTTCATTT | GCTGCTGGCT | CTCAGCGTGG | CACTGTTGCA | GGCGGTGTTA | ATACTGACCG | 4920 |
| CCTCACCTCT | GTTTATCTT | CTGCTGGTGG | TTCGTTCGGT | ATTTTAATG | GCGATGTTTT | 4980 |
| AGGGCTATCA | GTTCGCGCAT | TAAAGACTAA | TAGCCATTCA | AAAATATTGT | CTGTGCCACG | 5040 |
| TATTCTTACG | CTTTCAGGTC | AGAAGGGTTC | TATCTCTGTT | GGCCAGAATG | TCCCTTTTAT | 5100 |
| TACTGGTCGT | GTGACTGGTG | AATCTGCCAA | TGTAAATAAT | CCATTTCAGA | CGATTGAGCG | 5160 |
| TCAAAATGTA | GGTATTTCCA | TGAGCGTTTT | TCCTGTTGCA | ATGGCTGGCG | GTAATATTGT | 5220 |
| TCTGGATATT | ACCAGCAAGG | CCGATAGTTT | GAGTTCTTCT | ACTCAGGCAA | GTGATGTTAT | 5280 |
| TACTAATCAA | AGAAGTATTG | CTACAACGGT | TAATTTGCGT | GATGGACAGA | CTCTTTTACT | 5340 |
| CGGTGGCCTC | ACTGATTATA | AAAACACTTC | TCAAGATTCT | GGCGTACCGT | TCCTGTCTAA | 5400 |
| AATCCCTTTA | ATCGGCCTCC | TGTTTAGCTC | CCGCTCTGAT | TCCAACGAGG | AAAGCACGTT | 5460 |
| ATACGTGCTC | GTCAAAGCAA | CCATAGTACG | CGCCCTGTAG | CGGCGCATTA | AGCGCGGCGG | 5520 |
| GTGTGGTGGT | TACGCGCAGC | GTGACCGCTA | CACTTGCCAG | CGCCCTAGCG | CCCGCTCCTT | 5580 |
| TCGCTTTCTT | CCCTTCCTTT | CTCGCCACGT | TCGCCGGCTT | TCCCCGTCAA | GCTCTAAATC | 5640 |
| GGGGGCTCCC | TTTAGGGTTC | CGATTTAGTG | CTTTACGGCA | CCTCGACCCC | AAAAAACTTG | 5700 |
| ATTTGGGTGA | TGGTTCACGT | AGTGGGCCAT | CGCCCTGATA | GACGGTTTTT | CGCCCTTTGA | 5760 |
| CGTTGGAGTC | CACGTTCTTT | AATAGTGGAC | TCTTGTTCCA | AACTGGAACA | ACACTCAACC | 5820 |
| CTATCTCGGG | CTATTCTTTT | GATTTATAAG | GGATTTTGCC | GATTTCGGAA | CCACCATCAA | 5880 |
| ACAGGATTTT | CGCCTGCTGG | GGCAAACCAG | CGTGGACCGC | TTGCTGCAAC | TCTCTCAGGG | 5940 |
| CCAGGCGGTG | AAGGGCAATC | AGCTGTTGCC | CGTCTCGCTG | GTGAAAAGAA | AAACCACCCT | 6000 |
| GGCGCCCAAT | ACGCAAACCG | CCTCTCCCCG | CGCGTTGGCC | GATTCATTAA | TGCAGCTGGC | 6060 |
| ACGACAGGTT | TCCCGACTGG | AAAGCGGGCA | GTGAGCGCAA | CGCAATTAAT | GTGAGTTAGC | 6120 |
| TCACTCATTA | GGCACCCCAG | GCTTTACACT | TTATGCTTCC | GGCTCGTATG | TTGTGTGGAA | 6180 |
| TTGTGAGCGG | ATAACAATTT | CACACGCGTC | ACTTGGCACT | GGCCGTCGTT | TTACAACGTC | 6240 |
| GTGACTGGGA | AAACCCTGGC | GTTACCCAAG | CTTTGTACAT | GGAGAAAATA | AAGTGAAACA | 6300 |
| AAGCACTATT | GCACTGGCAC | TCTTACCGTT | ACTGTTTACC | CCTGTGGCAA | AAGCCCAGGT | 6360 |
| CCAGCTGCTC | GAGTCGGTCT | TCCCCCTGGC | ACCCTCCTCC | AAGAGCACCT | CTGGGGGCAC | 6420 |
| AGCGGCCCTG | GCTGCCTGG | TCAAGACTAA | TTCCCCGAAC | CGGTGACGGT | GTCGTGGAAC | 6480 |
| TCAGGCGCCC | TGACCAGCGG | CGTGCACACC | TTCCCGGCTG | TCCTACAGTC | CTCAGGACTC | 6540 |
| TACTCCCTCA | GCAGCGTGGT | GACCGTGCCC | TCCAGCAGCT | TGGGCACCCA | GACCTACATC | 6600 |
| TGCAACGTGA | ATCACAAGCC | CAGCAACACC | AAGGTGGACA | AGAAAGCAGA | GCCCAAATCT | 6660 |
| TGTACTAGTG | GATCCTACCC | GTACGACGTT | CCGGACTACG | CTTCTTAGGC | TGAAGGCGAT | 6720 |
| GACCCTGCTA | AGGCTGCATT | CAATAGTTTA | CAGGCAAGTG | CTACTGAGTA | CATTGGCTAC | 6780 |
| GCTTGGGCTA | TGGTAGTAGT | TATAGTTGGT | GCTACCATAG | GGATTAAATT | ATTCAAAAAG | 6840 |
| TTTACGAGCA | AGGCTTCTTA | AGCAATAGCG | AAGAGGCCCG | CACCGATCGC | CCTTCCCAAC | 6900 |
| AGTTGCGCAG | CCTGAATGGC | GAATGGCGCT | TTGCCTGGTT | TCCGGCACCA | GAAGCGGTGC | 6960 |
| CGGAAAGCTG | GCTGGAGTGC | GATCTTCCTG | AGGCCGATAC | GGTCGTCGTC | CCCTCAAACT | 7020 |
| GGCAGATGCA | CGGTTACGAT | GCGCCCATCT | ACACCAACGT | AACCTATCCC | ATTACGGTCA | 7080 |

-continued

| | | | | | |
|---|---|---|---|---|---|
| ATCCGCCGTT | TGTTCCCACG | GAGAATCCGA | CGGGTTGTTA | CTCGCTCACA | TTTAATGTTG | 7140
| ATGAAAGCTG | GCTACAGGAA | GGCCAGACGC | GAATTATTTT | TGATGGCGTT | CCTATTGGTT | 7200
| AAAAAATGAG | CTGATTTAAC | AAAAATTTAA | CGCGAATTTT | AACAAAATAT | TAACGTTTAC | 7260
| AATTTAAATA | TTTGCTTATA | CAATCTTCCT | GTTTTGGGG | CTTTTCTGAT | TATCAACCGG | 7320
| GGTACATATG | ATTGACATGC | TAGTTTTACG | ATTACCGTTC | ATCGATTCTC | TTGTTTGCTC | 7380
| CAGACTCTCA | GGCAATGACC | TGATAGCCTT | TGTAGATCTC | TCAAAAATAG | CTACCCTCTC | 7440
| CGGCATTAAT | TTATCAGCTA | GAACGGTTGA | ATATCATATT | GATGGTGATT | TGACTGTCTC | 7500
| CGGCCTTTCT | CACCCTTTTG | AATCTTTACC | TACACATTAC | TCAGGCATTG | CATTTAAAAT | 7560
| ATATGAGGGT | TCTAAAAATT | TTTATCCTTG | CGTTGAAATA | AAGGCTTCTC | CCGCAAAAGT | 7620
| ATTACAGGGT | CATAATGTTT | TTGGTACAAC | CGATTAGCT | TTATGCTCTG | AGGCTTTATT | 7680
| GCTTAATTTT | GCTAATTCTT | TGCCTTGCCT | GTATGATTTA | TTGGACGTT | | 7729

(2) INFORMATION FOR SEQ ID NO:4:

(i) SEQUENCE CHARACTERISTICS:
        (A) LENGTH: 7557 base pairs
        (B) TYPE: nucleic acid
        (C) STRANDEDNESS: both
        (D) TOPOLOGY: circular (xi) SEQUENCE DESCRIPTION: SEQ ID NO:4:

| | | | | | |
|---|---|---|---|---|---|
| AATGCTACTA | CTATTAGTAG | AATTGATGCC | ACCTTTTCAG | CTCGCGCCCC | AAATGAAAAT | 60
| ATAGCTAAAC | AGGTTATTGA | CCATTTGCGA | AATGTATCTA | ATGGTCAAAC | TAAATCTACT | 120
| CGTTCGCAGA | ATTGGGAATC | AACTGTTACA | TGGAATGAAA | CTTCCAGACA | CCGTACTTTA | 180
| GTTGCATATT | TAAAACATGT | TGAGCTACAG | CACCAGATTC | AGCAATTAAG | CTCTAAGCCA | 240
| TCCGCAAAAA | TGACCTCTTA | TCAAAGGAG | CAATTAAAGG | TACTCTCTAA | TCCTGACCTG | 300
| TTGGAGTTTG | CTTCCGGTCT | GGTTCGCTTT | GAAGCTCGAA | TTAAAACGCG | ATATTTGAAG | 360
| TCTTTCGGGC | TTCCTCTTAA | TCTTTTTGAT | GCAATCCGCT | TTGCTTCTGA | CTATAATAGT | 420
| CAGGGTAAAG | ACCTGATTTT | TGATTTATGG | TCATTCTCGT | TTTCTGAACT | GTTTAAAGCA | 480
| TTTGAGGGGG | ATTCAATGAA | TATTTATGAC | GATTCCGCAG | TATTGGACGC | TATCCAGTCT | 540
| AAACATTTTA | CTATTACCCC | CTCTGGCAAA | ACTTCTTTTG | CAAAAGCCTC | TCGCTATTTT | 600
| GGTTTTTATC | GTCGTCTGGT | AAACGAGGGT | TATGATAGTG | TTGCTCTTAC | TATGCCTCGT | 660
| AATTCCTTTT | GGCGTTATGT | ATCTGCATTA | GTTGAATGTG | GTATTCCTAA | ATCTCAACTG | 720
| ATGAATCTTT | CTACCTGTAA | TAATGTTGTT | CCGTTAGTTC | GTTTTATTAA | CGTAGATTTT | 780
| TCTTCCCAAC | GTCCTGACTG | GTATAATGAG | CCAGTTCTTA | AAATCGCATA | AGGTAATTCA | 840
| CAATGATTAA | AGTTGAAATT | AAACCATCTC | AAGCCCAATT | TACTACTCGT | TCTGGTGTTT | 900
| CTCGTCAGGG | CAAGCCTTAT | TCACTGAATG | AGCAGCTTTG | TTACGTTGAT | TGGGTAATG | 960
| AATATCCGGT | TCTTGTCAAG | ATTACTCTTG | ATGAAGGTCA | GCCAGCCTAT | GCGCCTGGTC | 1020
| TGTACACCGT | TCATCTGTCC | TCTTTCAAAG | TTGGTCAGTT | CGGTTCCCTT | ATGATTGACC | 1080
| GTCTGCGCCT | CGTTCCGGCT | AAGTAACATG | GAGCAGGTCG | CGGATTTCGA | CACAATTTAT | 1140
| CAGGCGATGA | TACAAATCTC | CGTTGTACTT | TGTTTCGCGC | TTGGTATAAT | CGCTGGGGGT | 1200
| CAAAGATGAG | TGTTTTAGTG | TATTCTTTCG | CCTCTTTCGT | TTTAGGTTGG | TGCCTTCGTA | 1260
| GTGGCATTAC | GTATTTTACC | CGTTTAATGG | AAACTTCCTC | ATGAAAAGT | CTTTAGTCCT | 1320
| CAAAGCCTCT | GTAGCCGTTG | CTACCCTCGT | TCCGATGCTG | TCTTTCGCTG | CTGAGGGTGA | 1380
| CGATCCCGCA | AAAGCGGCCT | TTAACTCCCT | GCAAGCCTCA | GCGACCGAAT | ATATCGGTTA | 1440

```
TGCGTGGGCG ATGGTTGTTG TCATTGTCGG CGCAACTATC GGTATCAAGC TGTTTAAGAA    1500
ATTCACCTCG AAAGCAAGCT GATAAACCGA TACAATTAAA GGCTCCTTTT GGAGCCTTTT    1560
TTTTTGGAGA TTTTCAACGT GAAAAAATTA TTATTCGCAA TTCCTTTAGT TGTTCCTTTC    1620
TATTCTCACT CCGCTGAAAC TGTTGAAAGT TGTTTAGCAA AACCCCATAC AGAAAATTCA    1680
TTTACTAACG TCTGGAAAGA CGACAAAACT TTAGATCGTT ACGCTAACTA TGAGGGTTGT    1740
CTGTGGAATG CTACAGGCGT TGTAGTTTGT ACTGGTGACG AAACTCAGTG TTACGGTACA    1800
TGGGTTCCTA TTGGGCTTGC TATCCCTGAA AATGAGGGTG GTGGCTCTGA GGGTGGCGGT    1860
TCTGAGGGTG GCGGTTCTGA GGGTGGCGGT ACTAAACCTC CTGAGTACGG TGATACACCT    1920
ATTCCGGGCT ATACTTATAT CAACCCTCTC GACGGCACTT ATCCGCCTGG TACTGAGCAA    1980
AACCCCGCTA ATCCTAATCC TTCTCTTGAG GAGTCTCAGC CTCTTAATAC TTTCATGTTT    2040
CAGAATAATA GGTTCCGAAA TAGGCAGGGG GCATTAACTG TTTATACGGG CACTGTTACT    2100
CAAGGCACTG ACCCCGTTAA AACTTATTAC CAGTACACTC CTGTATCATC AAAAGCCATG    2160
TATGACGCTT ACTGGAACGG TAAATTCAGA GACTGCGCTT TCCATTCTGG CTTTAATGAA    2220
GATCCATTCG TTTGTGAATA TCAAGGCCAA TCGTCTGACC TGCCTCAACC TCCTGTCAAT    2280
GCTGGCGGCG GCTCTGGTGG TGGTTCTGGT GGCGGCTCTG AGGGTGGTGG CTCTGAGGGT    2340
GGCGGTTCTG AGGGTGGCGG CTCTGAGGGA GGCGGTTCCG GTGGTGGCTC TGGTTCCGGT    2400
GATTTTGATT ATGAAAAGAT GGCAAACGCT AATAAGGGGG CTATGACCGA AAATGCCGAT    2460
GAAAACGCGC TACAGTCTGA CGCTAAAGGC AAACTTGATT CTGTCGCTAC TGATTACGGT    2520
GCTGCTATCG ATGGTTTCAT TGGTGACGTT TCCGGCCTTG CTAATGGTAA TGGTGCTACT    2580
GGTGATTTTG CTGGCTCTAA TTCCCAAATG GCTCAAGTCG GTGACGGTGA TAATTCACCT    2640
TTAATGAATA ATTTCCGTCA ATATTTACCT TCCCTCCCTC AATCGGTTGA ATGTCGCCCT    2700
TTTGTCTTTA GCGCTGGTAA ACCATATGAA TTTTCTATTG ATTGTGACAA AATAAACTTA    2760
TTCCGTGGTG TCTTTGCGTT TCTTTTATAT GTTGCCACCT TATGTATGT ATTTTCTACG    2820
TTTGCTAACA TACTGCGTAA TAAGGAGTCT TAATCATGCC AGTTCTTTTG GGTATTCCGT    2880
TATTATTGCG TTTCCTCGGT TTCCTTCTGG TAACTTTGTT CGGCTATCTG CTTACTTTTC    2940
TTAAAAAGGG CTTCGGTAAG ATAGCTATTG CCTGTTTCTT GCTCTTATTA TTGGGCTTAA    3000
CTCAATTCTT GTGGGTTATC TCTCTGATAT TAGCGCTCAA TTACCCTCTG ACTTTGTTCA    3060
GGGTGTTCAG TTAATTCTCC CGTCTAATGC GCTTCCCTGT TTTTATGTTA TTCTCTCTGT    3120
AAAGGCTGCT ATTTTCATTT TTGACGTTAA ACAAAAAATC GTTTCTTATT TGGATTGGGA    3180
TAAATAATAT GGCTGTTTAT TTGTAACTG GCAAATTAGG CTCTGGAAAG ACGCTCGTTA    3240
GCGTTGGTAA GATTCAGGAT AAAATTGTAG CTGGGTGCAA AATAGCAACT AATCTTGATT    3300
TAAGGCTTCA AAACCTCCCG CAAGTCGGGA GGTTCGCTAA AACGCCTCGC GTTCTTAGAA    3360
TACCGGATAA GCCTTCTATA TCTGATTTGC TTGCTATTGG GCGCGGTAAT GATTCCTACG    3420
ATGAAAATAA AAACGGCTTG CTTGTTCTCG ATGAGTGCGG TACTTGGTTT AATACCCGTT    3480
CTTGGAATGA TAAGGAAAGA CAGCCGATTA TTGATTGGTT TCTACATGCT CGTAAATTAG    3540
GATGGGATAT TATTTTTCTT GTTCAGGACT TATCTATTGT TGATAAACAG GCGCGTTCTG    3600
CATTAGCTGA ACATGTTGTT TATTGTCGTC GTCTGGACAG AATTACTTTA CCTTTTGTCG    3660
GTACTTTATA TTCTCTTATT ACTGGCTCGA AAATGCCTCT GCCTAAATTA CATGTTGGCG    3720
TTGTTAAATA TGGCGATTCT CAATTAAGCC CTACTGTTGA GCGTTGGCTT TATACTGGTA    3780
AGAATTTGTA TAACGCATAT GATACTAAAC AGGCTTTTTC TAGTAATTAT GATTCCGGTG    3840
```

```
TTTATTCTTA  TTTAACGCCT  TATTTATCAC  ACGGTCGGTA  TTTCAAACCA  TTAAATTTAG   3900
GTCAGAAGAT  GAAGCTTACT  AAAATATATT  TGAAAAAGTT  TTCACGCGTT  CTTTGTCTTG   3960
CGATTGGATT  TGCATCAGCA  TTTACATATA  GTTATATAAC  CCAACCTAAG  CCGGAGGTTA   4020
AAAAGGTAGT  CTCTCAGACC  TATGATTTTG  ATAAATTCAC  TATTGACTCT  TCTCAGCGTC   4080
TTAATCTAAG  CTATCGCTAT  GTTTTCAAGG  ATTCTAAGGG  AAAATTAATT  AATAGCGACG   4140
ATTTACAGAA  GCAAGGTTAT  TCACTCACAT  ATATTGATTT  ATGTACTGTT  TCCATTAAAA   4200
AAGGTAATTC  AAATGAAATT  GTTAAATGTA  ATTAATTTTG  TTTTCTTGAT  GTTTGTTTCA   4260
TCATCTTCTT  TTGCTCAGGT  AATTGAAATG  AATAATTCGC  CTCTGCGCGA  TTTTGTAACT   4320
TGGTATTCAA  AGCAATCAGG  CGAATCCGTT  ATTGTTTCTC  CCGATGTAAA  AGGTACTGTT   4380
ACTGTATATT  CATCTGACGT  TAAACCTGAA  AATCTACGCA  ATTTCTTTAT  TTCTGTTTTA   4440
CGTGCTAATA  ATTTTGATAT  GGTTGGTTCA  ATTCCTTCCA  TAATTCAGAA  GTATAATCCA   4500
AACAATCAGG  ATTATATTGA  TGAATTGCCA  TCATCTGATA  ATCAGGAATA  TGATGATAAT   4560
TCCGCTCCTT  CTGGTGGTTT  CTTTGTTCCG  CAAAATGATA  ATGTTACTCA  AACTTTTAAA   4620
ATTAATAACG  TTCGGGCAAA  GGATTTAATA  CGAGTTGTCG  AATTGTTTGT  AAAGTCTAAT   4680
ACTTCTAAAT  CCTCAAATGT  ATTATCTATT  GACGGCTCTA  ATCTATTAGT  TGTTAGTGCA   4740
CCTAAAGATA  TTTTAGATAA  CCTTCCTCAA  TTCCTTTCTA  CTGTTGATTT  GCCAACTGAC   4800
CAGATATTGA  TTGAGGGTTT  GATATTTGAG  GTTCAGCAAG  GTGATGCTTT  AGATTTTCA    4860
TTTGCTGCTG  GCTCTCAGCG  TGGCACTGTT  GCAGGCGGTG  TTAATACTGA  CCGCCTCACC   4920
TCTGTTTTAT  CTTCTGCTGG  TGGTTCGTTC  GGTATTTTTA  ATGGCGATGT  TTTAGGGCTA   4980
TCAGTTCGCG  CATTAAAGAC  TAATAGCCAT  TCAAAAATAT  TGTCTGTGCC  ACGTATTCTT   5040
ACGCTTTCAG  GTCAGAAGGG  TTCTATCTCT  GTTGGCCAGA  ATGTCCCTTT  TATTACTGGT   5100
CGTGTGACTG  GTGAATCTGC  CAATGTAAAT  AATCCATTTC  AGACGATTGA  GCGTCAAAAT   5160
GTAGGTATTT  CCATGAGCGT  TTTTCCTGTT  GCAATGGCTG  GCGGTAATAT  TGTTCTGGAT   5220
ATTACCAGCA  AGGCCGATAG  TTTGAGTTCT  TCTACTCAGG  CAAGTGATGT  TATTACTAAT   5280
CAAAGAAGTA  TTGCTACAAC  GGTTAATTTG  CGTGATGGAC  AGACTCTTTT  ACTCGGTGGC   5340
CTCACTGATT  ATAAAAACAC  TTCTCAAGAT  TCTGGCGTAC  CGTTCCTGTC  TAAAATCCCT   5400
TTAATCGGCC  TCCTGTTTAG  CTCCCGCTCT  GATTCCAACG  AGGAAAGCAC  GTTATACGTG   5460
CTCGTCAAAG  CAACCATAGT  ACGCGCCCTG  TAGCGGCGCA  TTAAGCGCGG  CGGGTGTGGT   5520
GGTTACGCGC  AGCGTGACCG  CTACACTTGC  CAGCGCCCTA  GCGCCCGCTC  CTTTCGCTTT   5580
CTTCCCTTCC  TTTCTCGCCA  CGTTCGCCGG  CTTTCCCCGT  CAAGCTCTAA  ATCGGGGGCT   5640
CCCTTTAGGG  TTCCGATTTA  GTGCTTTACG  GCACCTCGAC  CCCAAAAAAC  TTGATTTGGG   5700
TGATGGTTCA  CGTAGTGGGC  CATCGCCCTG  ATAGACGGTT  TTTCGCCCTT  TGACGTTGGA   5760
GTCCACGTTC  TTTAATAGTG  GACTCTTGTT  CCAAACTGGA  ACAACACTCA  ACCCTATCTC   5820
GGGCTATTCT  TTTGATTTAT  AAGGGATTTT  GCCGATTTCG  GAACCACCAT  CAAACAGGAT   5880
TTTCGCCTGC  TGGGGCAAAC  CAGCGTGGAC  CGCTTGCTGC  AACTCTCTCA  GGGCCAGGCG   5940
GTGAAGGGCA  ATCAGCTGTT  GCCCGTCTCG  CTGGTGAAAA  GAAAAACCAC  CCTGGCGCCC   6000
AATACGCAAA  CCGCCTCTCC  CCGCGCGTTG  GCCGATTCAT  TAATGCAGCT  GGCACGACAG   6060
GTTTCCCGAC  TGGAAAGCGG  GCAGTGAGCG  CAACGCAATT  AATGTGAGTT  AGCTCACTCA   6120
TTAGGCACCC  CAGGCTTTAC  ACTTTATGCT  TCCGGCTCGT  ATGTTGTGTG  GAATTGTGAG   6180
CGGATAACAA  TTTCACACGC  CAAGGAGACA  GTCATAATGA  AATACCTATT  GCCTACGGCA   6240
```

| | | | | | |
|---|---|---|---|---|---|
|GCCGCTGGAT|TGTTATTACT|CGCTGCCCAA|CCAGCCATGG|CCGAGCTCTT|CCCGCCATCT 6300|
|GATGAGCAGT|TGAAATCTGG|AACTGCCTCT|GTTGTGTGCC|TGCTGAATAA|CTTCTATCCC 6360|
|AGAGAGGCCA|AAGTACAGTG|GAAGGTGGAT|AACGCCCTCC|AATCGGGTAA|CTCCCAGGAG 6420|
|AGTGTCACAG|AGCAGGACAG|CAAGGACAGC|ACCTACAGCC|TCAGCAGCAC|CCTGACGCTG 6480|
|AGCAAAGCAG|ACTACGAGAA|ACACAAAGTC|TACGCCTGCG|AAGTCACCCA|TCAGGGCCTG 6540|
|AGCTCGCCCG|TCACAAAGAG|CTTCAACAGG|GGAGAGTGTT|CTAGAACGCG|TCACTTGGCA 6600|
|CTGGCCGTCG|TTTTACAACG|TCGTGACTGG|GAAAACCCTG|GCGTTACCCA|AGCTTAATCG 6660|
|CCTTGCAGAA|TTCCCTTTCG|CCAGCTGGCG|TAATAGCGAA|GAGGCCCGCA|CCGATCGCCC 6720|
|TTCCCAACAG|TTGCGCAGCC|TGAATGGCGA|ATGGCGCTTT|GCCTGGTTTC|CGGCACCAGA 6780|
|AGCGGTGCCG|GAAAGCTGGC|TGGAGTGCGA|TCTTCCTGAG|GCCGATACGG|TCGTCGTCCC 6840|
|CTCAAACTGG|CAGATGCACG|GTTACGATGC|GCCCATCTAC|ACCAACGTAA|CCTATCCCAT 6900|
|TACGGTCAAT|CCGCCGTTTG|TTCCCACGGA|GAATCCGACG|GGTTGTTACT|CGCTCACATT 6960|
|TAATGTTGAT|GAAAGCTGGC|TACAGGAAGG|CCAGACGCGA|ATTATTTTTG|ATGGCGTTCC 7020|
|TATTGGTTAA|AAAATGAGCT|GATTTAACAA|AAATTTAACG|CGAATTTTAA|CAAAATATTA 7080|
|ACGTTTACAA|TTTAAATATT|TGCTTATACA|ATCTTCCTGT|TTTTGGGGCT|TTTCTGATTA 7140|
|TCAACCGGGG|TACATATGAT|TGACATGCTA|GTTTTACGAT|TACCGTTCAT|CGATTCTCTT 7200|
|GTTTGCTCCA|GACTCTCAGG|CAATGACCTG|ATAGCCTTTG|TAGATCTCTC|AAAAATAGCT 7260|
|ACCCTCTCCG|GCATTAATTT|ATCAGCTAGA|ACGGTTGAAT|ATCATATTGA|TGGTGATTTG 7320|
|ACTGTCTCCG|GCCTTTCTCA|CCCTTTTGAA|TCTTTACCTA|CACATTACTC|AGGCATTGCA 7380|
|TTTAAAATAT|ATGAGGGTTC|TAAAAATTTT|TATCCTTGCG|TTGAAATAAA|GGCTTCTCCC 7440|
|GCAAAAGTAT|TACAGGGTCA|TAATGTTTTT|GGTACAACCG|ATTTAGCTTT|ATGCTCTGAG 7500|
|GCTTTATTGC|TTAATTTTGC|TAATTCTTTG|CCTTGCCTGT|ATGATTTATT|GGATGTT 7557|

( 2 ) INFORMATION FOR SEQ ID NO:5:

( i ) SEQUENCE CHARACTERISTICS:
        ( A ) LENGTH: 8118 base pairs
        ( B ) TYPE: nucleic acid
        ( C ) STRANDEDNESS: both
        ( D ) TOPOLOGY: circular ( x i ) SEQUENCE DESCRIPTION: SEQ ID NO:5:

| | | | | | |
|---|---|---|---|---|---|
|AATGCTACTA|CTATTAGTAG|AATTGATGCC|ACCTTTTCAG|CTCGCGCCCC|AAATGAAAAT 60|
|ATAGCTAAAC|AGGTTATTGA|CCATTGCGA|AATGTATCTA|ATGGTCAAAC|TAAATCTACT 120|
|CGTTCGCAGA|ATTGGGAATC|AACTGTTACA|TGGAATGAAA|CTTCCAGACA|CCGTACTTTA 180|
|GTTGCATATT|TAAAACATGT|TGAGCTACAG|CACCAGATTC|AGCAATTAAG|CTCTAAGCCA 240|
|TCTGCAAAAA|TGACCTCTTA|TCAAAGGAG|CAATTAAAGG|TACTCTCTAA|TCCTGACCTG 300|
|TTGGAGTTTG|CTTCCGGTCT|GGTTCGCTTT|GAAGCTCGAA|TTAAAACGCG|ATATTTGAAG 360|
|TCTTTCGGGC|TTCCTCTTAA|TCTTTTTGAT|GCAATCCGCT|TTGCTTCTGA|CTATAATAGT 420|
|CAGGGTAAAG|ACCTGATTTT|TGATTTATGG|TCATTCTCGT|TTTCTGAACT|GTTTAAAGCA 480|
|TTTGAGGGGG|ATTCAATGAA|TATTTATGAC|GATTCCGCAG|TATTGGACGC|TATCCAGTCT 540|
|AAACATTTTA|CTATTACCCC|CTCTGGCAAA|ACTTCTTTTG|CAAAAGCCTC|TCGCTATTTT 600|
|GGTTTTTATC|GTCGTCTGGT|AAACGAGGGT|TATGATAGTG|TTGCTCTTAC|TATGCCTCGT 660|
|AATTCCTTTT|GGCGTTATGT|ATCTGCATTA|GTTGAATGTG|GTATTCCTAA|ATCTCAACTG 720|

-continued

```
ATGAATCTTT  CTACCTGTAA  TAATGTTGTT  CCGTTAGTTC  GTTTTATTAA  CGTAGATTTT   780
TCTTCCCAAC  GTCCTGACTG  GTATAATGAG  CCAGTTCTTA  AAATCGCATA  AGGTAATTCA   840
CAATGATTAA  AGTTGAAATT  AAACCATCTC  AAGCCCAATT  TACTACTCGT  TCTGGTGTTT   900
CTCGTCAGGG  CAAGCCTTAT  TCACTGAATG  AGCAGCTTTG  TTACGTTGAT  TTGGGTAATG   960
AATATCCGGT  TCTTGTCAAG  ATTACTCTTG  ATGAAGGTCA  GCCAGCCTAT  GCGCCTGGTC  1020
TGTACACCGT  TCATCTGTCC  TCTTTCAAAG  TTGGTCAGTT  CGGTTCCCTT  ATGATTGACC  1080
GTCTGCGCCT  CGTTCCGGCT  AAGTAACATG  GAGCAGGTCG  CGGATTTCGA  CACAATTTAT  1140
CAGGCGATGA  TACAAATCTC  CGTTGTACTT  TGTTTCGCGC  TTGGTATAAT  CGCTGGGGGT  1200
CAAAGATGAG  TGTTTTAGTG  TATTCTTTCG  CCTCTTTCGT  TTTAGGTTGG  TGCCTTCGTA  1260
GTGGCATTAC  GTATTTTACC  CGTTTAATGG  AAACTTCCTC  ATGAAAAGT   CTTTAGTCCT  1320
CAAAGCCTCT  GTAGCCGTTG  CTACCCTCGT  TCCGATGCTG  TCTTTCGCTG  CTGAGGGTGA  1380
CGATCCCGCA  AAAGCGGCCT  TTAACTCCCT  GCAAGCCTCA  GCGACCGAAT  ATATCGGTTA  1440
TGCGTGGGCG  ATGGTTGTTG  TCATTGTCGG  CGCAACTATC  GGTATCAAGC  TGTTTAAGAA  1500
ATTCACCTCG  AAAGCAAGCT  GATAAACCGA  TACAATTAAA  GGCTCCTTTT  GGAGCCTTTT  1560
TTTTTGGAGA  TTTTCAACGT  GAAAAAATTA  TTATTCGCAA  TTCCTTTAGT  TGTTCCTTTC  1620
TATTCTCACT  CCGCTGAAAC  TGTTGAAAGT  TGTTTAGCAA  AACCCCATAC  AGAAAATTCA  1680
TTTACTAACG  TCTGGAAAGA  CGACAAAACT  TTAGATCGTT  ACGCTAACTA  TGAGGGTTGT  1740
CTGTGGAATG  CTACAGGCGT  TGTAGTTTGT  ACTGGTGACG  AAACTCAGTG  TTACGGTACA  1800
TGGGTTCCTA  TTGGGCTTGC  TATCCCTGAA  AATGAGGGTG  GTGGCTCTGA  GGGTGGCGGT  1860
TCTGAGGGTG  GCGGTTCTGA  GGGTGGCGGT  ACTAAACCTC  CTGAGTACGG  TGATACACCT  1920
ATTCCGGGCT  ATACTTATAT  CAACCCTCTC  GACGGCACTT  ATCCGCCTGG  TACTGAGCAA  1980
AACCCCGCTA  ATCCTAATCC  TTCTCTTGAG  GAGTCTCAGC  CTCTTAATAC  TTTCATGTTT  2040
CAGAATAATA  GGTTCCGAAA  TAGGCAGGGG  GCATTAACTG  TTTATACGGG  CACTGTTACT  2100
CAAGGCACTG  ACCCCGTTAA  AACTTATTAC  CAGTACACTC  CTGTATCATC  AAAAGCCATG  2160
TATGACGCTT  ACTGGAACGG  TAAATTCAGA  GACTGCGCTT  TCCATTCTGG  CTTTAATGAA  2220
GATCCATTCG  TTTGTGAATA  TCAAGGCCAA  TCGTCTGACC  TGCCTCAACC  TCCTGTCAAT  2280
GCTGGCGGCG  GCTCTGGTGG  TGGTTCTGGT  GGCGGCTCTG  AGGGTGGTGG  CTCTGAGGGT  2340
GGCGGTTCTG  AGGGTGGCGG  CTCTGAGGGA  GGCGGTTCCG  GTGGTGGCTC  TGGTTCCGGT  2400
GATTTTGATT  ATGAAAAGAT  GGCAAACGCT  AATAAGGGGG  CTATGACCGA  AAATGCCGAT  2460
GAAAACGCGC  TACAGTCTGA  CGCTAAAGGC  AAACTTGATT  CTGTCGCTAC  TGATTACGGT  2520
GCTGCTATCG  ATGGTTTCAT  TGGTGACGTT  TCCGGCCTTG  CTAATGGTAA  TGGTGCTACT  2580
GGTGATTTTG  CTGGCTCTAA  TTCCCAAATG  GCTCAAGTCG  GTGACGGTGA  TAATTCACCT  2640
TTAATGAATA  ATTTCCGTCA  ATATTTACCT  TCCCTCCCTC  AATCGGTTGA  ATGTCGCCCT  2700
TTTGTCTTTA  GCGCTGGTAA  ACCATATGAA  TTTTCTATTG  ATTGTGACAA  AATAAACTTA  2760
TTCCGTGGTG  TCTTTGCGTT  TCTTTTATAT  GTTGCCACCT  TTATGTATGT  ATTTTCTACG  2820
TTTGCTAACA  TACTGCGTAA  TAAGGAGTCT  TAATCATGCC  AGTTCTTTTG  GGTATTCCGT  2880
TATTATTGCG  TTTCCTCGGT  TTCCTTCTGG  TAACTTTGTT  CGGCTATCTG  CTTACTTTTC  2940
TTAAAAAGGG  CTTCGGTAAG  ATAGCTATTG  CTATTTCATT  GTTTCTTGCT  CTTATTATTG  3000
GGCTTAACTC  AATTCTTGTG  GGTTATCTCT  CTGATATTAG  CGCTCAATTA  CCCTCTGACT  3060
TTGTTCAGGG  TGTTCAGTTA  ATTCTCCCGT  CTAATGCGCT  TCCCTGTTTT  TATGTTATTC  3120
```

```
TCTCTGTAAA GGCTGCTATT TTCATTTTTG ACGTTAAACA AAAAATCGTT TCTTATTTGG   3180
ATTGGGATAA ATAATATGGC TGTTTATTTT GTAACTGGCA AATTAGGCTC TGGAAAGACG   3240
CTCGTTAGCG TTGGTAAGAT TCAGGATAAA ATTGTAGCTG GGTGCAAAAT AGCAACTAAT   3300
CTTGATTTAA GGCTTCAAAA CCTCCCGCAA GTCGGGAGGT TCGCTAAAAC GCCTCGCGTT   3360
CTTAGAATAC CGGATAAGCC TTCTATATCT GATTTGCTTG CTATTGGGCG CGGTAATGAT   3420
TCCTACGATG AAAATAAAAA CGGCTTGCTT GTTCTCGATG AGTGCGGTAC TTGGTTTAAT   3480
ACCCGTTCTT GGAATGATAA GGAAAGACAG CCGATTATTG ATTGGTTTCT ACATGCTCGT   3540
AAATTAGGAT GGGATATTAT TTTTCTTGTT CAGGACTTAT CTATTGTTGA TAAACAGGCG   3600
CGTTCTGCAT TAGCTGAACA TGTTGTTTAT TGTCGTCGTC TGGACAGAAT TACTTTACCT   3660
TTTGTCGGTA CTTTATATTC TCTTATTACT GGCTCGAAAA TGCCTCTGCC TAAATTACAT   3720
GTTGGCGTTG TTAAATATGG CGATTCTCAA TTAAGCCCTA CTGTTGAGCG TTGGCTTTAT   3780
ACTGGTAAGA ATTTGTATAA CGCATATGAT ACTAAACAGG CTTTTTCTAG TAATTATGAT   3840
TCCGGTGTTT ATTCTTATTT AACGCCTTAT TTATCACACG GTCGGTATTT CAAACCATTA   3900
AATTTAGGTC AGAAGATGAA GCTTACTAAA ATATATTTGA AAAGTTTTC ACGCGTTCTT    3960
TGTCTTGCGA TTGGATTTGC ATCAGCATTT ACATATAGTT ATATAACCCA ACCTAAGCCG   4020
GAGGTTAAAA AGGTAGTCTC TCAGACCTAT GATTTTGATA AATTCACTAT TGACTCTTCT   4080
CAGCGTCTTA ATCTAAGCTA TCGCTATGTT TTCAAGGATT CTAAGGGAAA ATTAATTAAT   4140
AGCGACGATT TACAGAAGCA AGGTTATTCA CTCACATATA TTGATTTATG TACTGTTTCC   4200
ATTAAAAAAG GTAATTCAAA TGAAATTGTT AAATGTAATT AATTTTGTTT TCTTGATGTT   4260
TGTTTCATCA TCTTCTTTTG CTCAGGTAAT TGAAATGAAT AATTCGCCTC TGCGCGATTT   4320
TGTAACTTGG TATTCAAAGC AATCAGGCGA ATCCGTTATT GTTTCTCCCG ATGTAAAAGG   4380
TACTGTTACT GTATATTCAT CTGACGTTAA ACCTGAAAAT CTACGCAATT TCTTTATTTC   4440
TGTTTTACGT GCTAATAATT TTGATATGGT TGGTTCAATT CCTTCCATAA TTCAGAAGTA   4500
TAATCCAAAC AATCAGGATT ATATTGATGA ATTGCCATCA TCTGATAATC AGGAATATGA   4560
TGATAATTCC GCTCCTTCTG GTGGTTTCTT TGTTCCGCAA AATGATAATG TTACTCAAAC   4620
TTTTAAAATT AATAACGTTC GGGCAAAGGA TTTAATACGA GTTGTCGAAT TGTTTGTAAA   4680
GTCTAATACT TCTAAATCCT CAAATGTATT ATCTATTGAC GGCTCTAATC TATTAGTTGT   4740
TAGTGCACCT AAAGATATTT TAGATAACCT TCCTCAATTC CTTTCTACTG TTGATTTGCC   4800
AACTGACCAG ATATTGATTG AGGGTTTGAT ATTTGAGGTT CAGCAAGGTG ATGCTTTAGA   4860
TTTTTCATTT GCTGCTGGCT CTCAGCGTGG CACTGTTGCA GGCGGTGTTA ATACTGACCG   4920
CCTCACCTCT GTTTTATCTT CTGCTGGTGG TTCGTTCGGT ATTTTTAATG GCGATGTTTT   4980
AGGGCTATCA GTTCGCGCAT TAAAGACTAA TAGCCATTCA AAAATATTGT CTGTGCCACG   5040
TATTCTTACG CTTTCAGGTC AGAAGGGTTC TATCTCTGTT GGCCAGAATG TCCCTTTTAT   5100
TACTGGTCGT GTGACTGGTG AATCTGCCAA TGTAAATAAT CCATTTCAGA CGATTGAGCG   5160
TCAAAATGTA GGTATTTCCA TGAGCGTTTT TCCTGTTGCA ATGGCTGGCG TAATATTGT    5220
TCTGGATATT ACCAGCAAGG CCGATAGTTT GAGTTCTTCT ACTCAGGCAA GTGATGTTAT   5280
TACTAATCAA AGAAGTATTG CTACAACGGT TAATTTGCGT GATGGACAGA CTCTTTTACT   5340
CGGTGGCCTC ACTGATTATA AAAACACTTC TCAAGATTCT GGCGTACCGT TCCTGTCTAA   5400
AATCCCTTTA ATCGGCCTCC TGTTTAGCTC CCGCTCTGAT TCCAACGAGG AAAGCACGTT   5460
ATACGTGCTC GTCAAAGCAA CCATAGTACG CGCCCTGTAG CGGCGCATTA AGCGCGGCGG   5520
```

```
GTGTGGTGGT TACGCGCAGC GTGACCGCTA CACTTGCCAG CGCCCTAGCG CCCGCTCCTT    5580
TCGCTTTCTT CCCTTCCTTT CTCGCCACGT TCGCCGGCTT TCCCCGTCAA GCTCTAAATC    5640
GGGGGCTCCC TTTAGGGTTC CGATTAGTG  CTTTACGGCA CCTCGACCCC AAAAAACTTG    5700
ATTTGGGTGA TGGTTCACGT AGTGGGCCAT CGCCCTGATA GACGGTTTTT CGCCCTTTGA    5760
CGTTGGAGTC CACGTTCTTT AATAGTGGAC TCTTGTTCCA AACTGGAACA ACACTCAACC    5820
CTATCTCGGG CTATTCTTTT GATTTATAAG GGATTTTGCC GATTTCGGAA CCACCATCAA    5880
ACAGGATTTT CGCCTGCTGG GGCAAACCAG CGTGGACCGC TTGCTGCAAC TCTCTCAGGG    5940
CCAGGCGGTG AAGGGCAATC AGCTGTTGCC CGTCTCGCTG GTGAAAAGAA AAACCACCCT    6000
GGCGCCCAAT ACGCAAACCG CCTCTCCCCG CGCGTTGGCC GATTCATTAA TGCAGCTGGC    6060
ACGACAGGTT TCCCGACTGG AAAGCGGGCA GTGAGCGCAA CGCAATTAAT GTGAGTTAGC    6120
TCACTCATTA GGCACCCCAG GCTTTACACT TTATGCTTCC GGCTCGTATG TTGTGTGGAA    6180
TTGTGAGCGG ATAACAATTT CACACGCCAA GGAGACAGTC ATAATGAAAT ACCTATTGCC    6240
TACGGCAGCC GCTGGATTGT TATTACTCGC TGCCCAACCA GCCATGGCCG AGCTCTTCCC    6300
GCCATCTGAT GAGCAGTTGA AATCTGGAAC TGCCTCTGTT GTGTGCCTGC TGAATAACTT    6360
CTATCCCAGA GAGGCCAAAG TACAGTGGAA GGTGGATAAC GCCCTCCAAT CGGGTAACTC    6420
CCAGGAGAGT GTCACAGAGC AGGACAGCAA GGACAGCACC TACAGCCTCA GCAGCACCCT    6480
GACGCTGAGC AAAGCAGACT ACGAGAAACA CAAAGTCTAC GCCTGCGAAG TCACCCATCA    6540
GGGCCTGAGC TCGCCCGTCA CAAAGAGCTT CAACAGGGGA GAGTGTTCTA GAACGCGTCA    6600
CTTGGCACTG GCCGTCGTTT TACAACGTCG TGACTGGGAA AACCCTGGCG TTACCCAAGC    6660
TTTGTACATG GAGAAAATAA AGTGAAACAA AGCACTATTG CACTGGCACT CTTACCGTTA    6720
CTGTTTACCC CTGTGGCAAA AGCCGCCTCC ACCAAGGGCC CATCGGTCTT CCCCCTGGCA    6780
CCCTCCTCCA AGAGCACCTC TGGGGGCACA GCGGCCCTGG GCTGCCTGGT CAAGACTAAT    6840
TCCCCGAACC GGTGACGGTG TCGTGGAACT CAGGCGCCCT GACCAGCGGC GTGCACACCT    6900
TCCCGGCTGT CCTACAGTCC TCAGGACTCT ACTCCCTCAG CAGCGTGGTG ACCGTGCCCT    6960
CCAGCAGCTT GGGCACCCAG ACCTACATCT GCAACGTGAA TCACAAGCCC AGCAACACCA    7020
AGGTGGACAA GAAAGCAGAG CCCAAATCTT GTACTAGTGG ATCCTACCCG TACGACGTTC    7080
CGGACTACGC TTCTTAGGCT GAAGGCGATG ACCCTGCTAA GGCTGCATTC AATAGTTTAC    7140
AGGCAAGTGC TACTGAGTAC ATTGGCTACG CTTGGGCTAT GGTAGTAGTT ATAGTTGGTG    7200
CTACCATAGG GATTAAATTA TTCAAAAAGT TTACGAGCAA GGCTTCTTAA GCAATAGCGA    7260
AGAGGCCCGC ACCGATCGCC CTTCCCAACA GTTGCGCAGC CTGAATGGCG AATGGCGCTT    7320
TGCCTGGTTT CCGGCACCAG AAGCGGTGCC GGAAAGCTGG CTGGAGTGCG ATCTTCCTGA    7380
GGCCGATACG GTCGTCGTCC CCTCAAACTG GCAGATGCAC GGTTACGATG CGCCCATCTA    7440
CACCAACGTA ACCTATCCCA TTACGGTCAA TCCGCCGTTT GTTCCCACGG AGAATCCGAC    7500
GGGTTGTTAC TCGCTCACAT TTAATGTTGA TGAAAGCTGG CTACAGGAAG GCCAGACGCG    7560
AATTATTTTT GATGGCGTTC CTATTGGTTA AAAAATGAGC TGATTTAACA AAAATTTAAC    7620
GCGAATTTTA ACAAAATATT AACGTTTACA ATTTAAATAT TTGCTTATAC AATCTTCCTG    7680
TTTTTGGGGC TTTTCTGATT ATCAACGGG  GTACATATGA TTGACATGCT AGTTTTACGA    7740
TTACCGTTCA TCGATTCTCT TGTTTGCTCC AGACTCTCAG GCAATGACCT GATAGCCTTT    7800
GTAGATCTCT CAAAAATAGC TACCCTCTCC GGCATTAATT TATCAGCTAG AACGGTTGAA    7860
TATCATATTG ATGGTGATTT GACTGTCTCC GGCCTTTCTC ACCCTTTTGA ATCTTTACCT    7920
```

| ACACATTACT | CAGGCATTGC | ATTTAAAATA | TATGAGGGTT | CTAAAAATTT | TTATCCTTGC | 7980 |
|---|---|---|---|---|---|---|
| GTTGAAATAA | AGGCTTCTCC | CGCAAAAGTA | TTACAGGGTC | ATAATGTTTT | TGGTACAACC | 8040 |
| GATTTAGCTT | TATGCTCTGA | GGCTTTATTG | CTTAATTTTG | CTAATTCTTT | GCCTTGCCTG | 8100 |
| TATGATTTAT | TGGACGTT | | | | | 8118 |

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(5, "")
        ( D ) OTHER INFORMATION: /note= "S REPRESENTS EQUAL MIXTURE
            OF G AND C"

( i x ) FEATURE:
        ( A ) NAME/KEY: misc_difference
        ( B ) LOCATION: replace(6, "")
        ( D ) OTHER INFORMATION: /note= "M REPRESENTS EQUAL MIXTURE
            OF A AND C"

( i x ) FEATURE:
        ( A ) NAME/KEY: misc_difference
        ( B ) LOCATION: replace(8, "")
        ( D ) OTHER INFORMATION: /note= "R REPRESENTS EQUAL MIXTURE
            OF A AND G"

( i x ) FEATURE:
        ( A ) NAME/KEY: misc_difference
        ( B ) LOCATION: replace(11, "")
        ( D ) OTHER INFORMATION: /note= "K REPRESENTS EQUAL MIXTURE
            OF G AND T"

( i x ) FEATURE:
        ( A ) NAME/KEY: misc_difference
        ( B ) LOCATION: replace(20, "")
        ( D ) OTHER INFORMATION: /note= "W REPRESENTS EQUAL MIXTURE
            OF A AND T"

( x i ) SEQUENCE DESCRIPTION: SEQ ID NO:6:

AGGTSMARCT KCTCGAGTCW GG                                      22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AGGTCCAGCT GCTCGAGTCT GG                                      22

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AGGTCCAGCT GCTCGAGTCA GG                                      22

( 2 ) INFORMATION FOR SEQ ID NO:9:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:9:

AGGTCCAGCT TCTCGAGTCT GG 22

( 2 ) INFORMATION FOR SEQ ID NO:10:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

AGGTCCAGCT TCTCGAGTCA GG 22

( 2 ) INFORMATION FOR SEQ ID NO:11:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

AGGTCCAACT GCTCGAGTCT GG 22

( 2 ) INFORMATION FOR SEQ ID NO:12:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

AGGTCCAACT GCTCGAGTCA GG 22

( 2 ) INFORMATION FOR SEQ ID NO:13:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

AGGTCCAACT TCTCGAGTCT GG 22

( 2 ) INFORMATION FOR SEQ ID NO:14:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

AGGTCCAACT TCTCGAGTCA GG 22

( 2 ) INFORMATION FOR SEQ ID NO:15:

( i ) SEQUENCE CHARACTERISTICS:
    ( A ) LENGTH: 22 base pairs (B) TYPE: nucleic acid
                (C) STRANDEDNESS: single
                (D) TOPOLOGY: linear (ix) FEATURE:
                (A) NAME/KEY: misc_difference
                (B) LOCATION: replace(5..6, "")
                (D) OTHER INFORMATION: /note= "N=INOSINE"

(ix) FEATURE:
                (A) NAME/KEY: misc_difference
                (B) LOCATION: replace(8, "")
                (D) OTHER INFORMATION: /note= "N=INOSINE"

(ix) FEATURE:
                (A) NAME/KEY: misc_difference
                (B) LOCATION: replace(11, "")
                (D) OTHER INFORMATION: /note= "N=INOSINE"

(ix) FEATURE:
                (A) NAME/KEY: misc_difference
                (B) LOCATION: replace(20, "")
                (D) OTHER INFORMATION: /note= "W REPRESENTS EQUAL MIXTURE
                        OF A AND T"

(xi) SEQUENCE DESCRIPTION: SEQ ID NO:15:

AGGTNNANCT NCTCGAGTCW GG                                                    22

(2) INFORMATION FOR SEQ ID NO:16:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (xi) SEQUENCE DESCRIPTION: SEQ ID NO:16:

CTATTAACTA GTAACGGTAA CAGTGGTGCC TTGCCCCA                                   38

(2) INFORMATION FOR SEQ ID NO:17:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:17:

AGGCTTACTA GTACAATCCC TGGGCACAAT                                            30

(2) INFORMATION FOR SEQ ID NO:18:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (xi) SEQUENCE DESCRIPTION: SEQ ID NO:18:

CCAGTTCCGA GCTCGTTGTG ACTCAGGAAT CT                                         32

(2) INFORMATION FOR SEQ ID NO:19:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (xi) SEQUENCE DESCRIPTION: SEQ ID NO:19:

CCAGTTCCGA GCTCGTGTTG ACGCAGCCGC CC                                         32

( 2 ) INFORMATION FOR SEQ ID NO:20:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CCAGTTCCGA GCTCGTGCTC ACCCAGTCTC CA    32

( 2 ) INFORMATION FOR SEQ ID NO:21:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CCAGTTCCGA GCTCCAGATG ACCCAGTCTC CA    32

( 2 ) INFORMATION FOR SEQ ID NO:22:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CCAGATGTGA GCTCGTGATG ACCCAGACTC CA    32

( 2 ) INFORMATION FOR SEQ ID NO:23:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

CCAGATGTGA GCTCGTCATG ACCCAGTCTC CA    32

( 2 ) INFORMATION FOR SEQ ID NO:24:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CCAGTTCCGA GCTCGTGATG ACACAGTCTC CA    32

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GCAGCATTCT AGAGTTTCAG CTCCAGCTTG CC    32

( 2 ) INFORMATION FOR SEQ ID NO:26:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GCGCCGTCTA GAATTAACAC TCATTCCTGT TGAA        34

( 2 ) INFORMATION FOR SEQ ID NO:27:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GATCCTAGGC TGAAGGCGAT GACCCTGCTA AGGCTGC        37

( 2 ) INFORMATION FOR SEQ ID NO:28:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

ATTCAATAGT TTACAGGCAA GTGCTACTGA GTACA        35

( 2 ) INFORMATION FOR SEQ ID NO:29:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

TTGGCTACGC TTGGGCTATG GTAGTAGTTA TAGTT        35

( 2 ) INFORMATION FOR SEQ ID NO:30:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GGTGCTACCA TAGGGATTAA ATTATTCAAA AAGTT        35

( 2 ) INFORMATION FOR SEQ ID NO:31:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

TACGAGCAAG GCTTCTTA        18

( 2 ) INFORMATION FOR SEQ ID NO:32:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:32:

AGCTTAAGAA GCCTTGCTCG TAAACTTTTT GAATAATTT                   39

( 2 ) INFORMATION FOR SEQ ID NO:33:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:33:

AATCCCTATG GTAGCACCAA CTATAACTAC TACCAT                      36

( 2 ) INFORMATION FOR SEQ ID NO:34:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:34:

AGCCCAAGCG TAGCCAATGT ACTCAGTAGC ACTTG                       35

( 2 ) INFORMATION FOR SEQ ID NO:35:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:35:

CCTGTAAACT ATTGAATGCA GCCTTAGCAG GGTC                        34

( 2 ) INFORMATION FOR SEQ ID NO:36:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:36:

ATCGCCTTCA GCCTAG                                            16

( 2 ) INFORMATION FOR SEQ ID NO:37:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:37:

CATTTTTGCA GATGGCTTAG A                                      21

( 2 ) INFORMATION FOR SEQ ID NO:38:

( i ) SEQUENCE CHARACTERISTICS:
  ( A ) LENGTH: 18 base pairs (B) TYPE: nucleic acid
(C) STRANDEDNESS: single
(D) TOPOLOGY: linear (xi) SEQUENCE DESCRIPTION: SEQ ID NO:38:

TAGCATTAAC GTCCAATA 18

(2) INFORMATION FOR SEQ ID NO:39:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:39:

ATATATTTTA GTAAGCTTCA TCTTCT 26

(2) INFORMATION FOR SEQ ID NO:40:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:40:

GACAAAGAAC GCGTGAAAAC TTT 23

(2) INFORMATION FOR SEQ ID NO:41:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:41:

GCGGGCCTCT TCGCTATTGC TTAAGAAGCC TTGCT 35

(2) INFORMATION FOR SEQ ID NO:42:

(i) SEQUENCE CHARACTERISTICS:
(A) LENGTH: 43 base pairs
(B) TYPE: nucleic acid
(C) STRANDEDNESS: single
(D) TOPOLOGY: linear (xi) SEQUENCE DESCRIPTION: SEQ ID NO:42:

AAACGACGGC CAGTGCCAAG TGACGCGTGT GAAATTGTTA TCC 43

(2) INFORMATION FOR SEQ ID NO:43:

(i) SEQUENCE CHARACTERISTICS:
(A) LENGTH: 43 base pairs
(B) TYPE: nucleic acid
(C) STRANDEDNESS: single
(D) TOPOLOGY: linear (xi) SEQUENCE DESCRIPTION: SEQ ID NO:43:

GGCGAAAGGG AATTCTGCAA GGCGATTAAG CTTGGGTAAC GCC 43

(2) INFORMATION FOR SEQ ID NO:44:

(i) SEQUENCE CHARACTERISTICS:
(A) LENGTH: 36 base pairs
(B) TYPE: nucleic acid
(C) STRANDEDNESS: single (D) TOPOLOGY: linear (x i) SEQUENCE DESCRIPTION: SEQ ID NO:44:

GGCGTTACCC AAGCTTTGTA CATGGAGAAA ATAAAG 36

(2) INFORMATION FOR SEQ ID NO:45:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (x i) SEQUENCE DESCRIPTION: SEQ ID NO:45:

TGAAACAAAG CACTATTGCA CTGGCACTCT TACCGTTACC GT 42

(2) INFORMATION FOR SEQ ID NO:46:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (x i) SEQUENCE DESCRIPTION: SEQ ID NO:46:

TACTGTTTAC CCCTGTGACA AAAGCCGCCC AGGTCCAGCT GC 42

(2) INFORMATION FOR SEQ ID NO:47:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (x i) SEQUENCE DESCRIPTION: SEQ ID NO:47:

TCGAGTCAGG CCTATTGTGC CCAGGGATTG TACTAGTGGA TCCG 44

(2) INFORMATION FOR SEQ ID NO:48:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:48:

TGGCGAAAGG GAATTCGGAT CCACTAGTAC AATCCCTG 38

(2) INFORMATION FOR SEQ ID NO:49:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (x i) SEQUENCE DESCRIPTION: SEQ ID NO:49:

GGCACAATAG GCCTGACTCG AGCAGCTGGA CCAGGGCGGC TT 42

(2) INFORMATION FOR SEQ ID NO:50:

(i) SEQUENCE CHARACTERISTICS:
        (A) LENGTH: 42 base pairs
        (B) TYPE: nucleic acid
        (C) STRANDEDNESS: single
        (D) TOPOLOGY: linear ( x i ) SEQUENCE DESCRIPTION: SEQ ID NO:50:

TTGTCACAGG GGTAAACAGT AACGGTAACG GTAAGTGTGC CA                                                              42

( 2 ) INFORMATION FOR SEQ ID NO:51:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

GTGCAATAGT GCTTTGTTTC ACTTTATTTT CTCCATGTAC AA                                                              42

( 2 ) INFORMATION FOR SEQ ID NO:52:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

TAACGGTAAG AGTGCCAGTG C                                                                                     21

( 2 ) INFORMATION FOR SEQ ID NO:53:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CACCTTCATG AATTCGGCAA GGAGACAGTC AT                                                                         32

( 2 ) INFORMATION FOR SEQ ID NO:54:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

AATTCGCCAA GGAGACAGTC AT                                                                                    22

( 2 ) INFORMATION FOR SEQ ID NO:55:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

AATGAAATAC CTATTGCCTA CGGCAGCCGC TGGATTGTT                                                                  39

( 2 ) INFORMATION FOR SEQ ID NO:56:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

ATTACTCGCT GCCCAACCAG CCATGGCCGA GCTCGTGAT 39

(2) INFORMATION FOR SEQ ID NO:57:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:57:

GACCCAGACT CCAGATATCC AACAGGAATG AGTGTTAAT 39

(2) INFORMATION FOR SEQ ID NO:58:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:58:

TCTAGAACGC GTC 13

(2) INFORMATION FOR SEQ ID NO:59:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:59:

TTCAGGTTGA AGCTTACGCG TTCTAGAATT AACACTCATT CCTGT 45

(2) INFORMATION FOR SEQ ID NO:60:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:60:

TGGATATCTG GAGTCTGGGT CATCACGAGC TCGGCCATG 39

(2) INFORMATION FOR SEQ ID NO:61:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:61:

GCTGGTTGGG CAGCGAGTAA TAACAATCCA GCGGCTGCC 39

(2) INFORMATION FOR SEQ ID NO:62:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:62:

GTAGGCAATA GGTATTTCAT TATGACTGTC CTTGGCG 37

( 2 ) INFORMATION FOR SEQ ID NO:63:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

TGACTGTCTC CTTGGCGTGT GAAATTGTTA 30

( 2 ) INFORMATION FOR SEQ ID NO:64:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

TAACACTCAT TCCGGATGGA ATTCTGGAGT CTGGGT 36

( 2 ) INFORMATION FOR SEQ ID NO:65:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

GCCAGTGCCA AGTGACGCGT TCTA 24

( 2 ) INFORMATION FOR SEQ ID NO:66:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

ATATATTTTA GTAAGCTTCA TCTTCT 26

( 2 ) INFORMATION FOR SEQ ID NO:67:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

GACAAAGAAC GCGTGAAAAC TTT 23

( 2 ) INFORMATION FOR SEQ ID NO:68:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

CTGAACCTGT CTGGACCAC AGTTGATGCT ATAGGATCAG ATCTAGAATT CATTTAGAGA 60

CTGGCCTGGC TTCTGC 76

( 2 ) INFORMATION FOR SEQ ID NO:69:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

```
TCGACCGTTG GTAGGAATAA TGCAATTAAT GGAGTAGCTC TAAATTCAGA ATTCATCTAC    60

ACCCAGTGCA TCCAGTAGCT                                                80
```

( 2 ) INFORMATION FOR SEQ ID NO:70:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

```
GGTAAACAGT AACGGTAAGA GTGCCAG                                        27
```

( 2 ) INFORMATION FOR SEQ ID NO:71:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

```
CGCCTTCAGC CTAAGAAGCG TAGTCCGGAA CGTCGTACGG GTAGGATCCA CTAG           54
```

( 2 ) INFORMATION FOR SEQ ID NO:72:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

```
CACCGGTTCG GGGAATTAGT CTTGACCAGG CAGCCCAGGG C                         41
```

( 2 ) INFORMATION FOR SEQ ID NO:73:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

```
ATTCCACACA TTATACGAGC CGGAAGCATA AAGTGTCAAG CCTGGGGTGC C              51
```

( 2 ) INFORMATION FOR SEQ ID NO:74:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

```
CTGCTCATCA GATGGCGGGA AGAGCTCGGC CATGGCTGGT TG                        42
```

( 2 ) INFORMATION FOR SEQ ID NO:75:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

GAACAGAGTG ACCGAGGGGG CGAGCTCGGC CATGGCTGGT TG        42